United States Patent
Zhao

(10) Patent No.: US 10,975,112 B2
(45) Date of Patent: *Apr. 13, 2021

(54) LINKERS FOR CONJUGATION OF CELL-BINDING MOLECULES

(71) Applicant: Suzhou M-Conj Biotech Co., Ltd., Suzhou (CN)

(72) Inventor: Robert Yongxin Zhao, Lexington, MA (US)

(73) Assignee: HANGZHOU DAC BIOTECH CO., LTD., Hangzhou (CN)

(*) Notice: Subject to any disclaimer, the term of this patent is extended or adjusted under 35 U.S.C. 154(b) by 402 days.

This patent is subject to a terminal disclaimer.

(21) Appl. No.: 14/740,403

(22) Filed: Jun. 16, 2015

(65) Prior Publication Data

US 2015/0284416 A1 Oct. 8, 2015

(51) Int. Cl.
| | | |
|---|---|---|
| *C07F 9/6558* | (2006.01) | |
| *C07F 9/572* | (2006.01) | |
| *C07F 9/6561* | (2006.01) | |
| *C07F 9/6584* | (2006.01) | |
| *A61K 45/06* | (2006.01) | |
| *A61K 47/68* | (2017.01) | |
| *C07F 9/58* | (2006.01) | |

(52) U.S. Cl.
CPC .......... *C07F 9/65583* (2013.01); *A61K 45/06* (2013.01); *A61K 47/6803* (2017.08); *A61K 47/6851* (2017.08); *A61K 47/6889* (2017.08); *C07F 9/572* (2013.01); *C07F 9/58* (2013.01); *C07F 9/6561* (2013.01); *C07F 9/6584* (2013.01)

(58) Field of Classification Search
CPC .. A61K 47/56; A61K 47/551; A61K 47/6803; A61K 47/6889; C07F 9/572; C07F 9/6561; C07F 9/6584; C07F 9/65583; C07F 9/58

See application file for complete search history.

(56) References Cited

U.S. PATENT DOCUMENTS

| 6,056,973 A * | 5/2000 | Allen ................ A61K 9/127 424/450 |
| 2008/0050310 A1* | 2/2008 | Ebens, Jr. .......... C07K 16/2803 424/1.49 |

FOREIGN PATENT DOCUMENTS

| WO | WO2006/042269 | * | 4/2006 | |
| WO | WO2014/080251 | * | 5/2014 | .......... C07C 317/02 |
| WO | WO-2015157595 A1 | * | 10/2015 | ......... A61K 47/6803 |
| WO | WO2016/147031 | * | 7/2016 | |

OTHER PUBLICATIONS

"CFTM dyes selection guide" (downloaded from www.biotium.com on Feb. 23, 27).*
McCombs and Owen, The AAPS Journal, 2015, vol. 17, pp. 339-351.*
Sangha and Butts, Clinical Cancer Research, 2007, vol. 13, suppl. 15, pp. 4652s-4654s.*
Stopeck et al, Clinical Cancer Research, 2001, vol. 7, pp. 2285-2291.*
Harzstark and Small, Expert Opinion on Biological therapy, 2007, vol. 7, pp. 1275-1280.*
Irani et al, Molecular Immunology, 2015, vol. 67, pp. 171-182.*
Pelegrin et al, Trends in Microbiology, 2015, vol. 23, pp. 653-665.*
Pinto et al (Cancer Chemotherapy and Pharmacology, 2011, vol. 67, pp. 275-284).*
Gyles, Canadian Journal of Microbiology, 1992, vol. 38, pp. 734-746 (Year: 1992).*
Guichard et al, Nature, 2010, vol. 467, pp. 854-858 (Year: 2010).*
Musselli et al, International Journal of Cancer, 2002, vol. 97, pp. 660-667 (Year: 2002).*
May et al, Journal of Immunology, 2003, vol. 171, pp. 4905-4912 (Year: 2003).*
Mansur et al, Am J Respir Crit Care Med, 1999, vol. 159, pp. 1796-1802 (Year: 1999).*
Cheever et al, Clinical Cancer Research, 2009, Vo. 15, pp. 5323-5337 (Year: 2009).*
Franzman et al, final published article, Int Journal of Antimicrobial Agents, 2009, vol. 33, pp. 14-20 (Year: 2009).*
Majumdar et al (Advanced Drug Delivery Reviews, 2004, vol. 56, pp. 1437-1452) (Year: 2004).*
Somasiri et al (Cancer Research, 2004, vol. 64, pp. 5068-5073 (Year: 2004).*
Petrus et al, Angew. Chem. Int. Ed, 2009, vol. 48, pp. 1022-1028 (Year: 2009).*
Chari et al, Angew Chem Int Ed, 2014, vol. 53, pp. 3796-3827 (Year: 2014).*
Russell-Jones et al (Journal of Inorganic Biochemistry, 2004, vol. 98, pp. 1625-1633) (Year: 2004).*
NCT03162250, accessed from ClinicalTrial.gov on Jun. 11, 2020 (Year: 2020).*
Wang-Lin et al, mAbs, 2018, vol. 10, pp. 1131-1143 (Year: 2018).*
Mariathasan and Tan (Trends in Molecular Medicine, 2017, vol. 23, pp. 135-149) (Year: 2017).*

* cited by examiner

*Primary Examiner* — Karen A. Canella
(74) *Attorney, Agent, or Firm* — Buchanan Ingersoll & Rooney PC

(57) ABSTRACT

Cell binding agent-drug conjugates comprising hydrophilic linkers, and methods of using such linkers and conjugates are provided.

35 Claims, 18 Drawing Sheets

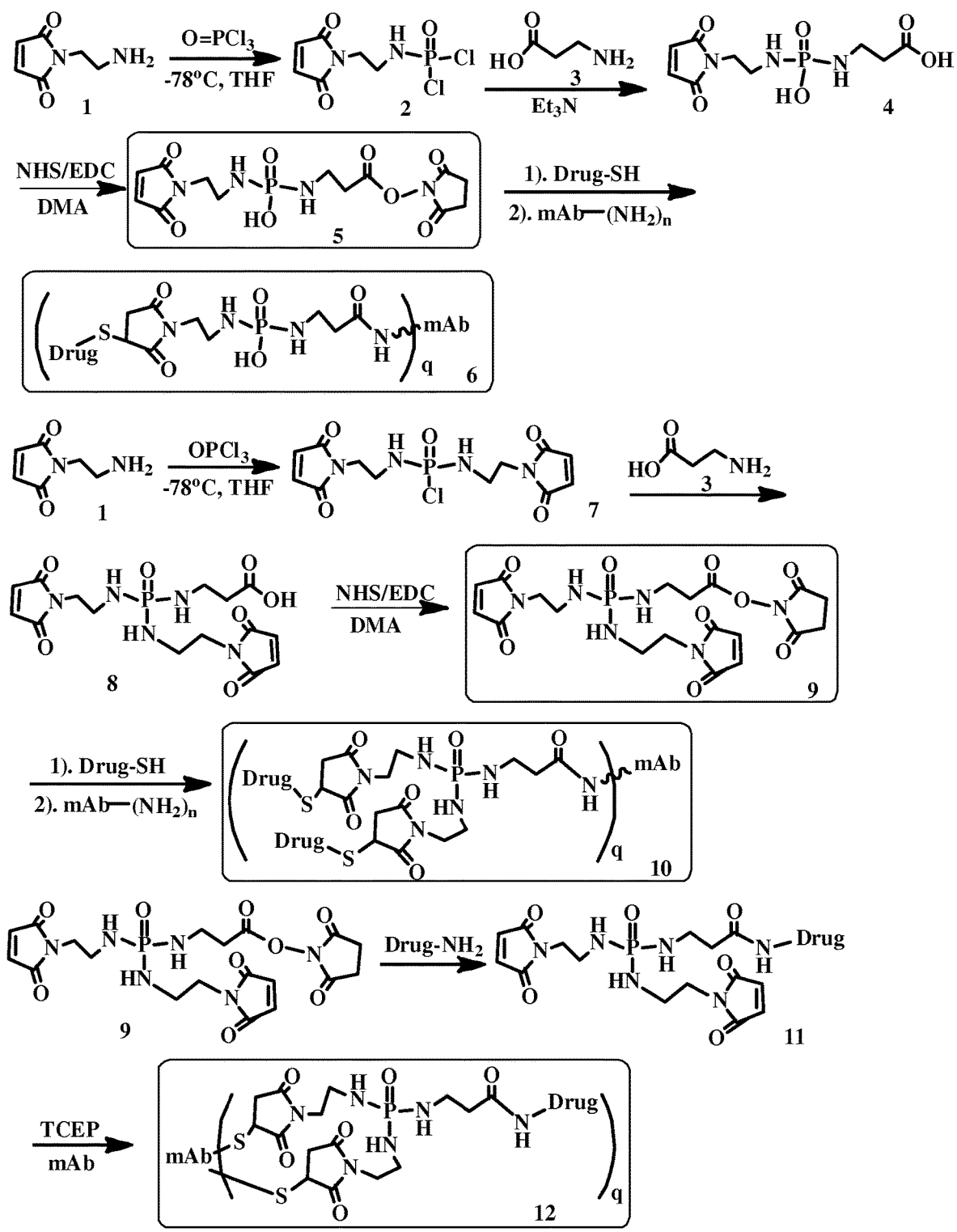
Figure 1. The synthesis of phosphamide linkers containing maleimide groups and the application of these linkers in the conjugation of an antibody with drugs.

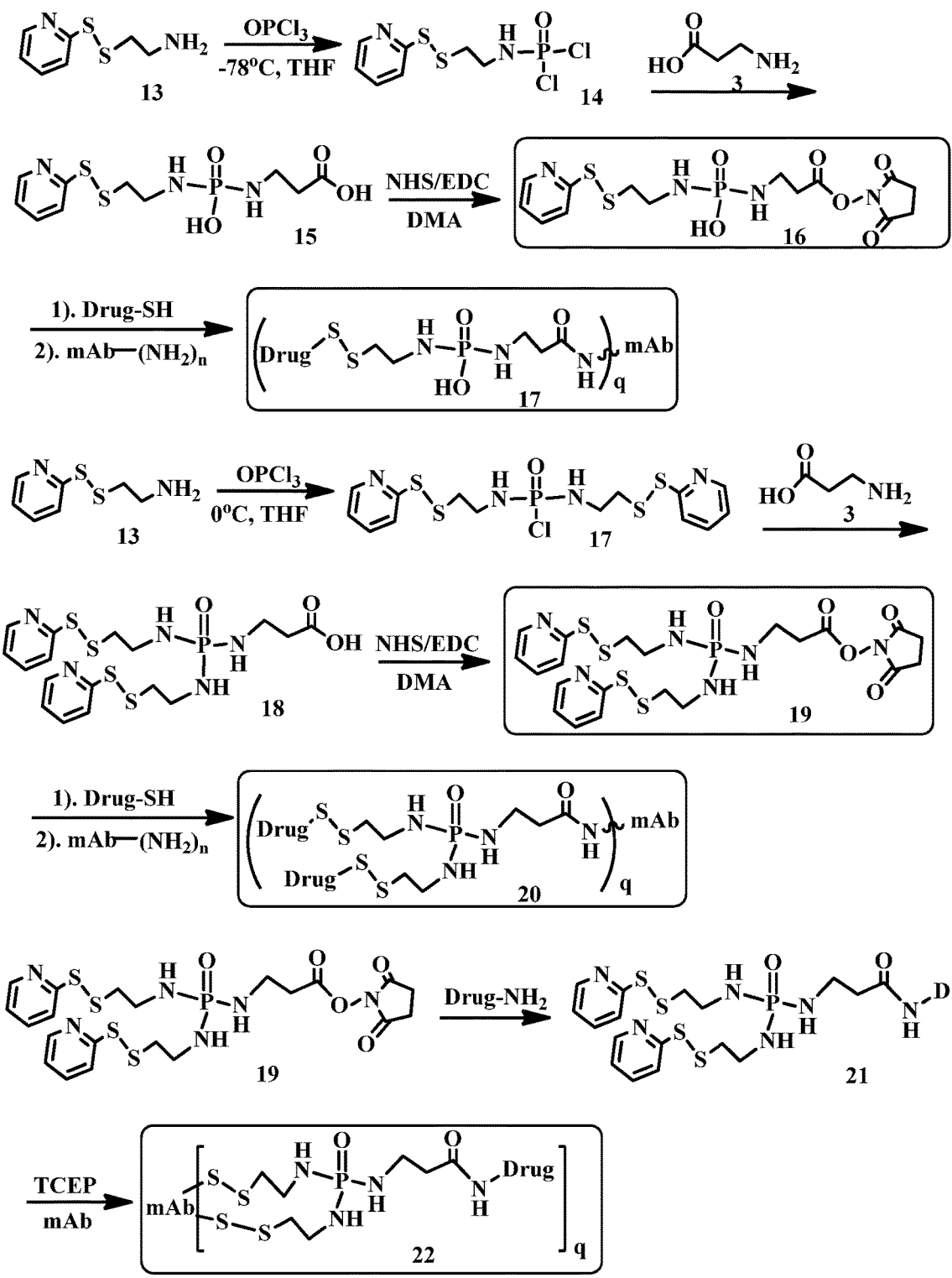
Figure 2. The synthesis of phosphamide linkers containing disulfide bonds and the application of these linkers in the conjugation of an antibody with drugs.

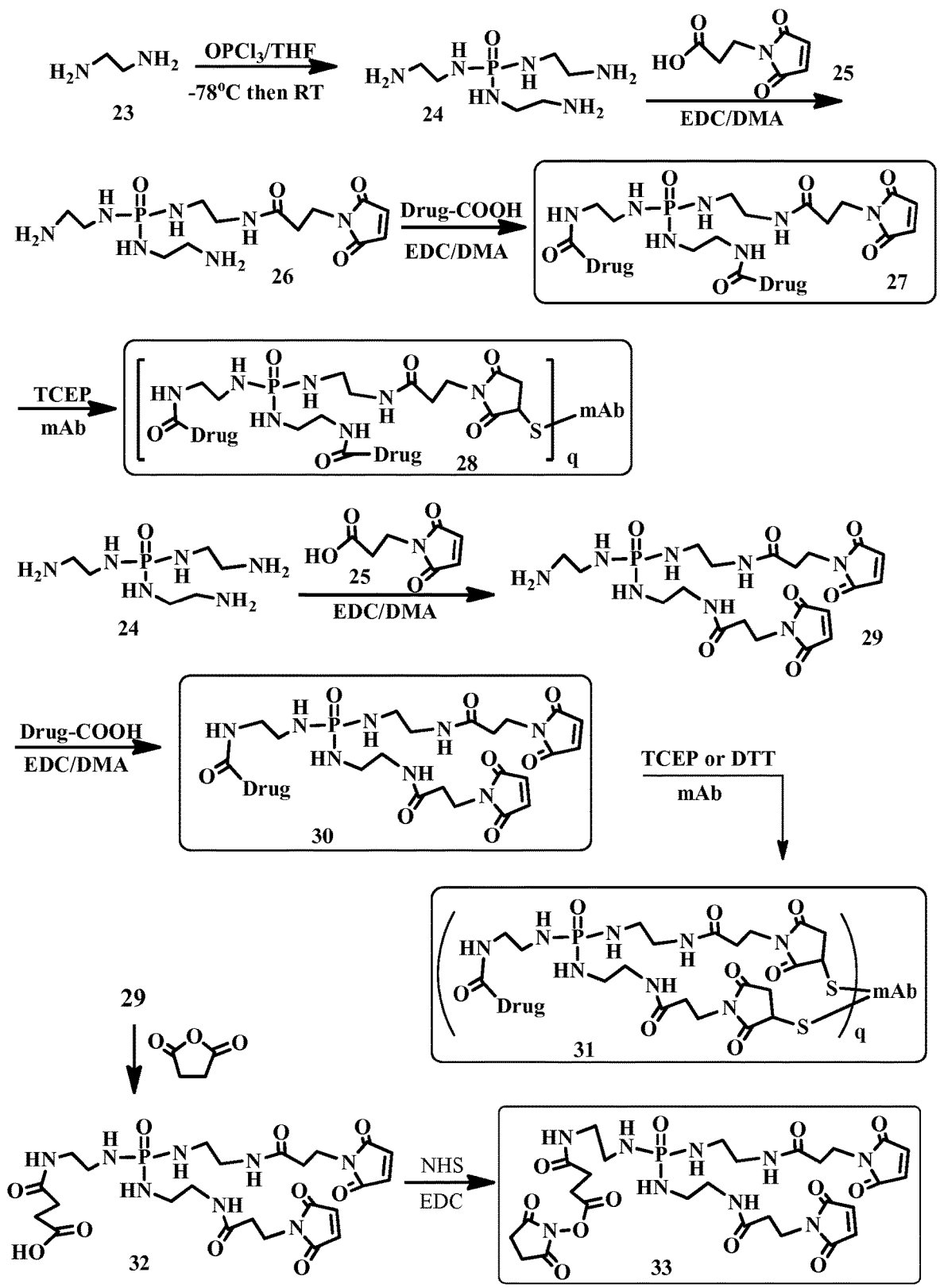
Figure 3. The synthesis of phosphamide linkers containing maleimide groups and the application of these linkers in the conjugation of an antibody with drugs.

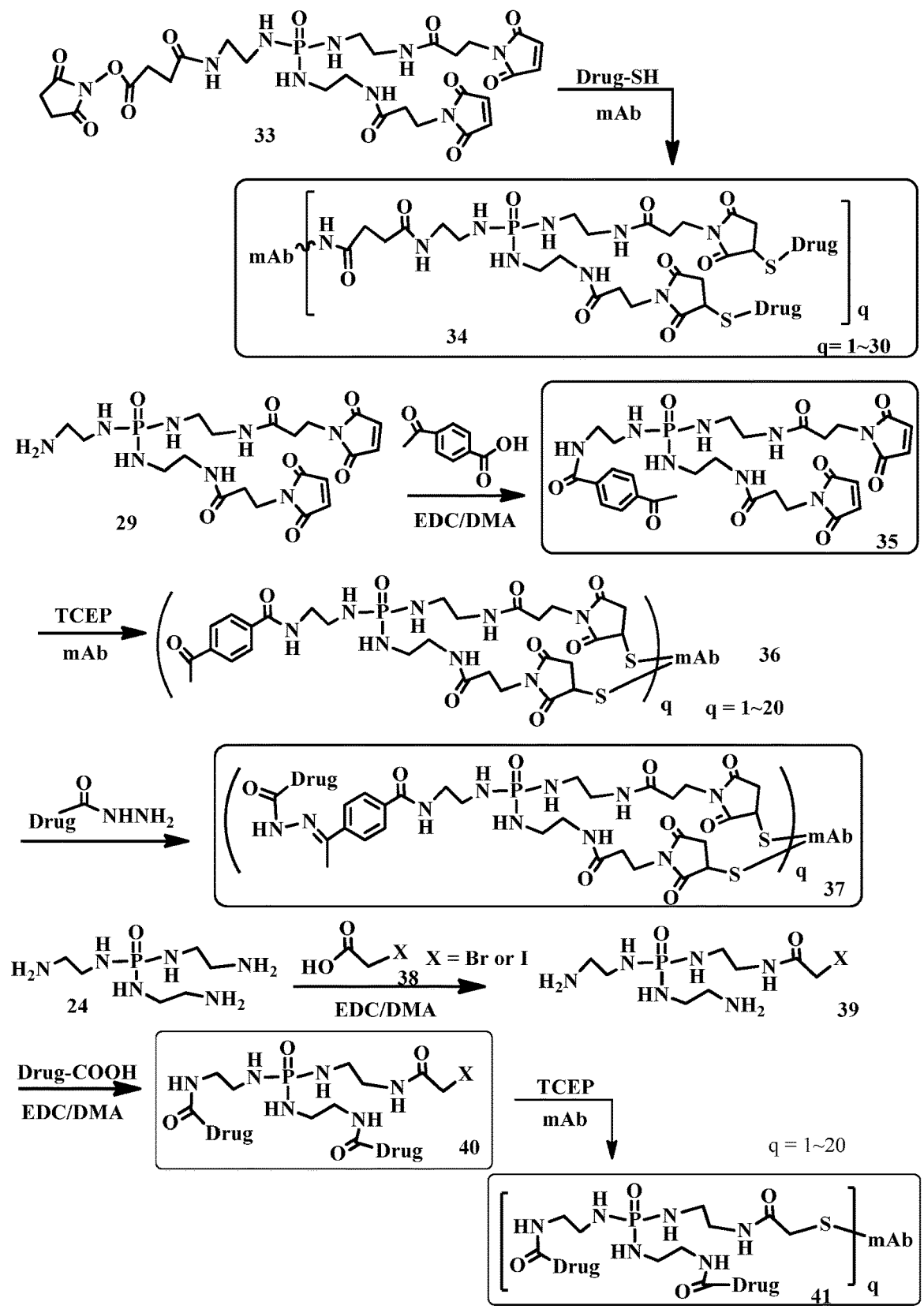
Figure 4. The synthesis of phosphamide linkers containing maleimide, hydrazone, or thioether groups and the application of these linkers in the conjugation of an antibody with drugs.

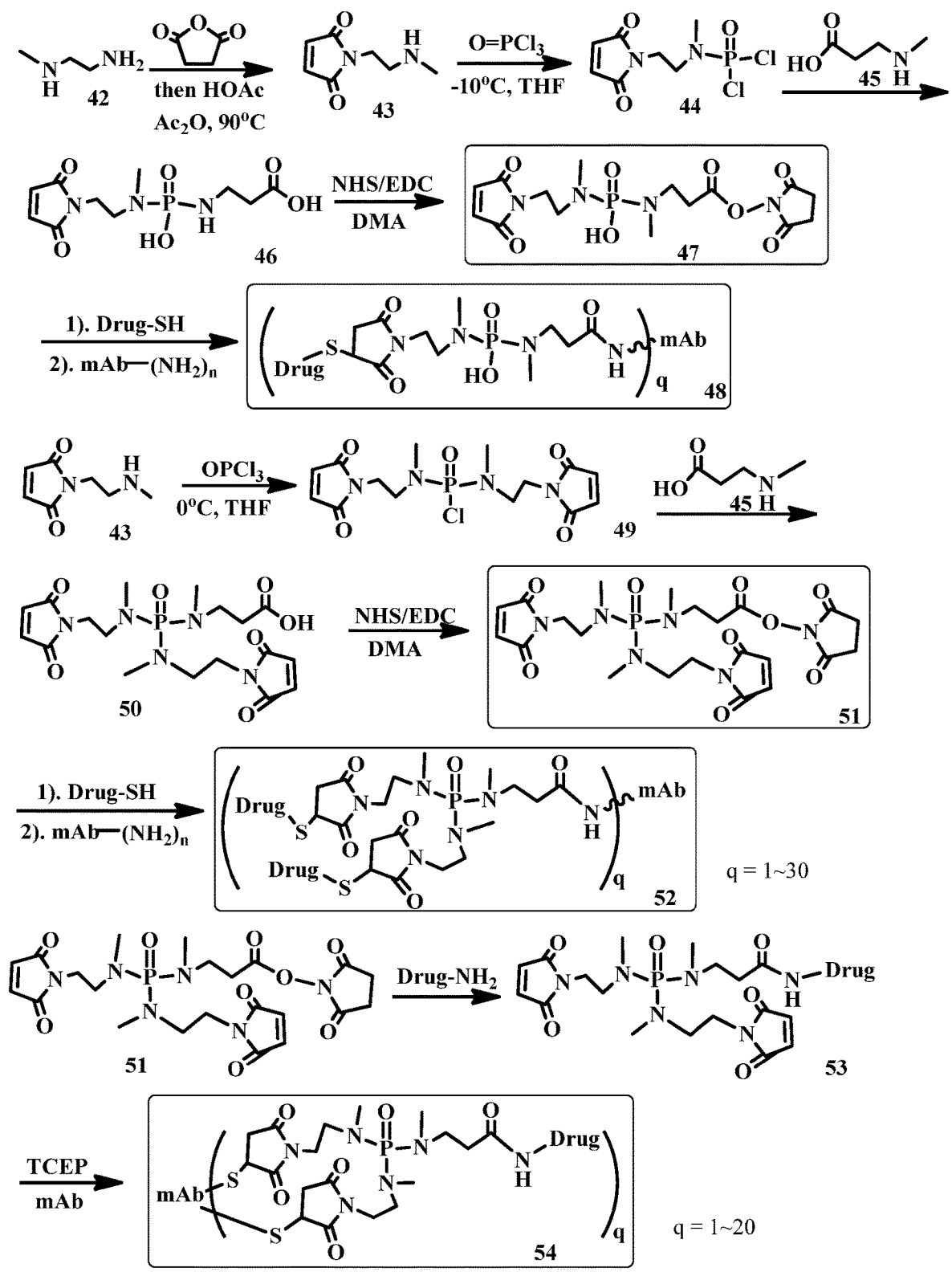
Figure 5. The synthesis of hinder phosphamide linkers containing maleimide groups and the application of these linkers in the conjugation of an antibody with drugs.

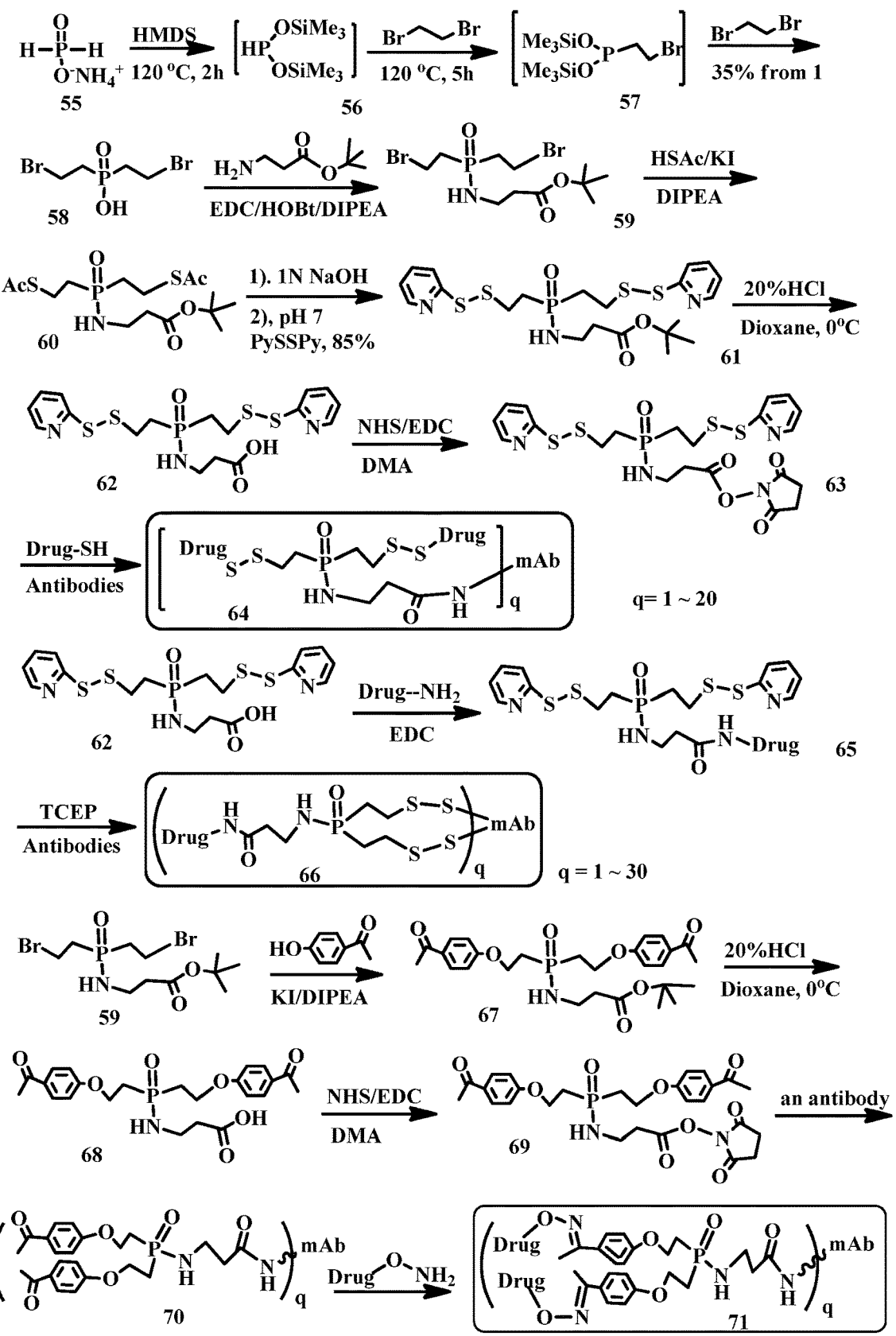
Figure 6. The synthesis of phosphamide linkers containing disulfide or oxime groups and the application of these linkers in the conjugation of an antibody with drugs.

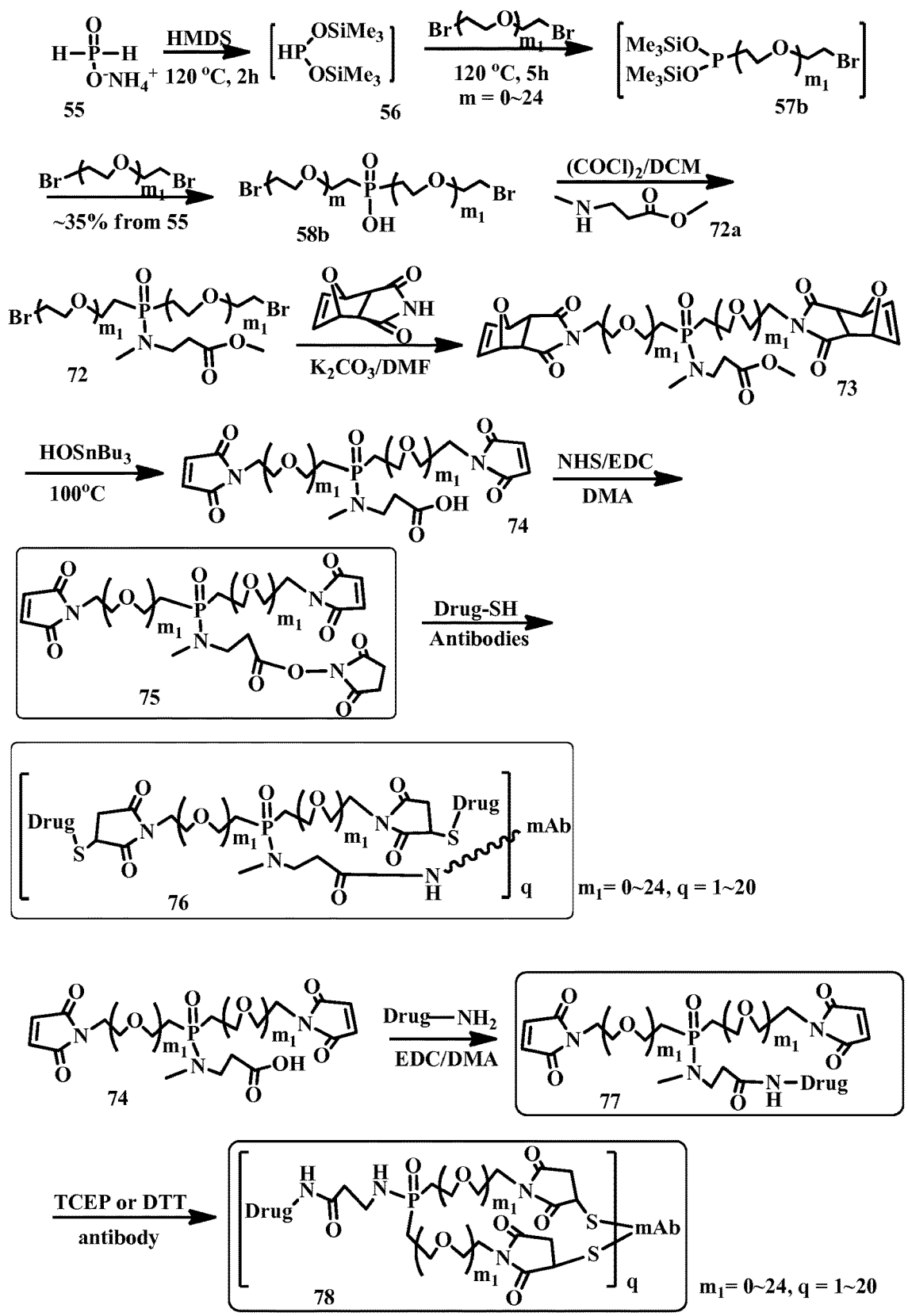
Figure 7. The synthesis of phosphamide linkers containing maleimide and polyethylene glycol groups and the application of these linkers in the conjugation of an antibody with drugs.

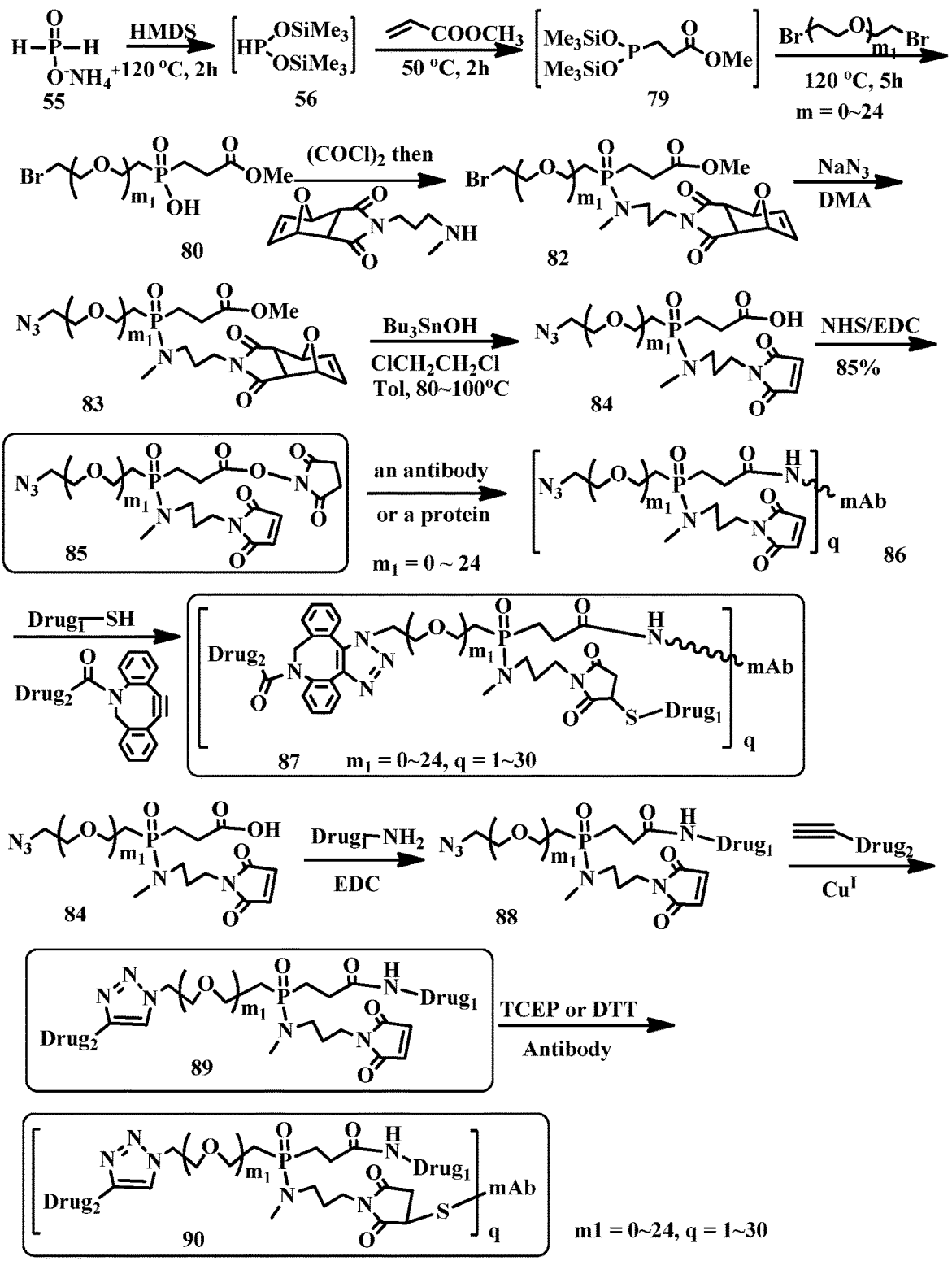

Figure 8. The synthesis of phosphamide linkers containing maleimide, polyethylene glycol and azido groups and the application of these linkers in the conjugation of an antibody with two different compounds. $Drug_1$ and $Drug_2$ here can be a cytotoxic agent for therapeutic application or a chromophore compound for monitoring the interaction with targeted cells.

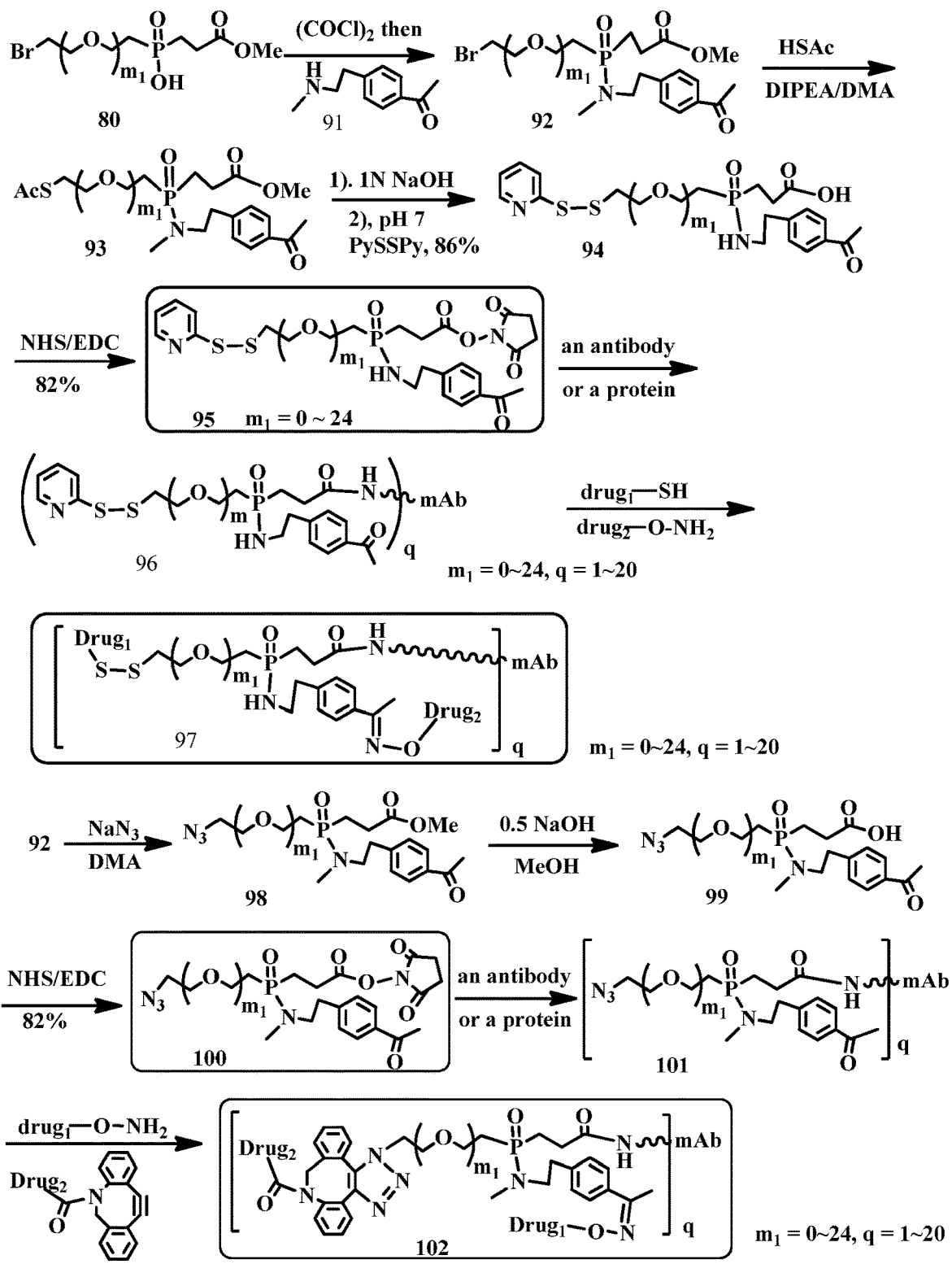

Figure 9. The synthesis of phosphamide linkers containing disulfide, polyethylene glycol or ketone groups, and these linkers are used for conjugation of a protein with two different compounds. $Drug_1$ and $Drug_2$ here can be a cytotoxic agent for therapeutic application or a chromophore compound for monitoring the interaction of the conjugates with targeted cells.

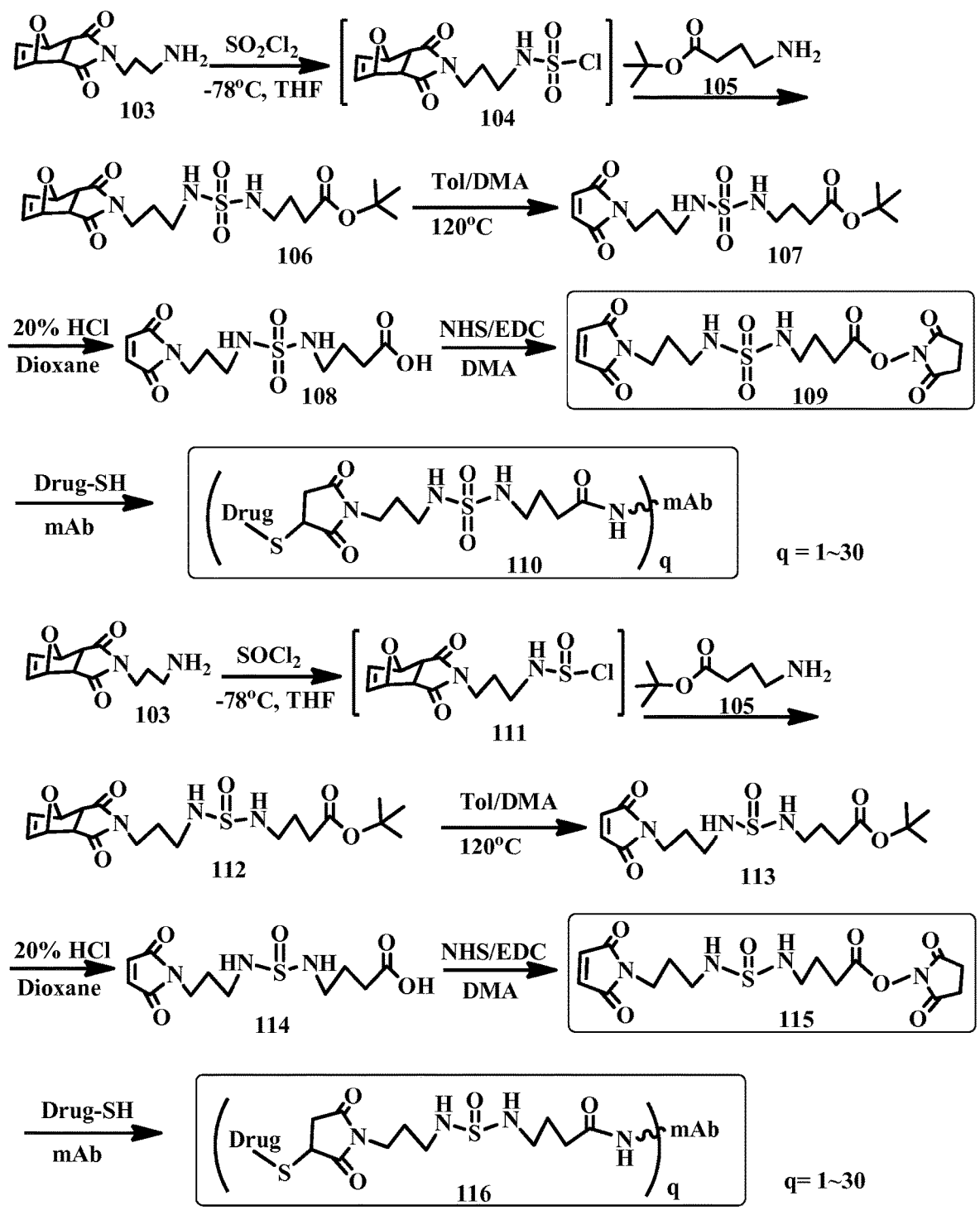
Figure 10. The synthesis of the sulfonamide and the sulfinamide linkers containing a maleimide group and the application of these linkers in the conjugation of an antibody with a cytotoxic drug.

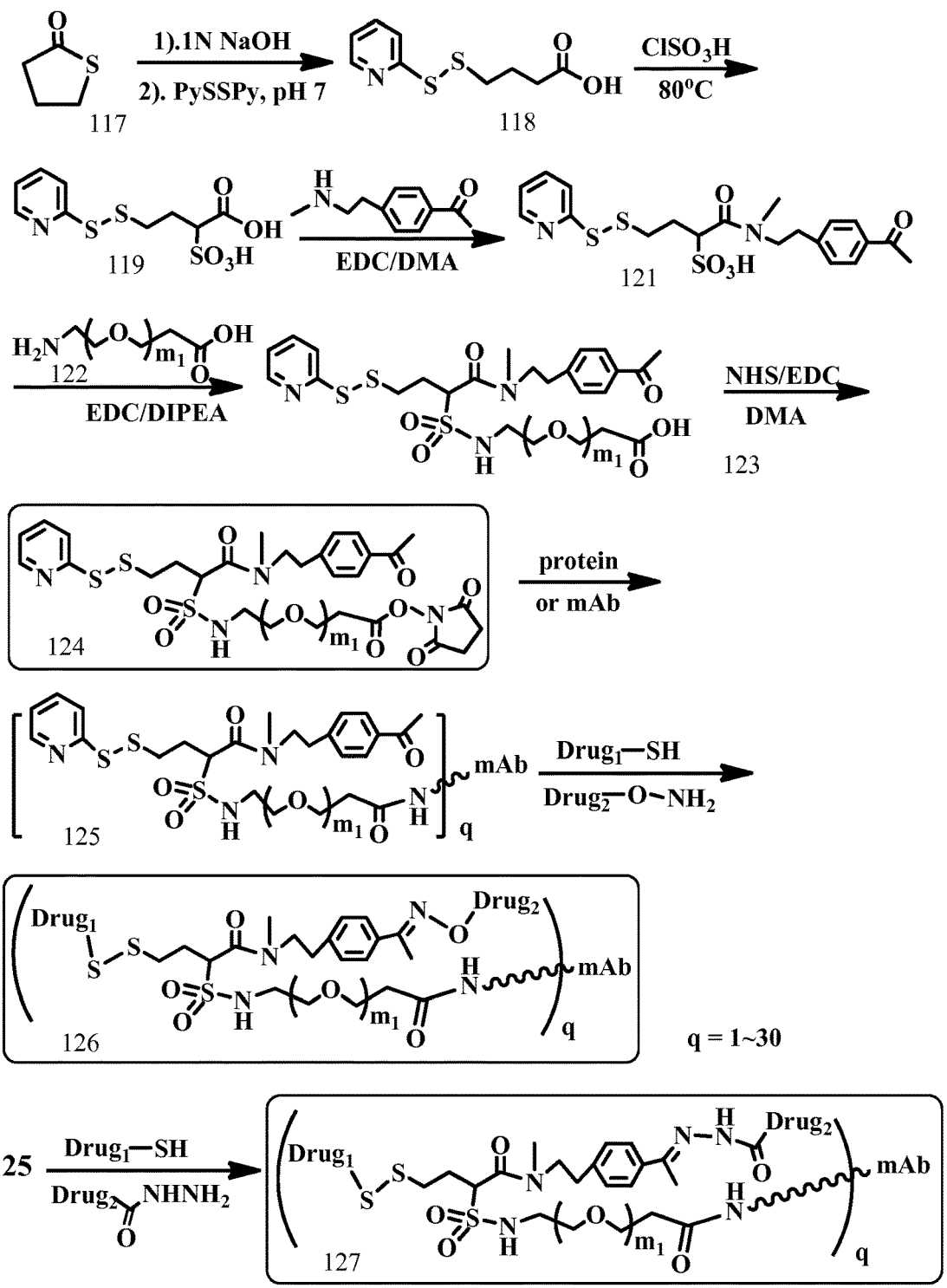

Figure 11. The synthesis of a sulfonamide linker containing a disulfide, polyethylene glycol or ketone group, and the linker is used for conjugation of a protein with two different compounds. $Drug_1$ and $Drug_2$ here can be independently a cytotoxic agent for therapeutic application or a chromophore compound for monitoring the interaction of the conjugate with targeted cells.

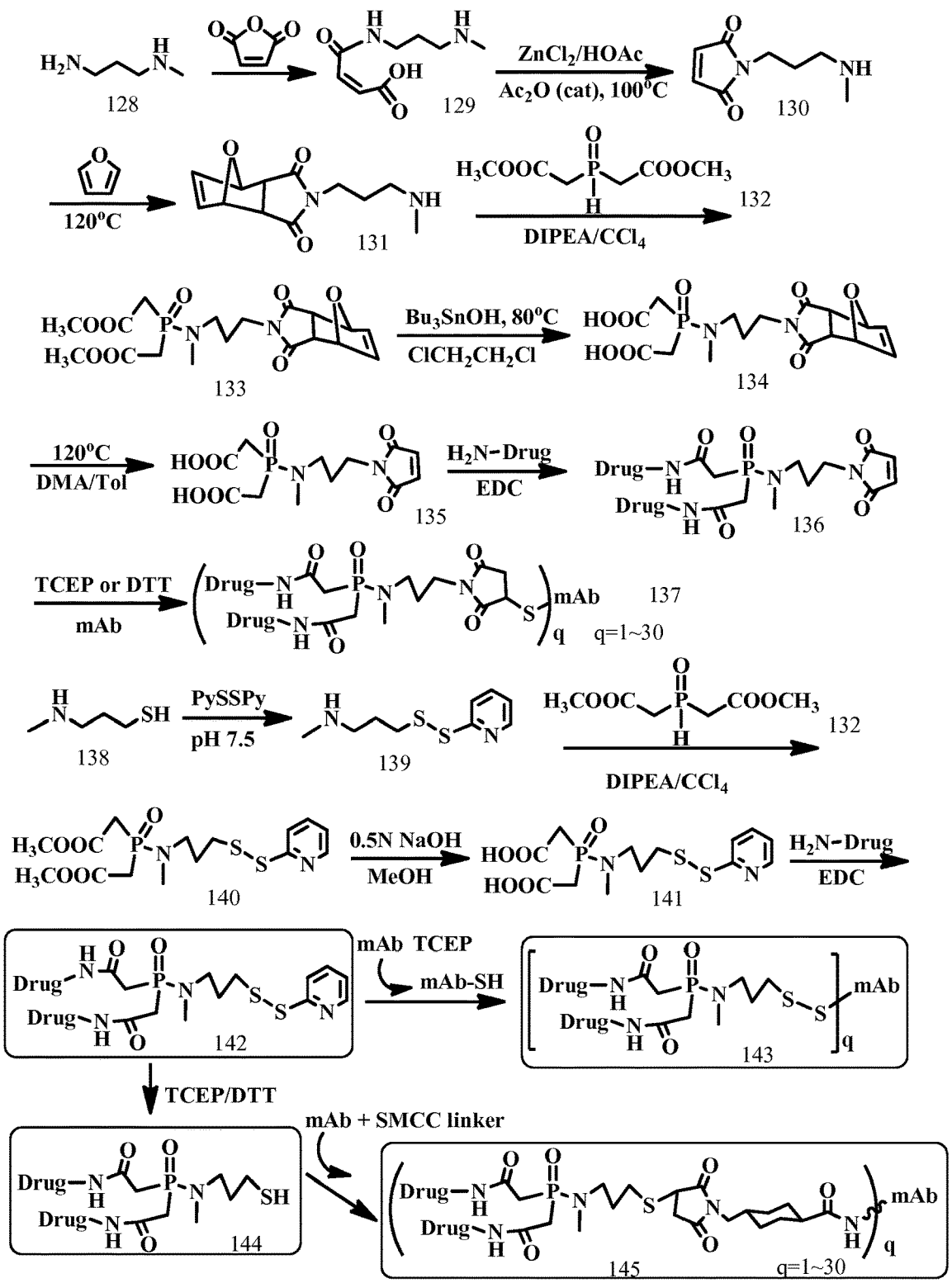
Figure 12. The synthesis of phosphamide linkers containing thioether or disulfide groups, and these linkers are used to link two drug/compounds per linker. Drug here can be a cytotoxic agent for therapeutic application or a chromophore compound for monitoring the interaction of the conjugates with targeted cells.

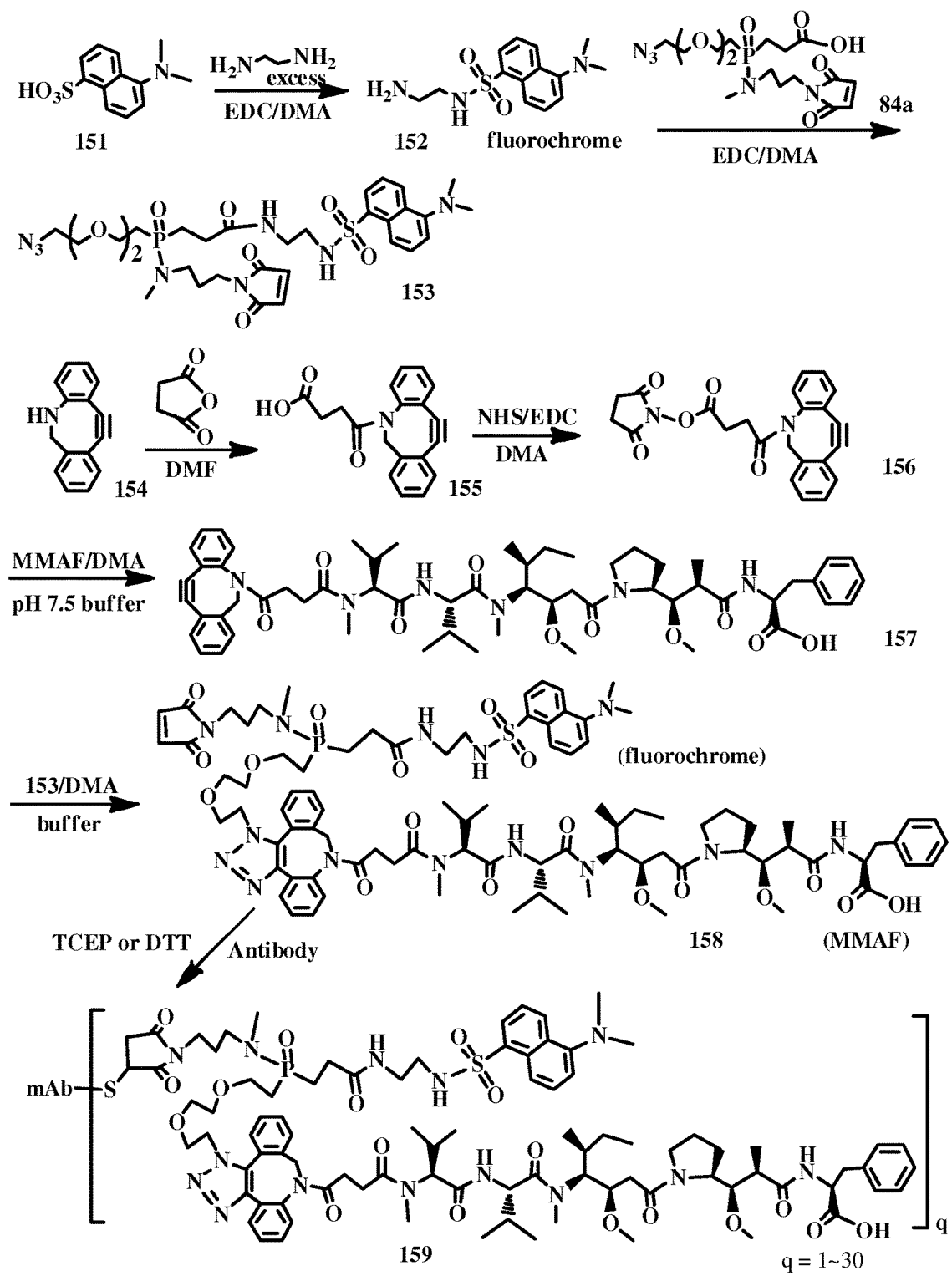
Figure 13. The synthesis of an antibody conjugate via the phosphamide linkers containing two function groups, wherein one group is linked to a cytotoxic agent, MMAF for targeted killing, and the other one is linked to a fluorochrome group for monitoring the interaction of the conjugate with a targeted cell.

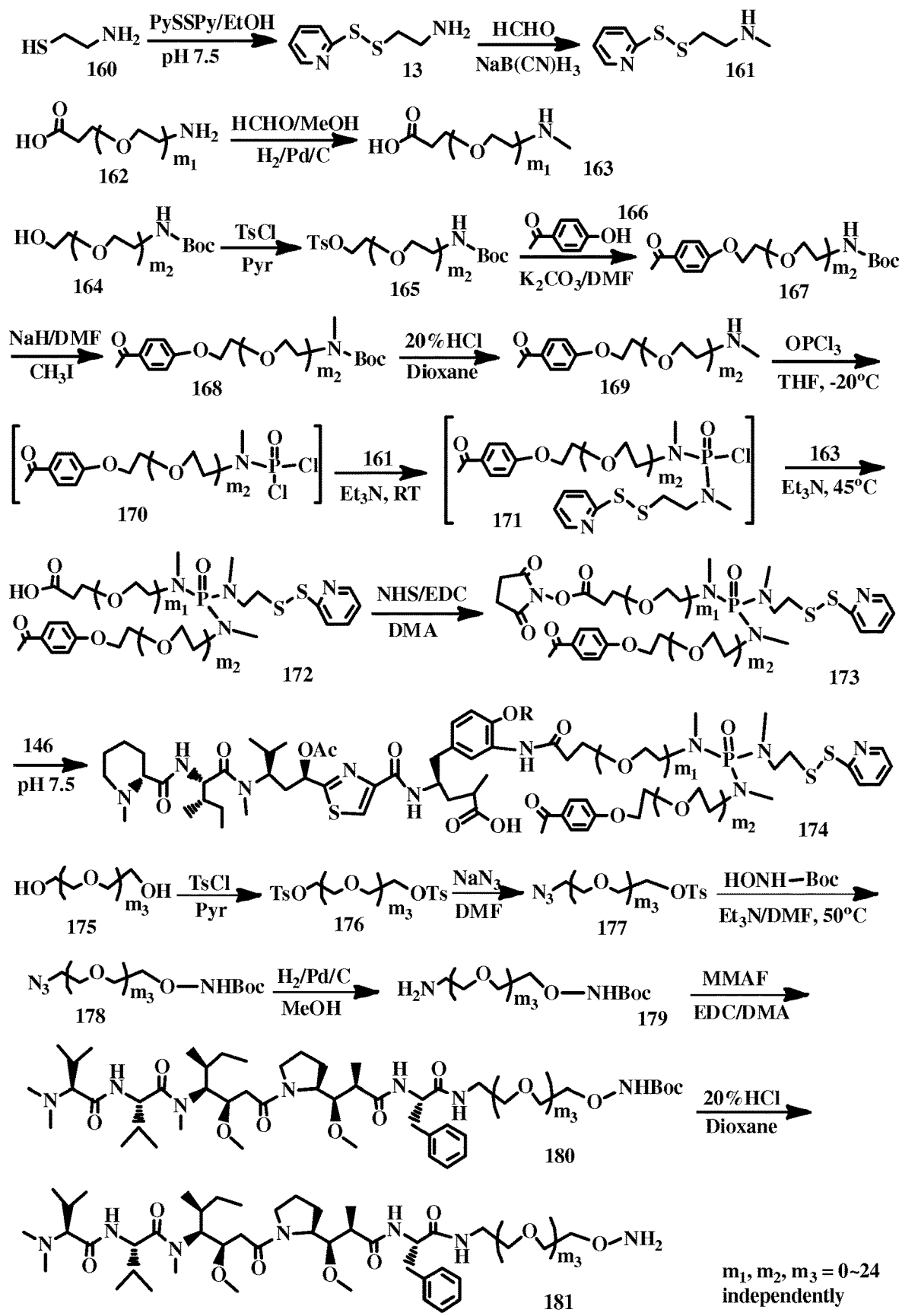
Figure 14. The synthesis of the phosphamide linkers containing two function groups.

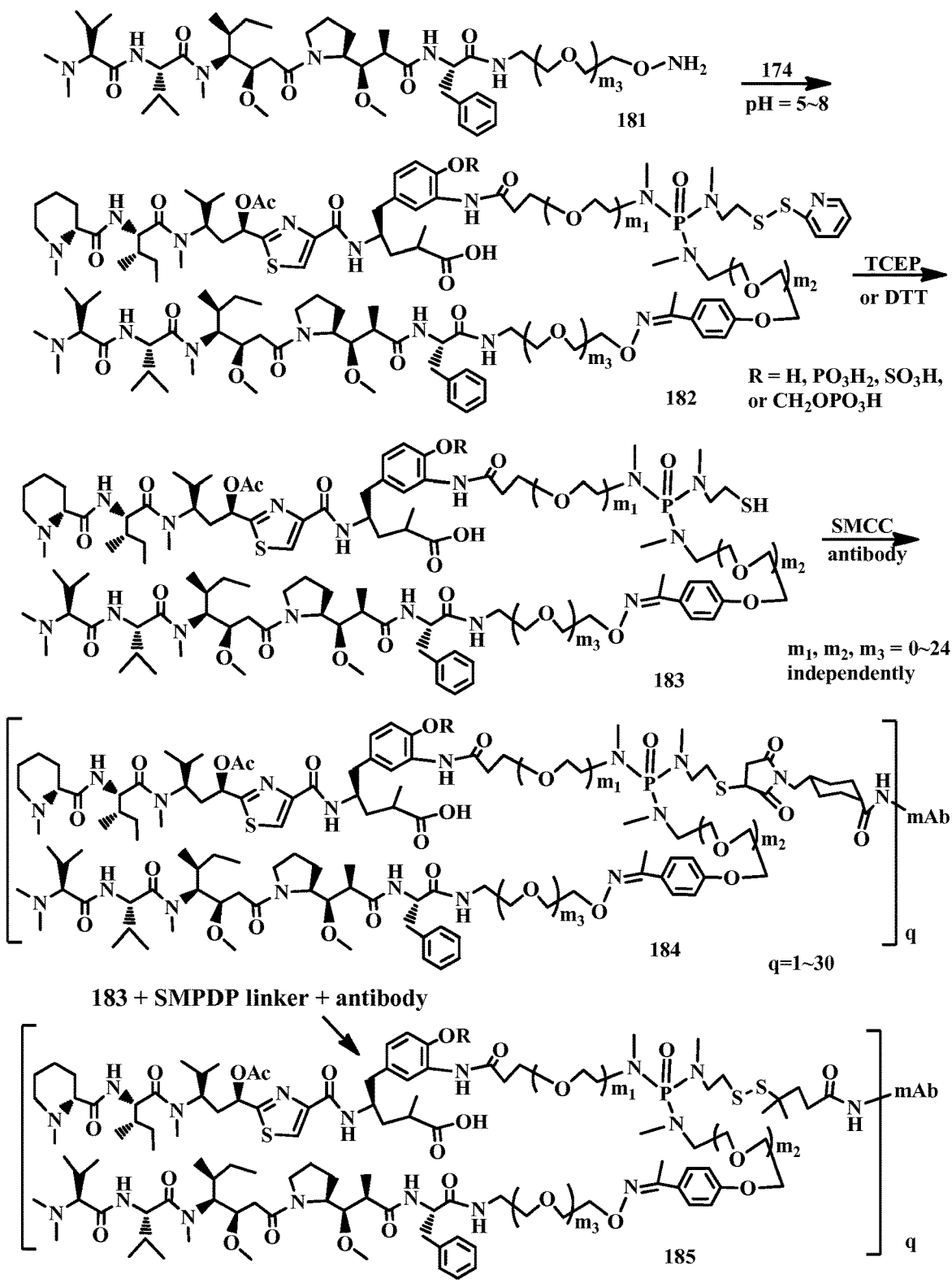
Figure 15. The synthesis of an antibody conjugate via a phosphamide linker containing both a tubulysin analog and a MMAF analog on the linker. Wherein q is 1~30; $m_1$, $m_2$, $m_3$ are 0~24 independently; R is H, $PO_3H_2$, $SO_3H$, or $CH_2OPO_3H_2$.

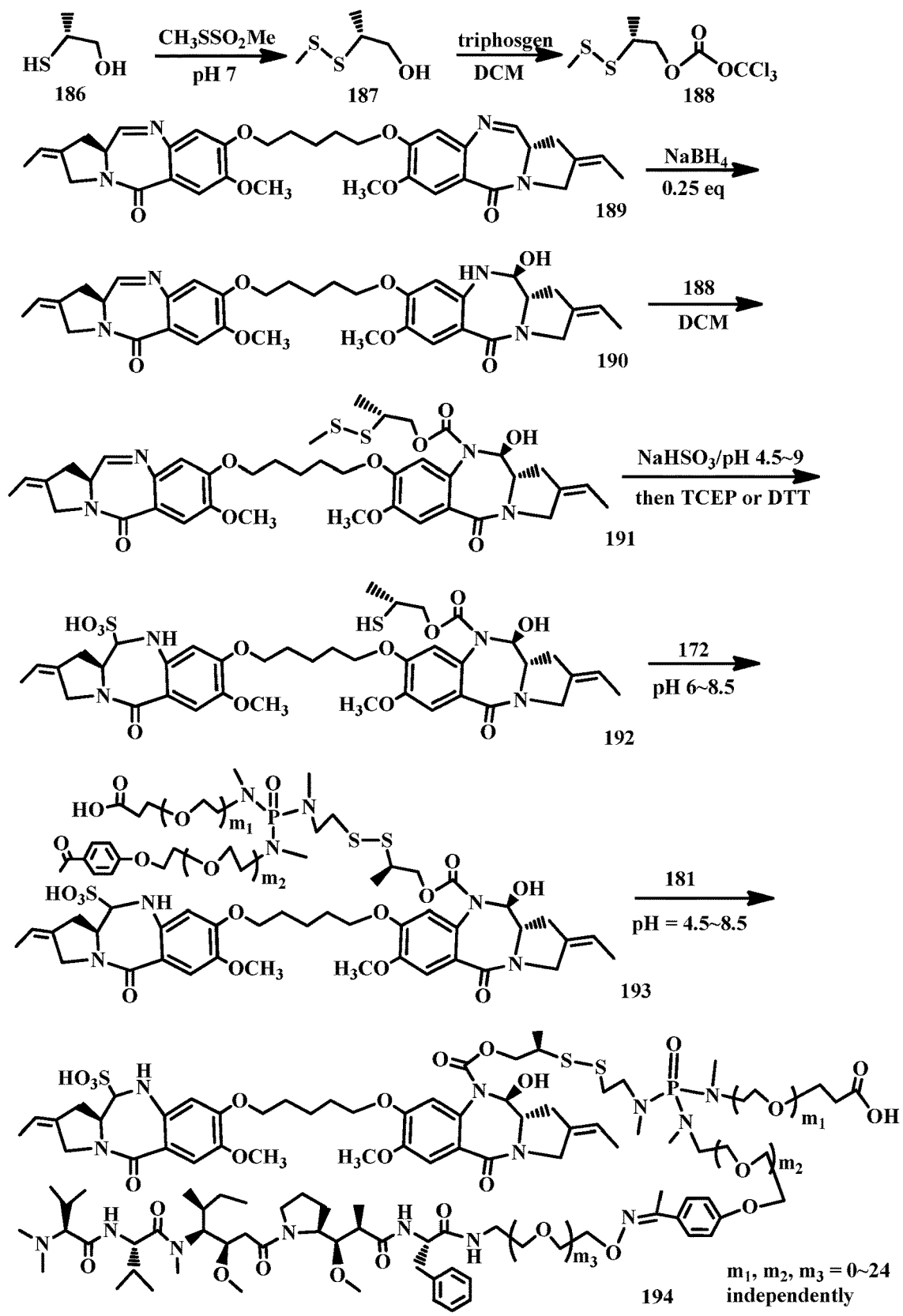
Figure 16. The synthesis of the phosphamide linkers containing two different cytotoxic drugs (PBD dimer & MMAF analogs).

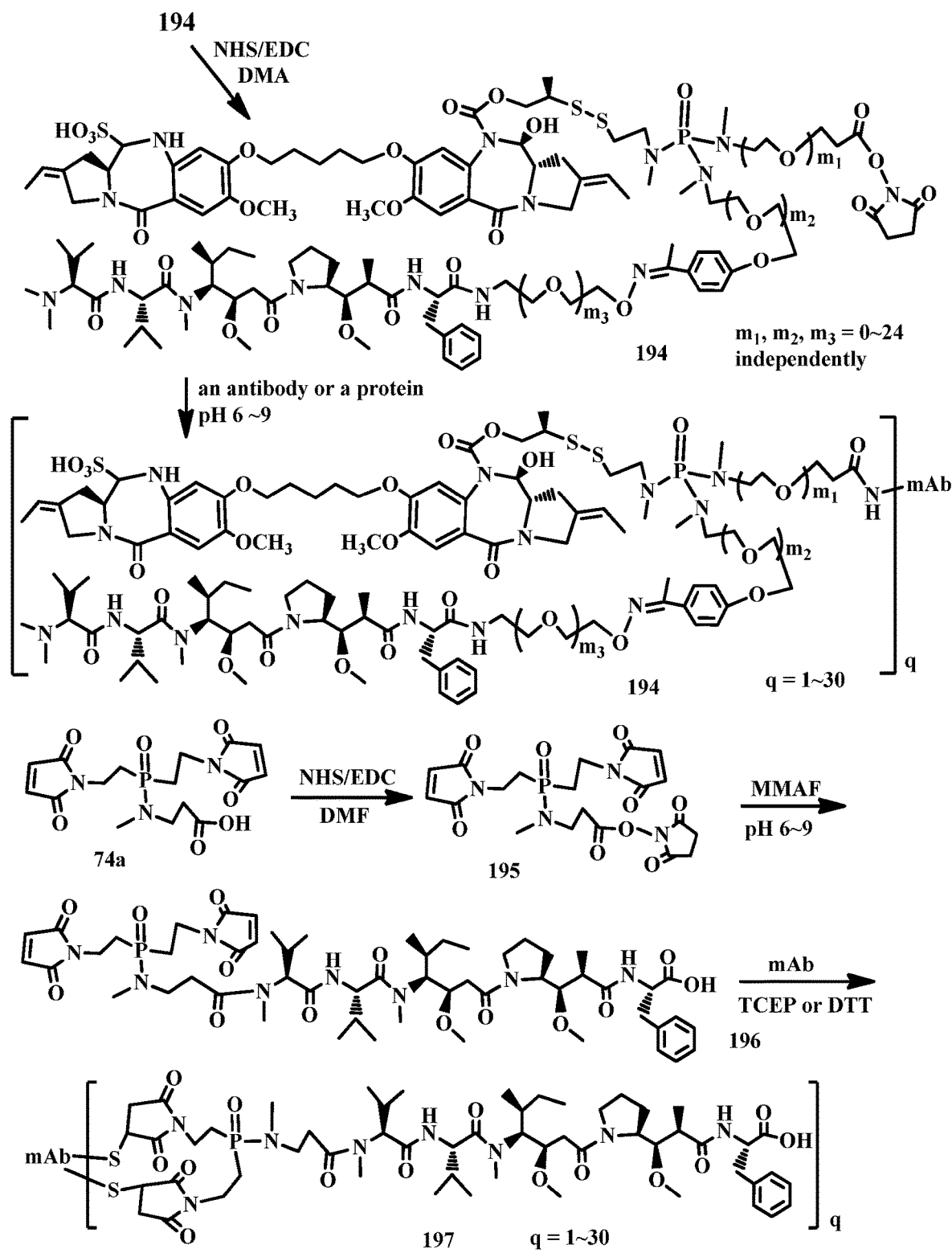
Figure 17. The synthesis of antibody conjugates via the phosphamide linkers of the present patent. The linkers can be conjugated two different drugs (e.g. a PBD analog and a MMAF analog) per linker, or can be linked to a pair of cysteine sites of an antibody.

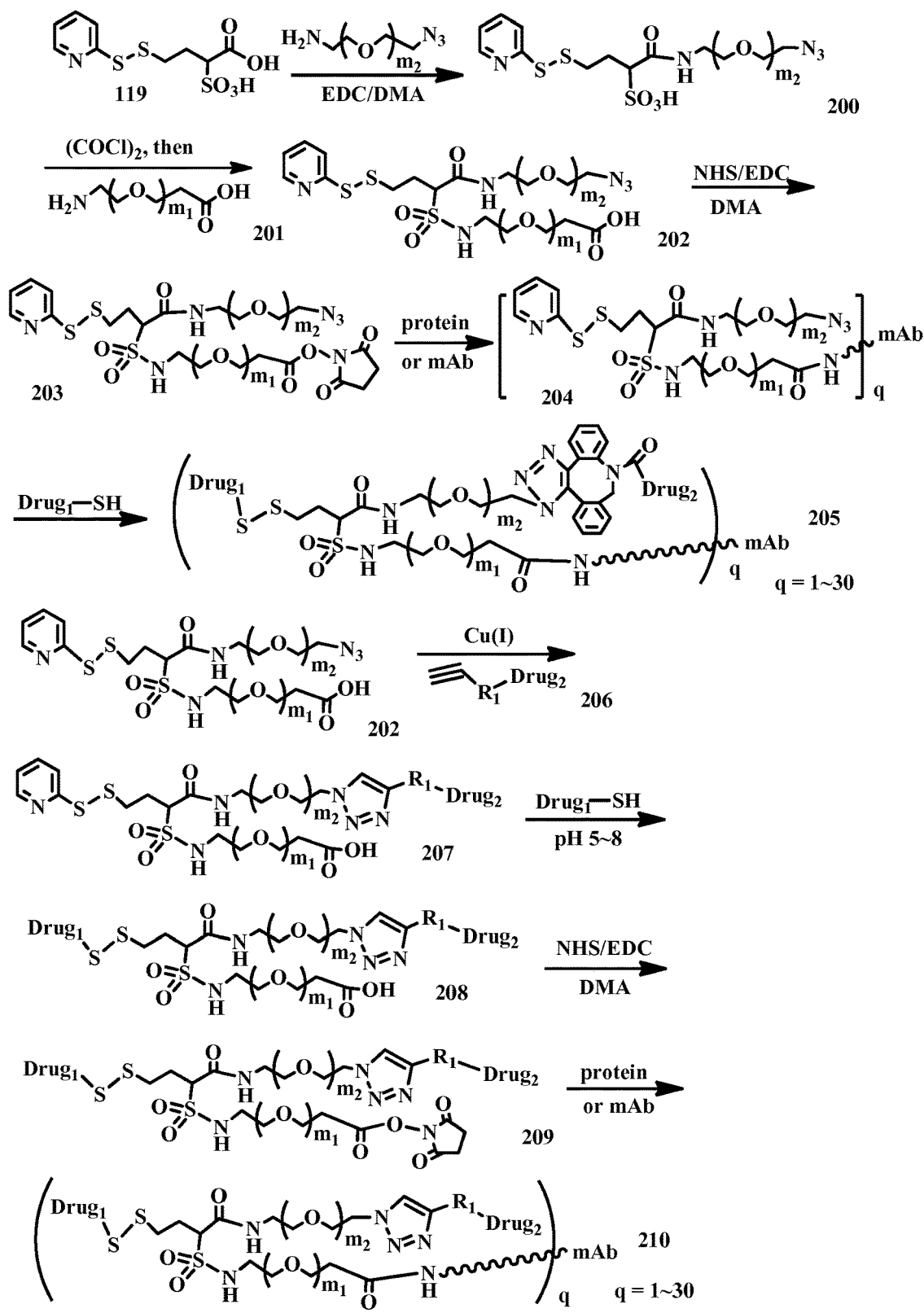
Figure 18. The synthesis of a sulfonamide linker containing a disulfide, polyethylene glycol, azido, or a triazole group, and the linker is for conjugation with two different compounds. . Wherein q is 1~30; $m_1$, $m_2$, $m_3$ are 0~24 independently; $R_1$ is defined in Formula (I).

LINKERS FOR CONJUGATION OF CELL-BINDING MOLECULES

FIELD OF THE INVENTION

The present invention relates to the preparation of hydrophilic linkers used for the conjugation of a drug, in particular, a cytotoxic agent or a chromophore molecule to a cell binding molecule. The present invention also relates to methods of making cell-binding agent-drug (e.g. cytotoxic agent) conjugates comprising either modification of drugs with these hydrophilic linkers first, followed by reaction with cell-binding agents; or modification of cell-binding agents with these hydrophilic linkers first, followed by reaction with drugs.

BACKGROUND OF THE INVENTION

Targeted therapies have been the much focused in the pharmaceutical research and development for many years. They are a cornerstone of "precision medicine" (President Barack Obama, State of the Union Address, Jan. 20, 2015, www.whitehouse.gov/precisionmedicine) that uses specific information about a person's tumor to help diagnose, plan treatment, find out how well treatment is working, or make a prognosis (F. S. Collins, New Engl. J. Med. 2015; 372: 793-795). So far many different targeted therapies have been approved for use in cancer treatment by US FDA, European EMA and Chinese CFDA. These therapies include hormone therapies, signal transduction inhibitors, gene expression modulator, apoptosis inducer, angiogenesis inhibitor, immunotherapies, and toxin delivery molecules. The hormone therapies act by preventing the body from producing the hormones or by interfering with the action of the hormones, which in turn can slow or stop the growth of hormone-sensitive tumors. Signal transduction inhibitors block a cell responds to signals from its environment, in particular, prevent the ability of cancer cells to multiply quickly and invade other tissues. Gene expression modulator can modify the function of proteins that play a role in controlling gene expression. Apoptosis inducers cause cancer cells to undergo a process of controlled cell death. Angiogenesis inhibitors block the growth of new blood vessels to tumors (a process called tumor angiogenesis). Immunotherapies trigger the immune system to destroy cancer cells. Most immunotherapies are monoclonal antibodies that recognize specific molecules on the surface of cancer cells. Toxin delivery molecules use a transport vehicle/method to deliver a toxin drug specifically to the cancer cells.

The much promising approach that has been studied extensively during the past three decades is the toxin delivery molecules. There are several systemic deliveries of chemotherapeutical drugs for targeted treatment of tumor: Heat-activated targeted drug delivery; Tissue-selective drug delivery for cancer using carrier-mediated transport systems; Tumor-activated prodrug therapy for targeted delivery of chemotherapy; Pressure-induced filtration of drug across vessels to tumor; Promoting selective permeation of the anticancer agent into the tumor; Two-step targeting using a bispecific antibody; Site-specific delivery by an antibody conjugate; And light-activation of macromolecules. Many carriers have been studied in different forms or in special formulations for the target delivery of anticancer drugs, such as Albumin-based drug carriers; Carbohydrate-enhanced chemotherapy; Proteins and peptides based drug carriers; Fatty acids as targeting vectors linked to active drugs; Microsphere carriers; Monoclonal antibodies as carriers; Vitamins, e.g. folates as carriers; Nanoparticle carriers; Liposome carriers, e. g. pegylated liposomes (enclosed in a polyethylene glycol bilayer); Polyethylene glycol (PEG) carriers; Single-chain antigen-binding molecule carriers; Polymeric micelle carriers; Lipoprotein-based drug carriers; Dendrimers; etc. Ideally the delivery vehicle has to be site-specific, non-toxic, biocompatible, non-immunogenic, and biodegradable (Scott, R; et al (2008) Expert Opin. Drug Deli. 5, 459) and avoid recognition by the host's defense mechanisms (Saltzman, W.; (2008). "Drug delivery systems" Access Science. McGraw-Hill Co.). For this criterion, using a monoclonal antibody (mAb) as a delivery vehicle for chemotherapeutical drugs has been much successful. By combining the unique targeting capabilities of monoclonal antibodies with the cancer-killing ability of cytotoxic drugs, the antibody-drug conjugates (ADCs) allow sensitive discrimination between healthy and diseased tissue (ADC Review, J. Antibody-drug Conjugates,—Jun. 1, 2013). Beside the successful market approval of ado-trastuzumab emtansine (T-DM) in 2013 and Brentuximab vedotin in 2011 by US FDA, there are over 40 different ADC drugs currently in clinical trials in USA (www.clinicaltrials.gov). But there are still many challenges among ADC development, such as the linker selection for improvement of the therapeutic index, mAbs linked to a careful selection of the targets, a better understanding of the mechanism of action, and the management and understanding of ADC off-target toxicities. It has been known that the linker between the delivery vehicles, in particular, an antibodies and the cell-killing toxins plays a critical role in the development of targeted drug delivery systems, as the nature of the linker significantly affects the potency, selectivity and the pharmacokinetics of the resulting conjugates (Zhao, R. Y. et al (2011) J. Med. Chem. 54, 3606; Acchionea, M. et al (2012) mAbs, 4, 362; Doronina, S. et al, (2006) Bioconjug Chem, 17, 114; Hamann, P. et al. (2005) Bioconjug Chem. 16, 346). So far, four types of linkers had often been used for preparation of cell binding agent-drug conjugates that have entered the clinic: (a) acid-labile linkers, exploiting the acidic endosomal and lysosomal intracellular microenvironment; (b) linkers cleavable by lysosomal proteases; (c) chemically stable thioether linkers that release a lysyl adduct after proteolytic degradation of the antibody inside the cell; and (d) disulfide-containing linkers, which are cleaved upon exposure to an intracellular thiol (Zhao, R. Y. et al, 2011 J. Med. Chem. 36, 5404).

Conjugates of cell-binding agents with drugs or modified chemical compounds via different types of linkers have been described (U.S. Pat. Nos. 4,680,338, 5,122,368, 5,141,648, 5,208,020, 5,416,064; 5,475,092, 5,543,390, 5,563,250 5,585,499, 5,880,270, 6,214,345, 6,436,931, 6,372,738, 6,340,701, 6,989,452, 7,129,261, 7,375,078, 7,498,302, 7,507,420, 7,691,962, 7,910,594, 7,968,586, 7,989,434, 7,994,135, 7,999,083, 8,153,768, 8,236,319, WO2014080251, Zhao, R.; et al, (2011) J. Med. Chem. 36, 5404; Doronina, S.; et al, (2006) Bioconjug Chem, 17, 114; Hamann, P.; et al. (2005) Bioconjug Chem. 16, 346). Typically, in these conjugates, the cell-binding agents are first modified with a bifunctional agent such as SPDP (N-succinimidyl 3-(2-pyridyldithio) propionate), SMPDP (N-succinimidyl 4-methyl-4-(2-pyridyldithio) pentanoate), SPDB (N-succinimidyl 4-(2-pyridyldithio) butanoate), or SMCC (succinimidyl-4-(N-maleimidomethyl) cyclohexane-1-carboxylate), to introduce an active disulfide or a maleimido moiety. Reaction with a thiol-containing cytotoxic drug provides a conjugate in which the cell-binding agent, such as a monoclonal antibody, and drug are linked via disulfide bonds or thioether bonds.

However, the use of the cell binding molecule-drug conjugates, such as antibody-drug conjugates (ADCs), in developing therapies for a wide variety of cancers has been limited both by the availability of specific targeting agents (carriers) as well as the conjugation methodologies which result in the formation of protein aggregates when the amount of the drugs that are conjugated to the carrier (i.e., the drug loading) is increased. Normally the tendency for cytotoxic drug conjugates to aggregate is especially problematic when the conjugation reactions are performed with the hydrophobic linkers. Since higher drug loading increases the inherent potency of the conjugate, it is desirable to have as much drug loaded on the carrier as is consistent with retaining the affinity of the carrier protein. The presence of aggregated protein, which may be nonspecifically toxic and immunogenic, and therefore must be removed for therapeutic applications, makes the scale-up process for the production of these conjugates more difficult and decreases the yield of the products.

We have invented a series of hydrophilic linkers containing phosphinate, sulfonyl, and/or sulfoxide groups which can improve methods for conjugating cytotoxic drugs to a carrier (cell binding molecules) in high a drug loading without aggregation (PCT/IB2012/056700 and PCT/CN2014/072769). Here we describe the extending innovation of the hydrophilic linkers for better conjugation, much conditional drug release, loading with two different kinds of drugs or molecules per a linker, and/or linking with a pair of sites of a cell binding molecule per a linker for specific or better conjugation.

SUMMARY OF THE INVENTION

The present invention provides hydrophilic linkers containing phosphamide, phosphinate, sulfonamide, sulfonyl, sulfonimide, and/or sulfoxide groups to link drugs to a cell-binding agent (e.g., an antibody). The preferred formula of the cell binding molecule—hydrophilic linker—drug conjugates can be represented as: Cb-(-L-Drug)$_n$, wherein Cb is a cell-binding agent, L is a hydrophilic linker, Drug is a drug molecule, and n is an integer from 1 to 20. The advantages in applying the hydrophilic linker in the cell molecule-drug conjugate are: a). Reducing the aggregation of the conjugates in water based media; b). enabling higher drug-per-cell binding molecule-ratio conjugate, resulting in higher potency; c). Being retained inside the target cell after the drug-linker released from the conjugates, which can combat permeability-glycoprotein (Pgp)-expressing multidrug resistant (MDR) cells; d). Enabling loading two different kinds of drugs per a linker; f). Conjugating a pair of sites of a cell binding molecule per a linker.

In one aspect of the present invention, the hydrophilic linker is represented by Formula (I) wherein Y can react with a cell-binding agent and Z can react with a cytotoxic drug:

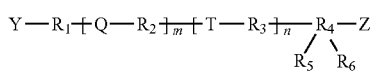

(I)

Wherein:

Y represents a functional group that enables reaction with a cell-binding agent;

Q and T are either —X$_1$—P(=O)(OM)-, or X$_1$—S(O$_2$)—, or —X$_1$—S(O)—; or —X$_1$—P(=O)(OM)-X$_2$—, or —X$_1$—P(=O)[X$_2$—R$_4$—Z]—X$_3$—, or —X$_1$—P(=O)[X$_2$—R$_1$—Y]—X$_3$—, or —X$_1$—S(O$_2$)—X$_2$—, or —X$_1$—S(O)—X$_2$—;

X$_1$, X$_2$ and X$_3$ are independently selected from N(R$_7$), O, or S; In addition, when X$_1$ is either N(R$_7$), or O, or S, then either X$_2$ or X$_3$, or another X$_1$ connects to —P(=O), —S(O), or —S(O$_2$) can be CH$_2$.

m and n are integer from 0 to 5, but not 0 at the same time;

Z represents a functional group that enables linkage of a cytotoxic drug via a disulfide, thioether, thioester, peptide, hydrazone, ether, ester, carbamate, carbonate, amine (secondary, tertiary, or quartary), imine, cycloheteroalkyane, heteroaromatic, alkoxime or amide bond;

R$_1$, R$_2$, R$_3$, R$_4$, R$_5$, R$_6$, and R$_7$ are the same or different and are H, linear alkyl having from 1-6 carbon atoms, branched or cyclic alkyl having from 3 to 6 carbon atoms, linear, branched or cyclic alkenyl or alkynyl, or 1~6 carbon atoms of esters, ether, amide, or polyethyleneoxy unit of formula (OCH$_2$CH$_2$)$_p$, wherein p is an integer from 0 to about 1000, or combination thereof.

Additionally R$_1$, R$_2$, R$_3$ and R$_4$ are respectively a chain of atoms selected from C, N, O, S, Si, and P that covalently connects the cell-surface binding ligand, the phosphinate or sulfonyl group, the conjugated drug and among themselves (R$_1$, R$_2$, R$_3$ and R$_4$). The atoms used in forming the hydrophilic linker may be combined in all chemically relevant ways, such as forming alkylane, alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, peptides, acyloxylamines, hydroxamic acids, or combination thereof.

M is H, or Na, or K, or N$^+$R$_1$R$_2$R$_3$ or a pharmaceutical salt. R$_1$, R$_2$ and R$_3$ are described above.

In another embodiment, when the hydrophilic linkers of the Formula (I) has two or more Y groups, in particular the two same Y groups, at such case, either Q, or/and T is —X$_1$—P(=O)[X$_2$—R$_1$—Y]—X$_3$—, then the hydrophilic linkers of the Formula (I) can be linked to two or more sites, particularly to a pair of sites of cell binding molecules.

In yet another embodiment, when the hydrophilic linkers of the Formula (I) has two Z or more groups, at such case, either Q, or/and T is —X$_1$—P(=O)[X$_2$—R$_4$—Z]—X$_3$—, then the hydrophilic linkers of the Formula (I) can be linked to two or more drugs, in particular, two different drugs.

In another aspect, this invention provides a cell-binding agent-drug conjugate of Formula (II), in which the cell-binding agent, Cb, and the drug, Drug, have reacted at the two ends of the hydrophilic linker:

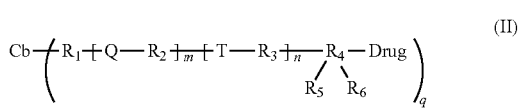

(II)

wherein:

Cb represents a cell-binding agent;

Drug represents the drug linked to the cell-binding agent via the hydrophilic linker by a disulfide, thioether, thioester, peptide, hydrazone, ether, ester, carbamate, carbonate, cycloheteroalkyane, heteroaromatic, alkoxime or amide bond;

q is 1~20; m, n, $R_1$, $R_2$, $R_3$, $R_4$, $R_5$, $R_6$ and M are described the same previously in Formula (I).

Q and T are either $-X_1-P(=O)(OM)-$, or $-X_1-S(O_2)-$, or $-X_1-S(O)-$; or $-X_1-P(=O)(OM)-X_2-$, or $-X_1-P(=O)[X_2-R_4\text{-Drug}]-X_3-$, or $-X_1-P(=O)[X_2-R_1\text{-Cb}]-X_3-$, or $-X_1-S(O_2)-X_2-$, or $-X_1-S(O)-X_2-$;

$X_1$, $X_2$ and $X_3$ are independently selected from $N(R_7)$, O, or S; In addition, when $X_1$ is either $N(R_7)$, or O, or S, then either $X_2$, or $X_3$, or another $X_1$ that connects to $-P(=O)$, $-S(O)$, or $-S(O_2)$ can be $CH_2$.

In a further aspect, the present invention provides a modified cell-binding agent of Formula (III), in which the cell-binding agent, Cb, has reacted with the hydrophilic linker, which still has Z, a group capable of reacting with a drug:

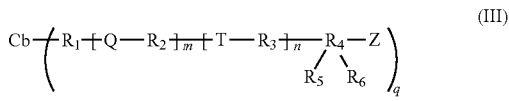

(III)

Wherein Cb, Z, m, n, q, $R_1$, $R_2$, $R_3$, $R_4$, $R_5$ and $R_6$ are defined the same as in Formula (I) and (II).

Q and T are either $-X_1-P(=O)(OM)-$, or $-X_1-S(O_2)-$, or $-X_1-S(O)-$; or $-X_1-P(=O)(OM)-X_2-$, or $-X_1-P(=O)[X_2-R_4-Z]-X_3-$, or $-X_1-P(=O)[X_2-R_1\text{-Cb}]-X_3-$, or $-X_1-S(O_2)-X_2-$, or $-X_1-S(O)-X_2-$;

$X_1$, $X_2$ and $X_3$ are independently selected from $N(R_7)$, O, or S; In addition, when $X_1$ is either $N(R_7)$, or O, or S, then either $X_2$, or $X_3$, or another $X_1$ that connects to $-P(=O)$, $-S(O)$, or $-S(O_2)$ can be $CH_2$.

In an even further aspect, the present invention provides a modified drug of Formula (IV), in which the drug, Drug, has reacted with the hydrophilic linker, which still has Y, a group capable of reacting with the cell-binding agent:

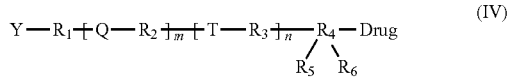

(IV)

Wherein Y, Drug, m, n, q, $R_1$, $R_2$, $R_3$, $R_4$, $R_5$ and $R_6$ are defined the same as in Formula (I) and (II).

Q and T are either $-X_1-P(=O)(OM)-$, or $-X_1-S(O_2)-$, or $-X_1-S(O)-$; or $-X_1-P(=O)(OM)-X_2-$, or $-X_1-P(O)[X_2-R_4\text{-Drug}]-X_3-$, or $-X_1-P(=O)[X_2-R_1-Y]-X_3-$, or $-X_1-S(O_2)-X_2-$, or $-X_1-S(O)-X_2-$;

$X_1$, $X_2$ and $X_3$ are independently selected from $N(R_7)$, O, or S; In addition, when $X_1$ is either $N(R_7)$, or O, or S, then either $X_2$, or $X_3$, or another $X_1$ that connects to $-P(=O)$, $-S(O)$, or $-S(O_2)$ can be $CH_2$.

The present invention further relates to a method of making a cell-binding molecule-drug conjugate of Formula (II), wherein the drug is linked to a cell-binding agent via the hydrophilic linker.

The present invention also relates to a method of making a modified cell-binding molecule of Formula (III), wherein the cell-binding molecule is reacted with the hydrophilic linker.

The present invention also relates to a method of making a modified drug of Formula (IV), wherein the drug is reacted with the hydrophilic linker.

BRIEF DESCRIPTION OF THE DRAWINGS

FIG. 1 shows synthesis of phosphamide linkers containing maleimide groups and the application of these linkers in the conjugation of an antibody with drugs.

FIG. 2 shows the synthesis of phosphamide linkers containing disulfide bonds and the application of these linkers in the conjugation of an antibody with drugs.

FIG. 3 shows the synthesis of phosphamide linkers containing maleimide groups and the application of these linkers in the conjugation of an antibody with drugs.

FIG. 4 shows the synthesis of phosphamide linkers containing maleimide, hydrazone, or thioether groups and the application of these linkers in the conjugation of an antibody with drugs.

FIG. 5 shows the synthesis of hinder phosphamide linkers containing maleimide groups and the application of these linkers in the conjugation of an antibody with drugs.

FIG. 6 shows the synthesis of phosphamide linkers containing disulfide or oxime groups and the application of these linkers in the conjugation of an antibody with drugs.

FIG. 7 shows the synthesis of phosphamide linkers containing maleimide and polyethylene glycol groups and the application of these linkers in the conjugation of an antibody with drugs.

FIG. 8 shows the synthesis of phosphamide linkers containing maleimide, polyethylene glycol and azido groups and the application of these linkers in the conjugation of an antibody with two different compounds. $Drug_1$ and $Drug_2$ here can be a cytotoxic agent for therapeutic application or a chromophore compound for monitoring the interaction of the conjugates with targeted cells as well.

FIG. 9 shows the synthesis of phosphamide linkers containing disulfide, polyethylene glycol or ketone groups, and these linkers are used for conjugation of a protein with two different compounds. $Drug_1$ and $Drug_2$ here can be a cytotoxic agent for therapeutic application or a chromophore compound for monitoring the interaction of the conjugates with targeted cells.

FIG. 10 shows the synthesis of the sulfonamide and the sulfinamide linkers containing a maleimide group and the application of these linkers in the conjugation of an antibody with a cytotoxic drug.

FIG. 11 shows the synthesis of a sulfonamide linker containing a disulfide, polyethylene glycol or ketone group, and the linker is used for conjugation of a protein with two different compounds. $Drug_1$ and $Drug_2$ here can be a cytotoxic agent for therapeutic application or a chromophore compound for monitoring the interaction of the conjugate with targeted cells.

FIG. 12 shows the synthesis of phosphamide linkers containing thioether or disulfide groups, and these linkers are used to link two drug/compounds per linker. Drug here can be a cytotoxic agent for therapeutic application or a chromophore compound for monitoring the interaction of the conjugates with targeted cells.

FIG. 13 shows the synthesis of an antibody conjugate via the phosphamide linkers containing two function groups, wherein one group is linked to a cytotoxic agent, MMAF for targeted killing, and the other one is linked to a fluorochrome group for monitoring the interaction of the conjugate with a targeted cell.

FIG. 14 shows the synthesis of the phosphamide linkers containing two function groups.

FIG. 15 shows the synthesis of an antibody conjugate via a phosphamide linker containing both a tubulysin analog and a MMAF analog on the linker.

FIG. 16 shows the synthesis of the phosphamide linkers containing two different cytotoxic drugs (PBD dimer & MMAF analogs).

FIG. 17 shows the synthesis of antibody conjugates via the phosphamide linkers of the present patent. The linkers can be conjugated two different drugs (e.g. a PBD analog and a MMAF analog) per linker, or can be linked to a pair of cysteine sites of an antibody.

FIG. 18 shows the synthesis of a sulfonamide linker containing a disulfide, polyethylene glycol, azido, or a triazole group, and the linker is for conjugation with two different compounds.

DETAILED DESCRIPTION OF THE INVENTION

Definitions

"Alkyl" refers to an aliphatic hydrocarbon group which may be straight or branched having 1 to 8 carbon atoms in the chain. "Branched" means that one or more lower C numbers of alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl, cyclohexyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methyl-hexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —SR', —S(O)$_2$R', —S(O)R', —OH, -halogen, —N$_3$, —NH$_2$, —NH(R'), —N(R')$_2$ and —CN; where each R' is independently selected from —$C_1$-$C_8$ alkyl and aryl. "Halogen" refers to fluorine, chlorine, bromine or iodine atom; preferably fluorine and chlorine atom.

"Heteroalkyl" refers to $C_2$-$C_8$ alkyl in which one to four carbon atoms are independently replaced with a heteroatom from the group consisting of O, S and N.

"Carbocycle" refers to a saturated or unsaturated ring having 3 to 8 carbon atoms as a monocycle or 7 to 13 carbon atoms as a bicycle. Monocyclic carbocycles have 3 to 6 ring atoms, more typically 5 or 6 ring atoms. Bicyclic carbocycles have 7 to 12 ring atoms, arranged as a bicycle [4,5], [5,5], [5,6] or [6,6] system, or 9 or 10 ring atoms arranged as a bicycle [5,6] or [6,6] system. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl.

A "$C_3$-$C_8$ carbocycle" refers to a 3-, 4-, 5-, 6-, 7- or 8-membered saturated or unsaturated nonaromatic carbocyclic ring. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —SR', —S(O)R', —S(O)$_2$R', —OH, -halogen, —N$_3$, —NH$_2$, —NH(R'), —N(R')$_2$ and —CN; where each R' is independently selected from —$C_1$-$C_8$ alkyl and aryl.

"Alkenyl" refers to an aliphatic hydrocarbon group containing a carbon-carbon double bond which may be straight or branched having 2 to 8 carbon atoms in the chain. Exemplary alkenyl groups include ethenyl, propenyl, n-butenyl, i-butenyl, 3-methylbut-2-enyl, n-pentenyl, hexylenyl, heptenyl, octenyl.

"Alkynyl" refers to an aliphatic hydrocarbon group containing a carbon-carbon triple bond which may be straight or branched having 2 to 8 carbon atoms in the chain. Exemplary alkynyl groups include ethynyl, propynyl, n-butynyl, 2-butynyl, 3-methylbutynyl, 5-pentynyl, n-pentynyl, hexylynyl, heptynyl, and octynyl.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—), 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene, propargyl and 4-pentynyl.

"Aryl" or Ar refers to an aromatic or hetero aromatic group, composed of one or several rings, comprising three to fourteen carbon atoms, preferentially six to ten carbon atoms. The term of "hetero aromatic group" refers one or several carbon on aromatic group, preferentially one, two, three or four carbon atoms are replaced by O, N, Si, Se, P or S, preferentially by O, S, and N. The term aryl or Ar also refers to an aromatic group, wherein one or several H atoms are replaced independently by —R', -halogen, —OR', or —SR', —NR'R", —N=NR', —N=R', —NR'R", —NO$_2$, —S(O)R', —S(O)$_2$R', —S(O)$_2$OR', —OS(O)$_2$OR', —PR'R", —P(O)R'R", —P(OR')(OR"), —P(O)(OR')(OR") or —OP(O)(OR')(OR") wherein R', R" are independently H, alkyl, alkenyl, alkynyl, heteroalkyl, aryl, arylalkyl, carbonyl, or pharmaceutical salts.

"Heterocycle" refers to a ring system in which one to four of the ring carbon atoms are independently replaced with a heteroatom from the group of O, N, S, Se, B, Si and P. Preferable heteroatoms are O, N and S. Heterocycles are also described in The Handbook of Chemistry and Physics, 78th Edition, CRC Press, Inc., 1997-1998, p. 225 to 226, the disclosure of which is hereby incorporated by reference. Preferred nonaromatic heterocyclic include, but are not limited to epoxy, aziridinyl, thiiranyl, pyrrolidinyl, pyrazolidinyl, imidazolidinyl, oxiranyl, tetrahydrofuranyl, dioxolanyl, tetrahydropyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydropyridyl, dihydropyridyl, tetrahydropyrinidinyl, dihydrothiopyranyl, azepanyl, as well as the fused systems resulting from the condensation with a phenyl group.

The term "heteroaryl" or aromatic heterocycles refers to a 5 to 14, preferably 5 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocyclic" and the like refer also to the corresponding "alkylene", "cycloalkylene", "alkenylene", "alkynylene", "arylene", "heteroarylene", "heterocyclene" and the likes which are formed by the removal of two hydrogen atoms.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

"Heteroarylalkyl" refers to an acyclic alkyl radical in which one of the hydrogen atoms bonded to a carbon atom, typically a terminal or sp$^3$ carbon atom, is replaced with a heteroaryl radical. Typical heteroarylalkyl groups include, but are not limited to, 2-benzimidazolylmethyl, 2-furylethyl and the like.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropylsilyl ether, t-butyldimethylsilyl ether, triphenylmethylsilyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, but are not limited to, a halide (e.g., chloride, bromide, and iodide), methanesulfonyl (mesyl), p-toluenesulfonyl (tosyl), trifluoromethylsulfonyl (triflate), and trifluoromethylsulfonate.

The following abbreviations may be used herein and have the indicated definitions: Boc, tert-butoxy carbonyl; BroP, bromotrispyrrolidinophosphonium hexafluorophosphate; CDI, 1,1'-carbonyldiimidazole; DCC, dicyclohexylcarbodiimide; DCM, dichloromethane; DIAD, diisopropylazodicarboxylate; DIBAL-H, diisobutylaluminium hydride; DIPEA, diisopropylethylamine; DEPC, diethyl phosphorocyanidate; DMA, N,N-dimethyl acetamide; DMAP, 4-(N,N-dimethylamino)pyridine; DMF, N,N-dimethylformamide; DMSO, dimethylsulfoxide; DTT, dithiotheritol; EDC, 1-(3-dimethylaminopropyl)-3-ethylcarbodiimide hydrochloride; ESI-MS, electospray mass spectrometry; HATU, O-(7-azabenzotriazol-1-yl)-N,N,N',N'-tetramethyluronium hexafluorophosphate; HOBt, 1-hydroxybenzotriazole; HPLC, high pressure liquid chromatography; NHS, N-Hydroxysuccinimide; MMP, 4-methylmorpholine; PAB, p-aminobeznyl; PBS, phosphate-buffered saline (pH 7.0~7.5); PEG, polyethylene glycol; SEC, size-exclusion chromatography; TCEP, tris(2-carboxyethyl)phosphine; TFA, trifluoroacetic acid; THF, tetrahydrofuran; Val, valine.

"Pharmaceutically" or "pharmaceutically acceptable" refer to molecular entities and compositions that do not produce an adverse, allergic or other untoward reaction when administered to an animal, or a human, as appropriate.

"Pharmaceutically acceptable solvate" or "solvate" refer to an association of one or more solvent molecules and a disclosed compound. Examples of solvents that form pharmaceutically acceptable solvates include, but are not limited to, water, isopropanol, ethanol, methanol, DMSO, ethyl acetate, acetic acid and ethanolamine.

"Pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

As used herein, "pharmaceutical salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutical salts of the present invention can be synthesized from the parent compound which contains a basic or acidic moiety by conventional chemical methods. Generally, such salts can be prepared via reaction the free acidic or basic forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418, the disclosure of which is hereby incorporated by reference.

The novel conjugates disclosed herein use the hydrophilic linkers. Examples of some suitable linkers and their synthesis are shown in FIGS. 1 to 17.

The Hydrophilic Linkers

The synthetic routes to produce hydrophilic linkers as well as the preparation of the conjugates of drugs to a cell binding molecules of the present invention are shown in FIGS. 1-18. The hydrophilic linkers possess three elements: a) Substituents that are either phosphamide, or phosphinate, or sulfonamide, or sulfonyl, or sulfonamide, and/or sulfoxide, or mixed of these groups, b) A group, such as but not limited to, a N-hydroxysuccinimide ester group, maleimido group, disulfide group, haloacetyl group, alkoxyamino group, and/or hydrazide group, capable of reaction with a cell-binding agent, and c) A group, such as but not limited to, a disulfide, maleimide, haloacetyl, aldehyde, ketone, azide, amine, alkoxyamine and hydrazide, capable of reaction with a drug. The hydrophilic substituents can be introduced by methods described herein. For example of the phosphamide substituents, they can be formed through directly condensation of phosphorus (V) oxychloride with amino molecules which are described in the FIGS. 1, 2, 3, 4 and 5. For the mixed the phosphinate/phosphamide substituents, they can be introduced by first treating a commercially available ammonium phosphinate with an acrylate via Michael addition, then substitution of excess amount of dibromo alkane to a phosphinate group, and followed by condensation with an amino compound, which are exampled in the FIGS. 6, 7, 8 and 9. For example of the sulfonamide and the sulfinamide substituents, they can be through directly condensation of sulfuryl chloride and thionyl chloride with amino compounds, which are exampled in the FIG. 10. The sulfonyl/sulfonamide substituent can be formed through condensation of chlorosulfonic acid with an amine which is exampled in the FIGS. 11 and 18. The detail synthesis of the hydrophilic linkers and their uses for the preparation of cell binding ligand-drug conjugates of this invention are disclosed in the FIGS. 1~18.

Preferably, the hydrophilic linkers are compounds of the Formula (I) below:

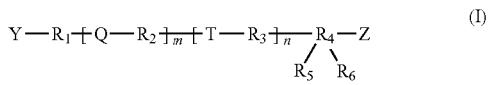

(I)

wherein:

Y represents a functional group that enables reaction with a cell-binding agent;

Q and T are either —$X_1$—P(=O)(OM)-, or —$X_1$—S($O_2$)—, or —$X_1$—S(O)—; or —$X_1$—P(=O)(OM)-$X_2$—, or —$X_1$—P(=O)[$X_2$—$R_4$—Z]—$X_3$—, or —$X_1$—P(=O)[$X_2$—$R_1$—Y]—$X_3$—, or —$X_1$—S($O_2$)—$X_2$—, or —$X_1$—S(O)—$X_2$—;

$X_1$, $X_2$ and $X_3$ are independently selected from N($R_7$), O, or S; In addition, when $X_1$ is either N($R_7$), or O, or S, then either $X_2$ or $X_3$, or another $X_1$ connects to —P(=O), —S(O), or —S($O_2$) can be $CH_2$.

m and n are integer from 0 to 5, but not 0 at the same time;

Z represents a functional group that enables linkage of a cytotoxic drug via an alkyl, alkylene, alkenylene, alkynylene, aromatic, heteroalkyl, disulfide, thioether, thioester, peptide, hydrazone, ether, ester, carbamate, carbonate, amine (secondary, tertiary, or quartary), imine, cycloheteroalkyane, heteroaromatic, alkoxime or amide bond;

$R_1$, $R_2$, $R_3$, $R_4$, $R_5$, $R_6$, $R_7$ and $R_8$ are the same or different and are H, linear alkyl having from 1-6 carbon atoms, branched or cyclic alkyl having from 3 to 6 carbon atoms, linear, branched or cyclic alkenyl or alkynyl, or 1~6 carbon atoms of esters, ether, amide, or polyethyleneoxy unit of formula ($OCH_2CH_2$)$_p$, wherein p is an integer from 0 to about 1000, or combination thereof.

M is H, or Na, or K, or $N^+R_1R_2R_3$ or a pharmaceutical salt. $R_1$, $R_2$ and $R_3$ are described above.

In another embodiment, $R_1$, $R_2$, $R_3$, and $R_4$ can be respectively a chain of atoms selected from C, N, O, S, Si, and P that covalently connects the cell-surface binding ligand, the phosphinate or sulfonyl or sulfoxide group, the conjugated drug and themselves ($R_1$, $R_2$, $R_3$ and $R_4$). The atoms used in forming the hydrophilic linker may be combined in all chemically relevant ways, such as forming alkylane, alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, acyloxylamines, hydroxamic acids, and many others. In addition, it is to be understood that the atoms forming the linker (L) may be either saturated or unsaturated, or may be radicals, or may be cyclized upon each other to form divalent cyclic structures, including cyclo alkanes, cyclic ethers, cyclic amines, arylenes, heteroarylenes, and the like in the linker.

Examples of the functional group, Y, that enables reaction with a cell-binding agent include amine reacting agents such as but not limited to N-hydroxysuccinimide esters, p-nitrophenyl esters, dinitrophenyl esters, pentafluorophenyl esters; thiol reactive agents such as but not limited to pyridyldisulfides, nitropyridyldisulfides, maleimides, haloacetates and carboxylic acid chlorides.

Examples of the functional group, Z, which enables linkage of a cytotoxic drug, include groups that enable linkage via a disulfide, thioether, thioester, peptide, hydrazone, ester, carbamate, carbonate, alkoxime or an amide bond. Such functional groups include, but are not limited to, thiol, disulfide, amino, carboxy, aldehydes, maleimido, haloacetyl, hydrazines, alkoxylamino, and/or hydroxy.

In preferred embodiments, $R_1$, $R_2$, $R_3$, and $R_4$, are linear alkyl having from 1-6 carbon atoms, or polyethyleneoxy unit of formula ($OCH_2CH_2$)$_p$, p=1~100.

In another embodiments, when the hydrophilic linkers of the Formula (I) has two or more Y groups, in particular the two same Y groups, at such case, either Q, or/and T is —$X_1$—P(=O)[$X_2$—$R_1$—Y]—$X_3$—, then the hydrophilic linkers of the Formula (I) can be for linking to two or more sites, particularly to a pair of sites of cell binding molecules. Wherein $X_1$, $X_2$ and $X_3$ are independently selected from N($R_7$), O, $CH_2$ or S; $R_1$ is defined above.

In yet another embodiments, when the hydrophilic linkers of the Formula (I) has two Z or more groups, at such case, either Q, or/and T is —$X_1$—P(=O)[$X_2$—$R_4$—Z]—$X_3$—, then the hydrophilic linkers of the Formula (I) can be for linking for two or more drugs, in particular, two different drugs. Wherein $X_1$, $X_2$ and $X_3$ are independently selected from N($R_7$), O, $CH_2$ or S; $R_4$ is defined above.

The synthesis of 2-dithio-pyridyl containing cross-linkers of Formulae (I) is shown, for example, in FIGS. 2, 6, 9, 11 and 12. The synthesis of maleimido-containing cross linkers of the Formula (I) is shown, for example, in FIGS. 1, 3, 4, 5, 7, 8, 10, 13, and 17.

The synthesis of thioether-containing cross linkers of the Formula (I) is shown, for example, in FIGS. 1, 3, 4, 5, 7, 8, 10, 12 and 17. The synthesis of polyethylene glycol-containing hydrophilic cross linkers of Formula (I) is shown, for example, in FIGS. 7, 8, 9, 11, 12, 13, 14, 15, 16, 17 and 18. The synthesis of azide-containing hydrophilic cross linkers of Formula (I) for Huisgen 1,3-dipolar cycloaddition of azides to alkynes (also called click chemistry) is shown, for example, in FIGS. 8, 9, 13 and 18. The synthesis of hydrophilic cross linkers of Formula (I) bearing hydrazide, or ketone, or alkoxime moieties enabling linkage via acid-labile bonds is shown, for example, in FIGS. 6, 9, 11, 14, 15 and 16. The synthesis of hydrophilic linkers of Formula (I) which can be linked two drugs per a linker, or linked two sites per a linker is shown, for example, in FIGS. 1, 2, 3, 4, 5, 6, 7, 17 and 18. The synthesis of hydrophilic linkers of Formula (I), which can be linked two different compounds/drugs per a linker, is shown, for example, in FIGS. 8, 9, 11, 14, 15, 16 and 17. The synthesis of hydrophilic linkers of Formula (I), which can be linked one cytotoxic compound and one chromophore molecule per a linker, is shown, for example, in FIG. 13.

Cell-Binding Agent-Drug Conjugates

The conjugates of the present invention can be represented by the following formula, Cb-(-L-Drug)$_n$, wherein Cb is a cell-binding agent, L is a hydrophilic linker, Drug is a drug molecule, and n is an integer from 1 to 20.

The hydrophilic linker L may be composed of one or more linker components. Exemplary linker components include 6-maleimidocaproyl ("MC"), maleimidopropanoyl ("MP"), valine-citrulline ("val-cit" or "vc"), alanine-phenylalanine ("ala-phe" or "af"), p-aminobenzyloxycarbonyl ("PAB"), 4-thiopentanoate ("SPP"), 4-(N-maleimidomethyl)cyclohexane-1 carboxylate ("MCC"), (4-acetyl)aminobenzoate ("SIAB"), 4-thio-butyrate (SPDB), 4-thio-2-hydroxysulfonyl-butyrate (2-Sulfo-SPDB), ethyleneoxy —CH$_2$CH$_2$O— as one or more repeating units ("EO" or "PEO"). Additional linker components are known in the art and some are described herein.

Example structures of these components containing linkers are:

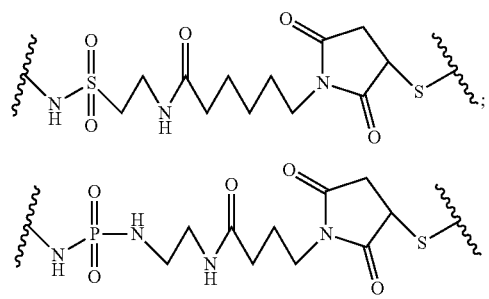

(MC, 6-maleimidocaproyl containing)

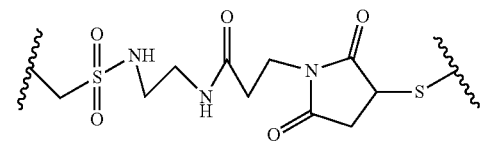 [SMILES: *CS(=O)(=O)NCCNC(=O)CCN1C(=O)CC(S*)C1=O]

(MP, maleimidopropanoyl containing)

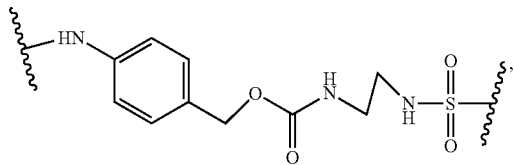

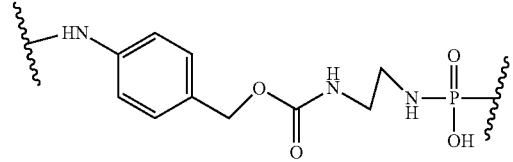

(PAB, p-aminobenzyloxycarbonyl containing)

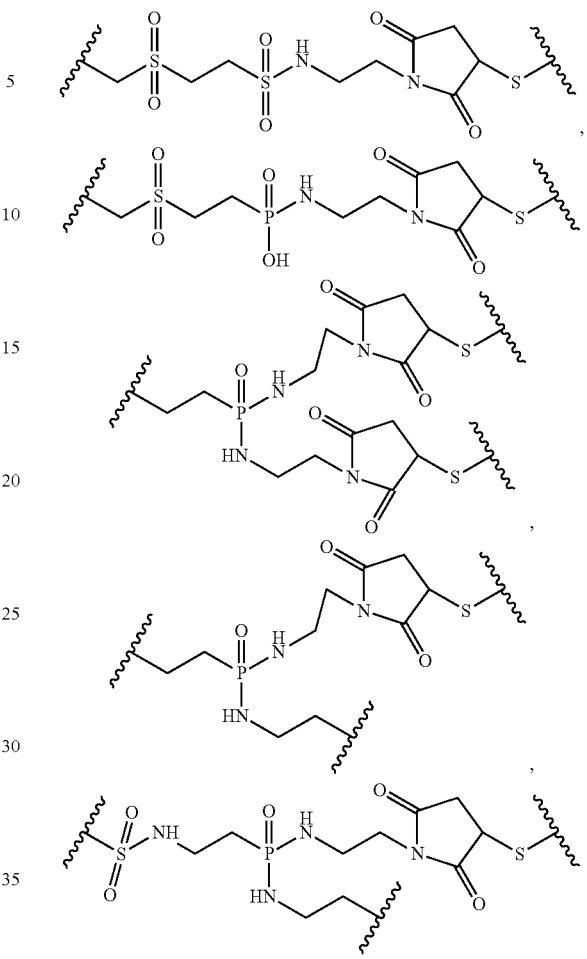

(ME, maleimidoethyl containing).

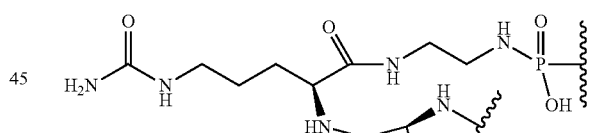

(valine-citrulline containing)

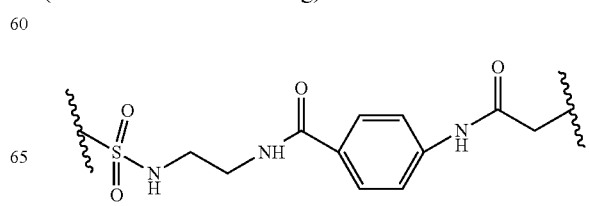

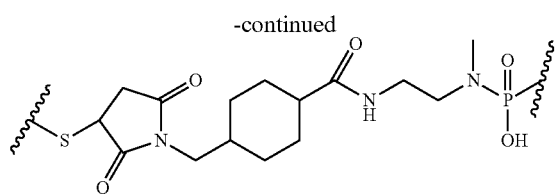

(MCC, 4-(N-maleimidomethyl)cyclohexane-1 carboxylate)

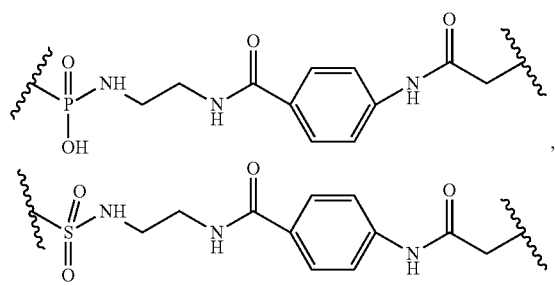

((4-acetyl)aminobenzoate containing)

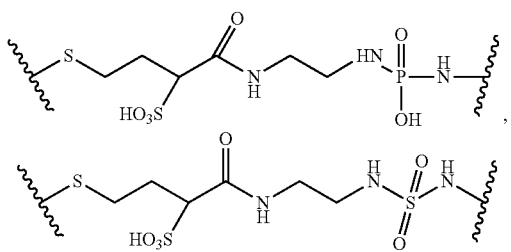

(4-thio-2-hydroxysulfonyl-butyrate, 2-sulfo-SPDB)

Preferably, the conjugates have the following Formula (II):

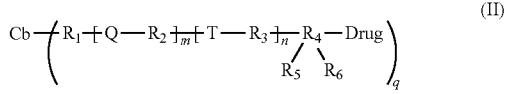

wherein:

Cb represents a cell-binding agent;

Drug represents the drug linked to the cell-binding agent via the hydrophilic linkers of this invention by an alkyl, alkylene, alkenylene, alkynylene, ether, polyoxyalkylene, ester, amine, imine, polyamine, hydrazine, hydrazone, amide, urea, semicarbazide, carbazide, alkoxyamine, urethanes, amino acid, peptide, acyloxylamine, hydroxamic acid, disulfide, thioether, thioester, carbamate, carbonate, heterocyclic ring, heteroalkyl, heteroaromatic, or alkoxime bond, or combination thereof.

q is 1~30; m, n, $R_1$, $R_2$, $R_3$, $R_4$, $R_5$, $R_6$ and M are described the same previously in Formula (I).

Q and T are either —$X_1$—P(=O)(OM)—, or —$X_1$—S($O_2$)—, or —$X_1$—S(O)—; or —$X_1$—P(=O)(OM)-$X_2$—, or —$X_1$—P(O)[$X_2$—$R_4$-Drug]-$X_3$—, or —$X_1$—P(=O)[$X_2$—R-Cb]—$X_3$—, or —$X_1$—S($O_2$)—$X_2$—, or —$X_1$—S(O)—$X_2$—; Wherein $X_1$, $X_2$ and $X_3$ are the same described in Formula (I).

In another embodiment, when the conjugate of the Formula (II) has two or more Cb groups, in particular the two same Cb groups, at such case, either Q, or/and T is —$X_1$—P(=O)[$X_2$—$R_1$-Cb]—$X_3$—, then the conjugate of the Formula (II) is linked to two or more sites, particularly a pair of sites of cell binding molecules.

In yet another embodiments, when the conjugate of the Formula (II) has two or more Drug groups, at such case, either Q, or/and T is —$X_1$—P(=O)[$X_2$—$R_4$-Drug]-$X_3$—, then the conjugate of the Formula (II) is linked to two or more drugs, in particular, two or more different drugs.

As described in more detail below, the drug can be any of many small molecule drugs, including, but not limited to, tubulysins, calicheamicins, auristatins, maytansinoids, CC-1065 analogs, morpholinos doxorubicins, taxanes, cryptophycins, epothilones, and benzodiazepine dimers (e.g., dimmers of pyrrolobenzodiazepine (PBD) or tomaymycin), indolinobenzodiazepines, imidazobenzothiadiazepines, or oxazolidinobenzodiazepines).

To synthesize the conjugate, the cell-binding agent can be first modified with the hydrophilic linkers of the present invention to introduce reactive groups of disulfide, maleimido, haloacetyl, azide, 1-yne, ketone, aldehyde, alkoxyamino, or hydrazide. Synthesis of the cell-binding agent-drug conjugates linked via disulfide bonds is achieved by a disulfide exchange between the disulfide bond in the modified cell-binding agent and a drug containing a free thiol group. Synthesis of the cell-binding agent-drug conjugates linked via thioether is achieved by reaction of the maleimido or haloacetyl or ethylsulfonyl modified cell-binding agent and a drug containing a free thiol group. Synthesis of conjugates bearing an acid labile hydrazone link can be achieved by reaction of a carbonyl group with the hydrazide moiety in the linker, by methods known in the art (see, for example, P. Hamann et al., Hinman, L. M., et al, Cancer Res. 53, 3336-334, 1993; B. Laguzza et al., J. Med. Chem., 32; 548-555, 1959; P. Trail et al., Cancer Res., 57; 100-105, 1997).

Alternatively, the drug can be modified with the hydrophilic linkers of the present invention to give a modified drug of Formula (IV) bearing functionality capable of reacting with a cell binding agent. For example a thiol-containing drug can be reacted with the hydrophilic linker of Formula (I) bearing a maleimdo, or a haloacetyl, or an ethylsulfonyl substituent at neutral pH in aqueous buffer to give a drug connected to the hydrophilic linker via a thioether link. A thiol-containing drug can undergo disulfide exchange with a hydrophilic linker bearing a pyrdiyldithio moiety to give a modified drug attached via a disulfide bond to the hydrophilic cross linker. A drug bearing a hydroxyl group or a thiol group can be reacted with a hydrophilic linker bearing a halogen of this invention, in the presence of a mild base, to give a modified drug bearing an ether or thiol ether link. A hydroxyl group containing drug can be condensed with a hydrophilic cross linker of Formula (I) bearing a carboxyl group, in the presence of a dehydrating agent, such as EDC or DCC, to give an ester link. An amino group containing drug can similarly undergo condensation with a carboxyl group on the hydrophilic linker of Formula (I) to give an amide bond.

The conjugate may be purified by standard biochemical means, such as gel filtration on a Sephadex G25 or Sephacryl S300 column, adsorption chromatography, and ion exchange or by dialysis. In some cases, a small molecule as a cell-binding agent (e.g. folic acid, melanocyte stimulating hormone, EGF etc) conjugated with a small molecular drugs can be purified by chromatography such as by HPLC, medium pressure column chromatography or ion exchange chromatography.

Modified Cell-Binding Agents

The cell-binding agent modified by reaction with linkers of the present invention are preferably represented by the Formula (III)

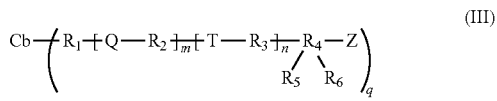

Wherein Cb, q, m, n, $R_1$, $R_2$, $R_3$, $R_4$, $R_5$, $R_6$ and Z, as well as the substituents inside are described the same previously in Formula (I) and (II).

Q and T are either $-X_1-P(=O)(OM)-$, or $-X_1-S(O_2)-$, or $-X_1-S(O)-$; or $-X_1-P(=O)(OM)-X_2-$, or $-X_1-P(=O)[X_2-R_4-Z]-X_3-$, or $-X_1-P(=O)[X_2-R_1-Cb]-X_3-$, or $-X_1-S(O_2)-X_2-$, or $-X_1-S(O)-X_2-$; Wherein $X_1$, $X_2$ and $X_3$ are the same described in Formula (I).

In another embodiment, when the compound of the Formula (III) has two or more Cb groups, in particular the two same Cb groups, at such case, either Q, or/and T is $-X_1-P(=O)[X_2-R_1-Cb]-X_3-$, then the compound of the Formula (III) is linked to two or more sites, particularly a pair of sites of cell binding molecules.

In yet another embodiment, when the compound of the Formula (III) has two or more Z groups, at such case, either Q, or/and T is $-X_1-P(=O)[X_2-R_4-Z]-X_3-$, then the compound of the Formula (III) can be used to link to two or more drugs, in particular, two different drugs.

In preferred embodiments, Z is a disulfide substituent, maleimido, haloacetyl, alkoxyamine, hydrazine group, or an N-hydroxysuccinimide ester, and Cb linked with $R_1$ is through thioether, hydrazone, amide, alkoxime, carbamate, or disulfide bond. The modified cell-binding agent can be prepared via a reaction of the cell-binding agent with the hydrophilic linkers by methods known in the art for other cross-linkers (U.S. Pat. Nos. 5,846,545, 5,585,499, 5,475,092, 5,414,064, 5,208,020, and 4,563,304; Carlsson, J. et al. *Biochem. J.* (1978) 173, 723-737(1978); Goff, D. A., Bioconj. Chem. (1990), 1, 381-386; L. Delprino et al. *J. Pharm. Sci.* (1993), 82, 506-512; S. Arpicco et al., *Bioconjugate Chem*(1997), 8, 327-337).

Advantageously, because the phosphamide, phosphinate, sulfonamide, sulfonyl, sulfonimide, and/or sulfoxide groups on the hydrophilic linkers are soluble in water or require only a small percentage of organic solvent to maintain solubility in aqueous solution, the reaction between the cell-binding agent and the cross-linker can be conducted in aqueous solution. The cross-linking reagent is dissolved in aqueous buffer, optionally containing a small amount (typically <10% by volume) of a polar organic solvent that is miscible with water, for example different alcohols, such as methanol, ethanol, and propanol, acetone, acetonitrile, tetrahydrofuran (THF), 1,4-dioxane, dimethyl formamide (DMF), dimethyl acetamide (DMA), or dimethylsulfoxide (DMSO) at a high concentration, for example 1-100 mM, and then an appropriate aliquot is added to the buffered aqueous solution of the cell-binding agent. An appropriate aliquot is an amount of solution that introduces 1-10 cross-linking groups per cell-binding agent, preferably 1-6 groups, and the volume to be added should not exceed 10%, preferably 5%, and most preferably 0-3% of the volume of the cell-binding agent solution. The aqueous solutions for the cell-binding agents are buffered between pH 6 and 9, preferably between 6.5 and 7.5 and can contain any non-nucleophilic buffer salts useful for these pH ranges. Typical buffers include phosphate, triethanolamine HCl, HEPES, and MOPS buffers, which can contain additional components, such as cyclodextrins, sucrose and salts, for examples, NaCl and KCl. After the addition the reaction is incubated at a temperature of from 4° C. to 45° C., preferably at ambient temperature. The progress of the reaction can be monitored by measuring the increase in the absorption at 280, or 320 nm, or another appropriate wavelength. After the reaction is complete, isolation of the modified cell-binding agent can be performed in a routine way, using for example gel filtration chromatography, or adsorptive chromatography.

The extent of modification can be assessed by measuring the absorbance of the nitropyridine thione, dinitropyridine dithione, pyridine thione, carboxamidopyridine dithione and dicarboxamidopyridine dithione group released. The hydrophilic cross-linkers described herein have diverse functional groups that can react with any cell-binding agent that possesses a suitable substituent. For example cell-binding agents bearing an amino or hydroxyl substituent can react with cross linkers bearing an N-hydroxysuccinimide (NHS) ester, cell-binding agents bearing a thiol substituent can react with cross linkers bearing a maleimido or haloacetyl group. Additionally, cell-binding agents bearing a carbonyl substituent can react with the linkers bearing a hydrazide or an alkoxyamine. One skilled in the art can readily determine which linker to use based on the known reactivity of the available functional group on the cell-binding agent.

Modified Cytotoxic Drugs

The cytotoxic drugs modified by reaction with cross-linkers of the present invention are preferably represented by the Formula (IV):

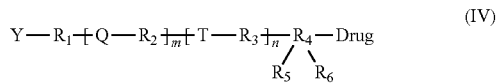

wherein Y, m, n, $R_1$, $R_2$, $R_3$, $R_4$, $R_5$, $R_6$ and Drug, as well as the substituents inside the Formula (IV) are described the same previously in Formula (I) and (II).

Q and T are either $-X_1-P(=O)(OM)-$, or $-X_1-S(O_2)-$, or $-X_1-S(O)-$; or $-X_1-P(=O)(OM)-X_2-$, or $-X_1-P(O)[X_2-R_4-Drug]-X_3-$, or $-X_1-P(=O)[X_2-R_1-Y]-X_3-$, or $-X_1-S(O_2)-X_2-$, or $-X_1-S(O)-X_2-$; Wherein $X_1$, $X_2$ and $X_3$ are the same described in Formula (I).

In another embodiment, when the compound of the Formula (IV) has two or more Y groups, in particular the two same Y groups, at such case, either Q, or/and T is $-X_1-P(=O)[X_2-R_1-Y]-X_3-$, then compound of the Formula (IV) can be linked to two or more sites, particularly a pair of sites of cell binding molecules.

In yet another embodiment, when the compound of the Formula (IV) has two or more Drug groups, at such case, either Q, or/and T is $-X_1-P(=O)[X_2-R_4-Drug]-X_3-$, then the compound of the Formula (II) is linked to two or more drugs, in particular, two or more different drugs.

In preferred embodiments, Y is a disulfide substituent, a maleimido, a haloacetyl, an alkoxylamino group, carboxylic acid, or an N-hydroxysuccinimide ester.

The modified drugs can be prepared by reacting the drug with the linkers of the present invention to give a modified drug of Formula (IV) bearing functionality capable of reacting with a cell binding agent. For example a thiol-containing drug can be reacted with the linker of Formula (I) bearing a maleimdo substituent at neutral pH in aqueous buffer to give a drug connected to the hydrophilic linker via thioether linkage. A thiol-containing drug can undergo disulfide exchange with a hydrophilic linker bearing a pyrdiyldithio moiety to give a modified drug attached via a disulfide bond to the hydrophilic linker. A drug bearing a hydroxyl group can be reacted with a linker bearing a halogen, in the presence of a mild base, to give a modified drug bearing ether linkage. A hydroxyl group containing drug can be condensed with a linker of Formula (I) bearing a carboxyl group, in the presence of a dehydrating agent, such as EDC or dicyclohexylcarbodiimide (DCC), to give ester linkage. A drug bearing a thiol group can be reacted with a linker bearing a maleimido or a vinylsulfonyl, or a haloacetyl group, to give a modified drug bearing thioether linkage. An amino group containing drug can similarly undergo condensation with a carboxyl group on the hydrophilic linker of Formula (I) to give an amide bond. The modified drug can be purified by standard methods such as column chromatography over silica gel or alumina, crystallization, preparatory thin layer chromatography, ion exchange chromatography, or HPLC.

Cell-Binding Agents

The cell-binding molecule that comprises the conjugates and the modified cell-binding agents of the present invention may be of any kind presently known, or that become known, molecule that binds to, complexes with, or reacts with a moiety of a cell population sought to be therapeutically or otherwise biologically modified.

The cell binding agents include, but are not limited to, large molecular weight proteins such as, for example, full-length antibodies (polyclonal antibodies, monoclonal antibodies, dimers, multimers, multispecific antibodies (e.g., bispecific antibodies); single chain antibodies; fragments of antibodies such as Fab, Fab', F(ab')$_2$, F$_v$, [Parham, J. Immunol. 131, 2895-2902 (1983)], fragments produced by a Fab expression library, anti-idiotypic (anti-Id) antibodies, CDR's, and epitope-binding fragments of any of the above which immuno-specifically bind to cancer cell antigens, viral antigens, microbial antigens or a protein generated by the immune system that is capable of recognizing, binding to a specific antigen or exhibiting the desired biological activity (Miller et al (2003) J. of Immunology 170:4854-4861); interferons (such as type I, II, III); peptides; lymphokines such as IL-2, IL-3, IL-4, IL-5, IL-6, IL-10, GM-CSF, interferon-gamma (IFN-γ); hormones such as insulin, TRH (thyrotropin releasing hormones), MSH (melanocyte-stimulating hormone), steroid hormones, such as androgens and estrogens, melanocyte-stimulating hormone (MSH); growth factors and colony-stimulating factors such as epidermal growth factors (EGF), granulocyte-macrophage colony-stimulating factor (GM-CSF), transforming growth factors (TGF), such as TGFα, TGFβ, insulin and insulin like growth factors (IGF-I, IGF-II) G-CSF, M-CSF and GM-CSF [Burgess, Immunology Today, 5, 155-158 (1984)]; vaccinia growth factors (VGF); fibroblast growth factors (FGFs); smaller molecular weight proteins, poly-peptide, peptides and peptide hormones, such as bombesin, gastrin, gastrin-releasing peptide; platelet-derived growth factors; interleukin and cytokines, such as interleukin-2 (IL-2), interleukin-6 (IL-6), leukemia inhibitory factors, granulocyte-macrophage colony-stimulating factor (GM-CSF); vitamins, such as folate; apoproteins and glycoproteins, such as transferrin [O'Keefe et al, 260 J. Biol. Chem. 932-937 (1985)]; sugar-binding proteins or lipoproteins, such as lectins; cell nutrient-transport molecules; and small molecular inhibitors, such as prostate-specific membrane antigen (PSMA) inhibitors and small molecular tyrosine kinase inhibitors (TKI), non-peptides or any other cell binding molecule or substance, such as bioactive polymers (Dhar, et al, Proc. Natl. Acad. Sci. 2008, 105, 17356-61); bioactive dendrimers (Lee, et al, Nat. Biotechnol. 2005, 23, 1517-26; Almutairi, et al; Proc. Natl. Acad. Sci. 2009, 106, 685-90); nanoparticles (Liong, et al, ACS Nano, 2008, 19, 1309-12; Medarova, et al, Nat. Med. 2007, 13, 372-7; Javier, et al, Bioconjugate Chem. 2008, 19, 1309-12); liposomes (Medinai, et al, Curr. Phar. Des. 2004, 10, 2981-9); viral capsides (Flenniken, et al, Viruses Nanotechnol. 2009, 327, 71-93).

In general, a monoclonal antibody is preferred as a cell-surface binding agent if an appropriate one is available. And the antibody may be murine, human, humanized, chimeric, or derived from other species.

Production of antibodies used in the present invention involves in vivo or in vitro procedures or combinations thereof. Methods for producing polyclonal anti-receptor peptide antibodies are well-known in the art, such as in U.S. Pat. No. 4,493,795 (to Nestor et al). A monoclonal antibody is typically made by fusing myeloma cells with the spleen cells from a mouse that has been immunized with the desired antigen (Köhler, G.; Milstein, C. (1975). *Nature* 256: 495-497). The detailed procedures are described in "Antibodies—A Laboratory Manual", Harlow and Lane, eds., Cold Spring Harbor Laboratory Press, New York (1988), which is incorporated herein by reference. Particularly monoclonal antibodies are produced by immunizing mice, rats, hamsters or any other mammal with the antigen of interest such as the intact target cell, antigens isolated from the target cell, whole virus, attenuated whole virus, and viral proteins. Splenocytes are typically fused with myeloma cells using polyethylene glycol (PEG) 6000. Fused hybrids are selected by their sensitivity to HAT (hypoxanthine-aminopterin-thymine). Hybridomas producing a monoclonal antibody useful in practicing this invention are identified by their ability to immunoreact specified receptors or inhibit receptor activity on target cells.

A monoclonal antibody used in the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques, such as using protein-A affinity chromatography; anion, cation, hydrophobic, or size exclusive chromatographies (particularly by affinity for the specific antigen after protein A, and sizing column chromatography); centrifugation, differential solubility, or by any other standard technique for the purification of proteins.

Media useful for the preparation of these compositions are both well-known in the art and commercially available and include synthetic culture media. An exemplary synthetic medium is Dulbecco's minimal essential medium (DMEM; Dulbecco et al., Virol. 8, 396 (1959)) supplemented with 4.5 gm/l glucose, 0~20 mM glutamine, 0~20% fetal calf serum, several ppm amount of heavy metals, such as Cu, Mn, Fe, or Zn, etc, or/and the heavy metals added in their salt forms, and with an anti-foaming agent, such as polyoxyethylene-polyoxypropylene block copolymer.

In addition, antibody-producing cell lines can also be created by techniques other than fusion, such as direct transformation of B lymphocytes with oncogenic DNA, or transfection with an oncovirus, such as Epstein-Barr virus (EBV, also called human herpesvirus 4 (HHV-4)) or Kaposi's sarcoma-associated herpesvirus (KSHV). See, U.S. Pat. Nos. 4,341,761; 4,399,121; 4,427,783; 4,444,887; 4,451,570; 4,466,917; 4,472,500; 4,491,632; 4,493,890. A monoclonal antibody may also be produced via an anti-receptor peptide or peptides containing the carboxyl terminal as described well-known in the art. See Niman et al., Proc. Natl. Acad. Sci. USA, 80: 4949-4953 (1983); Geysen et al., Proc. Natl. Acad. Sci. USA, 82: 178-182 (1985); Lei et al. Biochemistry 34(20): 6675-6688, (1995). Typically, the anti-receptor peptide or a peptide analog is used either alone or conjugated to an immunogenic carrier, as the immunogen for producing anti-receptor peptide monoclonal antibodies.

There are also a number of other well-known techniques for making monoclonal antibodies as binding molecules in this invention. Particularly useful are methods of making fully human antibodies. One method is phage display technology which can be used to select a range of human antibodies binding specifically to the antigen using methods of affinity enrichment. Phage display has been thoroughly described in the literature and the construction and screening of phage display libraries are well known in the art, see, e.g., Dente et al, Gene. 148(1):7-13 (1994); Little et al, Biotechnol Adv. 12(3):539-55 (1994); Clackson et al., Nature 352: 264-628 (1991); Huse et al., Science 246:1275-1281 (1989).

Monoclonal antibodies derived by hybridoma technique from another species than human, such as mouse, can be humanized to avoid human anti-mouse antibodies when infused into humans. Among the more common methods of humanization of antibodies are complementarity-determining region grafting and resurfacing. These methods have been extensively described, see e.g. U.S. Pat. Nos. 5,859,205 and 6,797,492; Liu et al, Immunol Rev. 222:9-27 (2008); Almagro et al, Front Biosci. 13: 1619-33 (2008); Lazar et al, Mol Immunol. 44(8):1986-98 (2007); Li et al, Proc. Natl. Acad. Sci. USA. 103(10):3557-62 (2006) each incorporated herein by reference. Fully human antibodies can also be prepared by immunizing transgenic mice, rabbits, monkeys, or other mammals, carrying large portions of the human immunoglobulin heavy and light chains, with an immunogen. Examples of such mice are: the Xenomouse. (Abgenix/Amgen), the HuMAb-Mouse (Medarex/BMS), the VelociMouse (Regeneron), see also U.S. Pat. Nos. 6,596,541, 6,207,418, 6,150,584, 6,111,166, 6,075,181, 5,922,545, 5,661,016, 5,545,806, 5,436,149 and 5,569,825. In human therapy, murine variable regions and human constant regions can also be fused to construct called "chimeric antibodies" that are considerably less immunogenic in man than murine mAbs (Kipriyanov et al, Mol Biotechnol. 26:39-60 (2004); Houdebine, Curr Opin Biotechnol. 13:625-9 (2002) each incorporated herein by reference). In addition, site-directed mutagenesis in the variable region of an antibody can result in an antibody with higher affinity and specificity for its antigen (Brannigan et al, Nat Rev Mol Cell Biol. 3:964-70, (2002)); Adams et al, J Immunol Methods. 231:249-60 (1999)) and exchanging constant regions of a mAb can improve its ability to mediate effector functions of binding and cytotoxicity.

Antibodies immunospecific for a malignant cell antigen can also be obtained commercially or produced by any method known to one of skill in the art such as, e.g., chemical synthesis or recombinant expression techniques. The nucleotide sequence encoding antibodies immunospecific for a malignant cell antigen can be obtained commercially, e.g., from the GenBank database or a database like it, the literature publications, or by routine cloning and sequencing.

Apart from an antibody, a peptide or protein that bind/block/target or in some other way interact with the epitopes or corresponding receptors on a targeted cell can be used as a binding molecule. These peptides or proteins could be any random peptide or proteins that have an affinity for the epitopes or corresponding receptors and they don't necessarily have to be of the immunoglobulin family. These peptides can be isolated by similar techniques as for phage display antibodies (Szardenings, J Recept Signal Transduct Res. 2003; 23(4):307-49). The use of peptides from such random peptide libraries can be similar to antibodies and antibody fragments. The binding molecules of peptides or proteins may be conjugated on or linked to a large molecules or materials, such as, but is not limited, an albumin, a polymer, a liposome, a nano particle, a dendrimer, as long as such attachment permits the peptide or protein to retain its antigen binding specificity.

Examples of antibodies used for conjugation of drugs via the hydrophilic linkers of this prevention for treating cancer, autoimmune disease, and/or infectious disease include, but are not limited to, 3F8 (anti-GD2), Abagovomab (anti CA-125), Abciximab (anti CD41 (integrin alpha-IIb), Adalimumab (anti-TNF-α), Adecatumumab (anti-EpCAM, CD326), Afelimomab (anti-TNF-α); Afutuzumab (anti-CD20), Alacizumab pegol (anti-VEGFR2), ALD518 (anti-IL-6), Alemtuzumab (Campath, MabCampath, anti-CD52), Altumomab (anti-CEA), Anatumomab (anti-TAG-72), Anrukinzumab (IMA-638, anti-IL-13), Apolizumab (anti-HLA-DR), Arcitumomab (anti-CEA), Aselizumab (anti-L-selectin (CD62L), Atlizumab (tocilizumab, Actemra, RoActemra, anti-IL-6 receptor), Atorolimumab (anti-Rhesus factor), Bapineuzumab (anti-beta amyloid), Basiliximab (Simulect, antiCD25 (α chain of IL-2 receptor), Bavituximab (anti-phosphatidylserine), Bectumomab (LymphoScan, anti-CD22), Belimumab (Benlysta, LymphoStat-B, anti-BAFF), Benralizumab (anti-CD125), Bertilimumab (anti-CCL11 (eotaxin-1)), Besilesomab (Scintimun, anti-CEA-related antigen), Bevacizumab (Avastin, anti-VEGF-A), Biciromab (FibriScint, anti-fibrin II beta chain), Bivatuzumab (anti-CD44 v6), Blinatumomab (BiTE, anti-CD19), Brentuximab (cAC10, anti-CD30 TNFRSF8), Briakinumab (anti-IL-12, IL-23) Canakinumab (Iaris, anti-IL-1), Cantuzumab (C242, anti-CanAg), Capromab, Catumaxomab (Removab, anti-EpCAM, anti-CD3), CC49 (anti-TAG-72), Cedelizumab (anti-CD4), Certolizumab pegol (Cimzia anti-TNF-α), Cetuximab (Erbitux, IMC-C225, anti-EGFR), Citatuzumab bogatox (anti-EpCAM), Cixutumumab (anti-IGF-1), Clenoliximab (anti-CD4), Clivatuzumab (anti-MUC1), Conatumumab (anti-TRAIL-R2), CR6261 (anti-Influenza A hemagglutinin), Dacetuzumab (anti-CD40), Daclizumab (Zenapax, anti-CD25 (α chain of IL-2 receptor)), Daratumumab (anti-CD38 (cyclic ADP ribose hydrolase), Denosumab (Prolia, anti-RANKL), Detumomab (anti-B-lymphoma cell), Dorlimomab, Dorlixizumab, Ecromeximab (anti-GD3 ganglioside), Eculizumab (Soliris, anti-C5), Edobacomab (anti-endotoxin), Edrecolomab (Panorex, MAb17-1A, anti-EpCAM), Efalizumab (Raptiva, anti-LFA-1 (CD11a), Efungumab (Mycograb, anti-Hsp90), Elotuzumab (anti-SLAMF7), Elsilimomab (anti-IL-6), Enlimomab pegol (anti-ICAM-1 (CD54)), Epitumomab (anti-episialin), Epratuzumab (anti-CD22), Erlizumab (anti-ITGB2 (CD18)), Ertumaxomab (Rexomun, anti-HER2/neu, CD3), Etaracizumab (Abegrin, anti-integrin $\alpha_v\beta_3$), Exbivirumab (anti-hepatitis B surface antigen), Fanolesomab (NeutroSpec, anti-CD15), Faralimomab (anti-interferon receptor), Farletuzumab (anti-folate receptor 1), Felvizumab (anti-respiratory syncytial virus), Fezakinumab (anti-IL-22), Figitumumab (anti-IGF-1 receptor), Fontolizumab (anti-IFN-γ), Foravirumab (anti-rabies virus glycoprotein), Fresolimumab (anti-TGF-3), Galiximab (anti-CD80), Gantenerumab (anti-beta amyloid), Gavilimomab (anti-CD147 (basigin)), Gemtuzumab (anti-CD33), Girentuximab (anti-carbonic anhydrase 9), Glembatumumab (CR011, anti-GPNMB), Golimumab (Simponi, anti-TNF-α), Gomiliximab (anti-CD23 (IgE receptor)), Ibalizumab (anti-CD4), Ibritumomab (anti-CD20), Igovomab (Indimacis-125, anti-CA-125), Imciromab (Myoscint, anti-cardiac myosin), Infliximab (Remicade, anti-TNF-α), Intetumumab (anti-CD51), Inolimomab (anti-CD25 (a chain of IL-2 receptor)), Inotuzumab (anti-CD22), Ipilimumab (anti-CD152), Iratumumab (anti-CD30 (TNFRSF8)), Keliximab (anti-CD4), Labetuzumab (CEA-Cide, anti-CEA), Lebrikizumab (anti-IL-13), Lemalesomab (anti-NCA-90 (granulocyte antigen)), Lerdelimumab (anti-TGF beta 2), Lexatumumab (anti-TRAIL-R2), Libivirumab (anti-hepatitis B surface antigen), Lintuzumab (anti-CD33), Lucatumumab (anti-CD40), Lumiliximab (anti-CD23 (IgE receptor), Mapatumumab (anti-TRAIL-R1), Maslimomab (anti-T-cell receptor), Matuzumab (anti-EGFR), Mepolizumab (Bosatria, anti-IL-5), Metelimumab (anti-TGF beta 1), Milatuzumab (anti-CD74), Minretumomab (anti-TAG-72), Mitumomab (BEC-2, anti-GD3 ganglioside), Morolimumab (anti-Rhesus factor), Motavizumab (Numax, anti-respiratory syncytial virus), Muromonab-CD3 (Orthoclone OKT3, anti-CD3), Nacolomab (anti-C242), Naptumomab (anti-5T4), Natalizumab (Tysabri, anti-integrin $\alpha_4$), Nebacumab (anti-endotoxin), Necitumumab (anti-EGFR), Nerelimomab (anti-TNF-α), Nimotuzumab (Theracim, Theraloc, anti-EGFR), Nofetumomab, Ocrelizumab (anti-CD20), Odulimomab (Afolimomab, anti-LFA-1 (CD11a)), Ofatumumab (Arzerra, anti-CD20), Olaratumab (anti-PDGF-R α), Omalizumab (Xolair, anti-IgE Fc region), Oportuzumab (anti-EpCAM), Oregovomab (OvaRex, anti-CA-125), Otelixizumab (anti-CD3), Pagibaximab (anti-lipoteichoic acid), Palivizumab (Synagis, Abbosynagis, anti-respiratory syncytial virus), Panitumumab (Vectibix, ABX-EGF, anti-EGFR), Panobacumab (anti-*Pseudomonas aeruginosa*), Pascolizumab (anti-IL-4), Pemtumomab (Theragyn, anti-MUC1), Pertuzumab (Omnitarg, 2C4, anti-HER2/neu), Pexelizumab (anti-C5), Pintumomab (anti-adenocarcinoma antigen), Priliximab (anti-CD4), Pritumumab (anti-vimentin), PRO 140 (anti-CCR5), Racotumomab (1E10, anti-(N-glycolylneuraminic acid (NeuGc, NGNA)-gangliosides GM3)), Rafivirumab (anti-rabies virus glycoprotein), Ramucirumab (anti-VEGFR2), Ranibizumab (Lucentis, anti-VEGF-A), Raxibacumab (anti-anthrax toxin, protective antigen), Regavirumab (anti-cytomegalovirus glycoprotein B), Reslizumab (anti-IL-5), Rilotumumab (anti-HGF), Rituximab (MabThera, Rituxanmab, anti-CD20), Robatumumab (anti-IGF-1 receptor), Rontalizumab (anti-IFN-α), Rovelizumab (LeukArrest, anti-CD11, CD18), Ruplizumab (Antova, anti-CD154 (CD40L)), Satumomab (anti-TAG-72), Sevirumab (anti-cytomegalovirus), Sibrotuzumab (anti-FAP), Sifalimumab (anti-IFN-α), Siltuximab (anti-IL-6), Siplizumab (anti-CD2), (Smart) MI95 (anti-CD33), Solanezumab (anti-beta amyloid), Sonepcizumab (anti-sphingosine-1-phosphate), Sontuzumab (anti-episialin), Stamulumab (anti-myostatin), Sulesomab (LeukoScan, (anti-NCA-90 (granulocyte antigen), Tacatuzumab (anti-alpha-fetoprotein), Tadocizumab (anti-integrin $\alpha_{IIb}\beta_3$), Talizumab (anti-IgE), Tanezumab (anti-NGF), Taplitumomab (anti-CD19), Tefibazumab (Aurexis, anti-clumping factor A), Telimomab, Tenatumomab (anti-tenascin C), Teneliximab (anti-CD40), Teplizumab (anti-CD3), TGN1412 (anti-CD28), Ticilimumab (Tremelimumab, (anti-CTLA-4), Tigatuzumab (anti-TRAIL-R2), TNX-650 (anti-IL-13), Tocilizumab (Atlizumab, Actemra, RoActemra, (anti-IL-6 receptor), Toralizumab (anti-CD154 (CD40L)), Tositumomab (anti-CD20), Trastuzumab (Herceptin, (anti-HER2/neu), Tremelimumab (anti-CTLA-4), Tucotuzumab celmoleukin (anti-EpCAM), Tuvirumab (anti-hepatitis B virus), Urtoxazumab (anti-*Escherichia coli*), Ustekinumab (Stelara, anti-IL-12, IL-23), Vapaliximab (anti-AOC3 (VAP-1)), Vedolizumab, (anti-integrin $\alpha_4\beta_7$), Veltuzumab (anti-CD20), Vepalimomab (anti-AOC3 (VAP-1), Visilizumab (Nuvion, anti-CD3), Vitaxin (anti-vascular integrin avb3), Volociximab (anti-integrin $\alpha_5\beta_1$), Votumumab (HumaSPECT, anti-tumor antigen CTAA16.88), Zalutumumab (HuMax-EGFr, (anti-EGFR), Zanolimumab (HuMax-CD4, anti-CD4), Ziralimumab (anti-CD147 (basigin)), Zolimomab (anti-CD5), Etanercept (Enbrel®), Alefacept (Amevive®), Abatacept (Orencia®), Rilonacept (Arcalyst), 14F7 [anti-IRP-2 (Iron Regulatory Protein 2)], 14G2a (anti-GD2 ganglioside, from Nat. Cancer Inst. for melanoma and solid tumors), J591 (anti-PSMA, Weill Cornell Medical School for prostate cancers), 225.28S [anti-HMWMAA (High molecular weight-melanoma-associated antigen), Sorin Radiofarmaci S.R.L. (Milan, Italy) for melanoma], COL-1 (anti-CEACAM3, CGM1, from Nat. Cancer Inst. USA for colorectal and gastric cancers), CYT-356 (Oncoltad®, for prostate cancers), HNK20 (OraVax Inc. for respiratory syncytial virus), ImmuRAIT (from Immunomedics for NHL), Lym-1 (anti-HLA-DR10, Peregrine Pharm. for Cancers), MAK-195F [anti-TNF (tumor necrosis factor; TNFA, TNF-alpha; TNFSF2), from Abbott/Knoll for Sepsis toxic shock], MEDI-500 [T10B9, anti-CD3, TRαβ (T cell receptor alpha/beta), complex, from MedImmune Inc for Graft-versus-host disease], RING SCAN [anti-TAG 72 (tumour associated glycoprotein 72), from Neoprobe Corp. for Breast, Colon and Rectal cancers], Avicidin (anti-EPCAM (epithelial cell adhesion molecule), anti-TACSTD1 (Tumor-associated calcium signal transducer 1), anti-GA733-2 (gastrointestinal tumor-associated protein 2), anti-EGP-2 (epithelial glycoprotein 2); anti-KSA; KS1/4 antigen; M4S; tumor antigen 17-1A; CD326, from NeoRx Corp. for Colon, Ovarian, Prostate cancers and NHL]; LymphoCide (Immunomedics, NJ), Smart ID10 (Protein Design Labs), Oncolym (Techniclone Inc, CA), Allomune (BioTransplant, CA), anti-VEGF (Genentech, CA); CEAcide (Immunomedics, NJ), IMC-1C11 (ImClone Systems, NJ) and Cetuximab (ImClone, NJ).

Other antibodies as cell binding molecules/ligands include, but are not limited to, are antibodies against the following antigens: Aminopeptidase N (CD13), Annexin A1, B7-H3 (CD276, various cancers), CA125 (ovarian), CA15-3 (carcinomas), CA19-9 (carcinomas), L6 (carcinomas), Lewis Y (carcinomas), Lewis X (carcinomas), alpha fetoprotein (carcinomas), CA242 (colorectal), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (Metastatic melanoma, sarcoma), CD52 (leukemia), CD56 (small cell lung cancers, ovarian cancer, Merkel cell carcinoma, and the liquid tumor, multiple myeloma), CD66e (cancers), CD70 (metastatic renal cell carcinoma and non-Hodgkin lymphoma), CD74 (multiple myeloma), CD80 (lymphoma), CD98 (cancers), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (carcinoembryonic antigen; CEA, CD66e) (breast, colorectal and lung cancers), DLL4 (delta-like-4), EGFR (Epidermal Growth Factor Receptor, various cancers), CTLA4 (melanoma), CXCR4 (CD184, Heme-oncology, solid tumors), Endoglin (CD105, solid tumors), EPCAM (epithelial cell adhesion molecule, bladder, head, neck, colon, NHL prostate, and ovarian cancers), ERBB2 (Epidermal Growth Factor Receptor 2; lung, breast, prostate cancers), FCGR1 (autoimmune diseases), FOLR (folate receptor, ovarian cancers), GD2 ganglioside (cancers), G-28 (a cell surface antigen glyvolipid, melanoma), GD3 idiotype (cancers), Heat shock proteins (cancers), HER1 (lung, stomach cancers), HER2 (breast, lung and ovarian cancers), HLA-DR10 (NHL), HLA-DRB (NHL, B cell leukemia), human chorionic gonadotropin (carcinoma), IGF1R (insulin-like growth factor 1 receptor, solid tumors, blood cancers), IL-2 receptor (interleukin 2 receptor, T-cell leukemia and lymphomas), IL-6R (interleukin 6 receptor, multiple myeloma, RA, Castleman's disease, IL6 dependent tumors), Integrins ($\alpha v \beta 3$, $\alpha 5 \beta 1$, $\alpha 6 \beta 4$, $\alpha II \beta 3$, $\alpha 5 \beta 5$, $\alpha v \beta 5$, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 or MUC1-KLH (breast, ovarian, cervix, bronchus and gastrointestinal cancer), MUC16 (CA125) (Ovarian cancers), CEA (colorectal), gp100 (melanoma), MART1 (melanoma), MPG (melanoma), MS4A1 (membrane-spanning 4-domains subfamily A, small cell lung cancers, NHL), Nucleolin, Neu oncogene product (carcinomas), P21 (carcinomas), Paratope of anti-(N-glycolylneuraminic acid, Breast, Melanoma cancers), PLAP-like testicular alkaline phosphatase (ovarian, testicular cancers), PSMA (prostate tumors), PSA (prostate), ROBO4, TAG 72 (tumour associated glycoprotein 72, AML, gastric, colorectal, ovarian cancers), T cell transmembrane protein (cancers), Tie (CD202b), TNFRSF10B (tumor necrosis factor receptor superfamily member 10B, cancers), TNFRSF13B (tumor necrosis factor receptor superfamily member 13B, multiple myeloma, NHL, other cancers, RA and SLE), TPBG (trophoblast glycoprotein, Renal cell carcinoma), TRAIL-R1 (Tumor necrosis apoprosis Inducing ligand Receptor 1, lymphoma, NHL, colorectal, lung cancers), VCAM-1 (CD106, Melanoma), VEGF, VEGF-A, VEGF-2 (CD309) (various cancers). Some other tumor associated antigens recognized by antibodies have been reviewed (Gerber, et al, mAbs 1:3, 247-253 (2009); Novellino et al, Cancer Immunol Immunother. 54(3), 187-207 (2005). Franke, et al, Cancer Biother Radiopharm. 2000, 15, 459-76).

The cell binding agents, more preferred antibodies, can be any agents that are able to against tumor cells, virus infected cells, microorganism infected cells, parasite infected cells, autoimmune cells, activated cells, myeloid cells, activated T-cells, B cells, or melanocytes. More specifically the cell binding agents can be any agent/molecule that is able to against any one of the following antigens or receptors: CD3, CD4, CD5, CD6, CD7, CD8, CD9, CD10, CD11a, CD11b, CD11c, CD12w, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49b, CD49c, CD51, CD52, CD53, CD54, CD55, CD56, CD58, CD59, CD61, CD62E, CD62L, CD62P, CD63, CD66, CD68, CD69, CD70, CD72, CD74, CD79, CD79a, CD79b, CD80, CD81, CD82, CD83, CD86, CD87, CD88, CD89, CD90, CD91, CD95, CD96, CD98, CD100, CD103, CD105, CD106, CD109, CD117, CD120, CD125, CD126, CD127, CD133, CD134, CD135, CD138, CD141, CD142, CD143, CD144, CD147, CD151, CD147, CD152, CD154, CD156, CD158, CD163, CD166, CD168, CD174, CD180, CD184, CDw186, CD194, CD195, CD200, CD200a, CD200b, CD209, CD221, CD227, CD235a, CD240, CD262, CD271, CD274, CD276 (B7-H3), CD303, CD304, CD309, CD326, 4-1BB, 5AC, 5T4 (Trophoblast glycoprotein, TPBG, 5T4, Wnt-Activated Inhibitory Factor 1 or WAIF1), Adenocarcinoma antigen, AGS-5, AGS-22M6, Activin receptor-like kinase 1, AFP, AKAP-4, ALK, Alpha intergrin, Alpha v beta6, Amino-peptidase N, Amyloid beta, Androgen receptor, Angiopoietin 2, Angiopoietin 3, Annexin A1, Anthrax toxin protective antigen, Anti-transferrin receptor, AOC3 (VAP-1), B7-H3, *Bacillus anthracis* anthrax, BAFF (B-cell activating factor), B-lymphoma cell, bcr-abl, Bombesin, BORIS, C5, C242 antigen, CA125 (carbohydrate antigen 125, MUC16), CA-IX (or CAIX, carbonic anhydrase 9), CALLA, CanAg, *Canis lupus familiaris* IL31, Carbonic anhydrase IX, Cardiac myosin, CCL1 (C-C motif chemokine 11), CCR4 (C-C chemokine receptor type 4, CD194), CCR5, CD3E (epsilon), CEA (Carcinoembryonic antigen), CEACAM3, CEACAM5 (carcinoembryonic antigen), CFD (Factor D), Ch4D5, Cholecystokinin 2 (CCK2R), CLDN18 (Claudin-18), Clumping factor A, CRIPTO, FCSF1R (Colony stimulating factor 1 receptor, CD115), CSF2 (colony stimulating factor 2, Granulocyte-macrophage colony-stimulating factor (GM-CSF)), CTLA4 (cytotoxic T-lymphocyte-associated protein 4), CTAA16.88 tumor antigen, CXCR4 (CD184), C-X-C chemokine receptor type 4, cyclic ADP ribose hydrolase, Cyclin B1, CYP1B1, Cytomegalovirus, Cytomegalovirus glycoprotein B, Dabigatran, DLL4 (delta-like-ligand 4), DPP4 (Dipeptidyl-peptidase 4), DR5 (Death receptor 5), *E. coli* shiga toxin type-1, *E. coli* shiga toxin type-2, ED-B, EGFL7 (EGF-like domain-containing protein 7), EGFR, EGFRII, EGFRvIII, Endoglin (CD105), Endothelin B receptor, Endotoxin, EpCAM (epithelial cell adhesion molecule), EphA2, Episialin, ERBB2 (Epidermal Growth Factor Receptor 2), ERBB3, ERG (TM-PRSS2 ETS fusion gene), *Escherichia coli*, ETV6-AML, FAP (Fibroblast activation protein alpha), FCGR1, alpha-Fetoprotein, Fibrin II, beta chain, Fibronectin extra domain-B, FOLR (folate receptor), Folate receptor alpha, Folate hydrolase, Fos-related antigen 1.F protein of respiratory syncytial virus, Frizzled receptor, Fucosyl GM1, GD2 ganglioside, G-28 (a cell surface antigen glyvolipid), GD3 idiotype, GloboH, Glypican 3, N-glycolylneuraminic acid, GM3, GMCSF receptor α-chain, Growth differentiation factor 8, GP100, GPNMB (Transmembrane glycoprotein NMB), GUCY2C (Guanylate cyclase 2C, guanylyl cyclase C(GC-C), intestinal Guanylate cyclase, Guanylate cyclase-C receptor, Heat-stable enterotoxin receptor (hSTAR)), Heat shock proteins, Hemagglutinin, Hepatitis B surface antigen, Hepatitis B virus, HER1 (human epidermal growth factor receptor 1), HER2, HER2/neu, HER3 (ERBB-3), IgG4, HGF/SF (Hepatocyte growth factor/scatter factor), HHGFR, HIV-1, Histone complex, HLA-DR (human leukocyte antigen), HLA-DR10, HLA-DRB, HMWMAA, Human chorionic gonadotropin, HNGF, Human scatter factor receptor kinase, HPV E6/E7, Hsp90, hTERT, ICAM-1 (Intercellular Adhesion Molecule 1), Idiotype, IGF1R (IGF-1, insulin-like growth factor 1 receptor), IGHE, IFN-γ, Influenza hemagglutinin, IgE, IgE Fc region, IGHE, IL-1, IL-2 receptor (interleukin 2 receptor), IL-4, IL-5, IL-6, IL-6R (interleukin 6 receptor), IL-9, IL-10, IL-12, IL-13, IL-17, IL-17A, IL-20, IL-22, IL-23, IL31RA, ILGF2 (Insulin-like growth factor 2), Integrins ($\alpha 4$, $\alpha_{IIb}\beta_3$, $\alpha v\beta 3$, $\alpha_4\beta_7$, $\alpha 5\beta 1$, $\alpha 6\beta 4$, $\alpha 7\beta 7$, $\alpha IIB\beta 3$, $\alpha 5\beta 5$, $\alpha v\beta 5$), Interferon gamma-induced protein, ITGA2, ITGB2, KIR2D, LCK, Le, Legumain, Lewis-Y antigen, LFA-1 (Lymphocyte function-associated antigen 1, CD11a), LHRH, LINGO-1, Lipoteichoic acid, LIV1A, LMP2, LTA, MAD-CT-1, MAD-CT-2, MAGE-1, MAGE-2, MAGE-3, MAGE A1, MAGE A3, MAGE 4, MART1, MCP-1, MIF (Macrophage migration inhibitory factor, or glycosylation-inhibiting factor (GIF)), MS4A (membrane-spanning 4-domains subfamily A member 1), MSLN (mesothelin), MUC1 (Mucin 1, cell surface associated (MUC1) or polymorphic epithelial mucin (PEM)), MUC1-KLH, MUC16 (CA125), MCP (monocyte chemotactic protein 1), MelanA/MART1, ML-IAP, MPG, MS4A (membrane-spanning 4-domains subfamily A), MYCN, Myelin-associated glycoprotein, Myostatin, NA17, NARP-1, NCA-90 (granulocyte antigen), Nectin-4 (ASG-22ME), NGF, Neural apoptosis-regulated proteinase 1, NOGO-A, Notch receptor, Nucleolin, Neu oncogene product, NY-BR-1, NY-ESO-1, OX-40, OxLDL (Oxidized low-density lipoprotein), OY-TES1, P21, p53 nonmutant, P97, Page4, PAP, Paratope of anti-(N-glycolylneuraminic acid), PAX3, PAX5, PCSK9, PDCD1 (PD-1, Programmed cell death protein 1, CD279), PDGF-Rα (Alpha-type platelet-derived growth factor receptor), PDGFR-β, PDL-1, PLAC1, PLAP-like testicular alkaline phosphatase, Platelet-derived growth factor receptor beta, Phosphate-sodium co-transporter, PMEL 17, Polysialic acid, Proteinase3 (PR1), Prostatic carcinoma, PS (Phosphatidylserine), Prostatic carcinoma cells, *Pseudomonas aeruginosa*, PSMA, PSA, PSCA, Rabies virus glycoprotein, RHD (Rh polypeptide 1 (RhPI), CD240), Rhesus factor, RANKL, RhoC, Ras mutant, RGS5, ROBO4, Respiratory syncytial virus, RON, Sarcoma translocation breakpoints, SART3, Sclerostin, SLAMF7 (SLAM family member 7), Selectin P, SDC1 (Syndecan 1), sLe(a), Somatomedin C, SIP (Sphingosine-1-phosphate), Somatostatin, Sperm protein 17, SSX2, STEAP1 (six-transmembrane epithelial antigen of the prostate 1), STEAP2, STn, TAG-72 (tumor associated glycoprotein 72), Survivin, T-cell receptor, T cell transmembrane protein, TEM1 (Tumor endothelial marker 1), TENB2, Tenascin C (TN-C), TGF-α, TGF-β (Transforming growth factor beta), TGF-β1, TGF-β2 (Transforming growth factor-beta 2), Tie (CD202b), Tie2, TIM-1 (CDX-014), Tn, TNF, TNF-α, TNFRSF8, TNFRSF10B (tumor necrosis factor receptor superfamily member 10B), TNFRSF13B (tumor necrosis factor receptor superfamily member 13B), TPBG (trophoblast glycoprotein), TRAIL-R1 (Tumor necrosis aposrosis Inducing ligand Receptor 1), TRAILR2 (Death receptor 5 (DR5)), tumor-associated calcium signal transducer 2, tumor specific glycosylation of MUC1, TWEAK receptor, TYRP1 (glycoprotein 75), TRP-2, Tyrosinase, VCAM-1 (CD106), VEGF, VEGF-A, VEGF-2 (CD309), VEGFR-1, VEGFR2, or vimentin, WT1, XAGE 1, or cells expressing any insulin growth factor receptors, or any epidermal growth factor receptors.

In another specific embodiment, the cell-binding ligand-drug conjugates via the hydrophilic linkers of this invention are used for the targeted treatment of cancers. The targeted cancers include, but are not limited, Adrenocortical Carcinoma, Anal Cancer, Bladder Cancer, Brain Tumor (Adult, Brain Stem Glioma, Childhood, Cerebellar Astrocytoma, Cerebral Astrocytoma, Ependymoma, Medulloblastoma, Supratentorial Primitive Neuroectodermal and Pineal Tumors, Visual Pathway and Hypothalamic Glioma), Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Eye Cancer, Intraocular Melanoma, Gallbladder Cancer, Gastric Cancer (Stomach), Germ Cell Tumor, Extragonadal, Gestational Trophoblastic Tumor, Head and Neck Cancer, Hypopharyngeal Cancer, Islet Cell Carcinoma, Kidney Cancer (renal cell cancer), Laryngeal Cancer, Leukemia (Acute Lymphoblastic, Acute Myeloid, Chronic Lymphocytic, Chronic Myelogenous, Hairy Cell), Lip and Oral Cavity Cancer, Liver Cancer, Lung Cancer (Non-Small Cell, Small Cell, Lymphoma (AIDS-Related, Central Nervous System, Cutaneous T-Cell, Hodgkin's Disease, Non-Hodgkin's Disease, Malignant Mesothelioma, Melanoma, Merkel Cell Carcinoma, Metasatic Squamous Neck Cancer with Occult Primary, Multiple Myeloma, and Other Plasma Cell Neoplasms, Mycosis Fungoides, Myelodysplastic Syndrome, Myeloproliferative Disorders, Nasopharyngeal Cancer, Neuroblastoma, Oral Cancer, Oropharyngeal Cancer, Osteosarcoma, Ovarian Cancer (Epithelial, Germ Cell Tumor, Low Malignant Potential Tumor), Pancreatic Cancer (Exocrine, Islet Cell Carcinoma), Paranasal Sinus and Nasal Cavity Cancer, Parathyroid Cancer, Penile Cancer, Pheochromocytoma Cancer, Pituitary Cancer, Plasma Cell Neoplasm, Prostate Cancer Rhabdomyosarcoma, Rectal Cancer, Renal Cell Cancer (kidney cancer), Renal Pelvis and Ureter (Transitional Cell), Salivary Gland Cancer, Sezary Syndrome, Skin Cancer, Skin Cancer (Cutaneous T-Cell Lymphoma, Kaposi's Sarcoma, Melanoma), Small Intestine Cancer, Soft Tissue Sarcoma, Stomach Cancer, Testicular Cancer, Thymoma (Malignant), Thyroid Cancer, Urethral Cancer, Uterine Cancer (Sarcoma), Unusual Cancer of Childhood, Vaginal Cancer, Vulvar Cancer, Wilms' Tumor.

In another specific embodiment, the cell-binding-drug conjugates via the hydrophilic likers of this invention are used in accordance with the compositions and methods for the treatment or prevention of an autoimmune disease. The autoimmune diseases include, but are not limited, Achlorhydra Autoimmune Active Chronic Hepatitis, Acute Disseminated Encephalomyelitis, Acute hemorrhagic leukoencephalitis, Addison's Disease, Agammaglobulinemia, Alopecia areata, Amyotrophic Lateral Sclerosis, Ankylosing Spondylitis, Anti-GBMITBM Nephritis, Antiphospholipid syndrome, Antisynthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaff's encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostomyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease (a type of idiopathic inflammatory bowel diseases), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barre syndrome, Hashimoto's encephalitis, Hashimoto's thyroiditis, Haemolytic anaemia, Henoch-Schonlein purpura, Herpes gestationis, Hidradenitis suppurativa, Hughes syndrome (See Antiphospholipid syndrome), Hypogammaglobulinemia, Idiopathic Inflammatory Demyelinating Diseases, Idiopathic pulmonary fibrosis, Idiopathic thrombocytopenic purpura (See Autoimmune thrombocytopenic purpura), IgA nephropathy (Also Berger's disease), Inclusion body myositis, Inflammatory demyelinating polyneuopathy, Interstitial cystitis, Irritable Bowel Syndrome, Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease (Also Amyotrophic lateral sclerosis), Lupoid hepatitis, Lupus erythematosus, Majeed syndrome, Ménière's disease, Microscopic polyangiitis, Miller-Fisher syndrome, Mixed Connective Tissue Disease, Morphea, Mucha-Habermann disease, Muckle-Wells syndrome, Multiple Myeloma, Multiple Sclerosis, Myasthenia gravis, Myositis, Narcolepsy, Neuromyelitis optica (Devic's Disease), Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with *Streptococcus*), *Paraneoplastic cerebellar degeneration*, Paroxysmal nocturnal hemoglobinuria, Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjögren's syndrome, Spondyloarthropathy, Sticky blood syndrome, Still's Disease, Stiff person syndrome, Subacute bacterial endocarditis, Susac's syndrome, Sweet syndrome, Sydenham Chorea, Sympathetic ophthalmia, Takayasu's arteritis, Temporal arteritis (giant cell arteritis), Tolosa-Hunt syndrome, Transverse Myelitis, Ulcerative Colitis (a type of idiopathic inflammatory bowel diseases), Undifferentiated connective tissue disease, Undifferentiated spondyloarthropathy, Vasculitis, Vitiligo, Wegener's granulomatosis, Wilson's syndrome, Wiskott-Aldrich syndrome In another specific embodiment, a binding molecule used for the conjugate via the hydrophilic linkers of this invention for the treatment or prevention of an autoimmune disease can be, but are not limited to, anti-elastin antibody; Abys against epithelial cells antibody; Anti-Basement Membrane Collagen Type IV Protein antibody; Anti-Nuclear Antibody; Anti ds DNA; Anti ss DNA, Anti Cardiolipin Antibody IgM, IgG; anti-celiac antibody; Anti Phospholipid Antibody IgK, IgG; Anti SM Antibody; Anti Mitochondrial Antibody; Thyroid Antibody; Microsomal Antibody, T-cells antibody; Thyroglobulin Antibody, Anti SCL-70; Anti-Jo; Anti-U.sub.1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody, Anti-ganglioside antibody; Anti-Desmogein 3 antibody; Anti-p62 antibody; Anti-sp100 antibody; Anti-Mitochondrial(M2) antibody; Rheumatoid factor antibody; Anti-MCV antibody; Anti-topoisomerase antibody; Anti-neutrophil cytoplasmic(cANCA) antibody;

In certain preferred embodiments, the binding molecule for the conjugate in the present invention, can bind to both a receptor or a receptor complex expressed on an activated lymphocyte which is associated with an autoimmune disease. The receptor or receptor complex can comprise an immunoglobulin gene superfamily member (e.g. CD2, CD3, CD4, CD8, CD19, CD20, CD22, CD28, CD30, CD33, CD37, CD38, CD56, CD70, CD79, CD79b, CD90, CD125, CD152/CTLA-4, PD-1, or ICOS), a TNF receptor superfamily member (e.g. CD27, CD40, CD95/Fas, CD134/OX40, CD137/4-1BB, INF-R1, TNFR-2, RANK, TACI, BCMA, osteoprotegerin, Apo2/TRAIL-R1, TRAIL-R2, TRAIL-R3, TRAIL-R4, and APO-3), an integrin, a cytokine receptor, a chemokine receptor, a major histocompatibility protein, a lectin (C-type, S-type, or I-type), or a complement control protein.

In another specific embodiment, useful cell binding ligands that are immunospecific for a viral or a microbial antigen are humanized or human monoclonal antibodies. As used herein, the term "viral antigen" includes, but is not limited to, any viral peptide, polypeptide protein (e.g. HIV gp120, HIV nef, RSV F glycoprotein, influenza virus neuramimidase, influenza virus hemagglutinin, HTLV tax, herpes simplex virus glycoprotein (e.g. gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptides including, e.g., LPS and capsular polysaccharide 5/8) that is capable of eliciting an immune response. Examples of antibodies available 1 for the viral or microbial infection include, but are not limited to, Palivizumab which is a humanized anti-respiratory syncytial virus monoclonal antibody for the treatment of RSV infection; PRO542 which is a CD4 fusion antibody for the treatment of HIV infection; Ostavir which is a human antibody for the treatment of hepatitis B virus; PROTVIR which is a humanized IgG.sub.1 antibody for the treatment of cytomegalovirus; and anti-LPS antibodies.

The cell binding molecules-drug conjugates via the hydrophilic linkers of this invention can be used in the treatment of infectious diseases. These infectious diseases include, but are not limited to, *Acinetobacter* infections, Actinomycosis, African sleeping sickness (African trypanosomiasis), AIDS (Acquired immune deficiency syndrome), Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis, *Bacteroides* infection, Balantidiasis, *Baylisascaris* infection, BK virus infection, Black *piedra, Blastocystis hominis* infection, Blastomycosis, Bolivian hemorrhagic fever, *Borrelia* infection, Botulism (and Infant botulism), Brazilian hemorrhagic fever, Brucellosis, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, *Chlamydia, Chlamydophila pneumoniae* infection, Cholera, Chromoblastomycosis, Clonorchiasis, *Clostridium difficile* infection, Coccidioidomycosis, Colorado tick fever, Common cold (Acute viral rhinopharyngitis; Acute coryza), Creutzfeldt-Jakob disease, Crimean-Congo hemorrhagic fever, Cryptococcosis, Cryptosporidiosis, Cutaneous larva migrans, Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum, Fasciolopsiasis, Fasciolosis, Fatal familial insomnia, Filariasis, Food poisoning by *Clostridium perfringens*, Free-living amebic infection, *Fusobacterium* infection, Gas gangrene (Clostridial myonecrosis), Geotrichosis, Gerstmann-Straussler-Scheinker syndrome, Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome, *Helicobacter pylori* infection, Hemolytic-uremic syndrome, Hemorrhagic fever with renal syndrome, Hepatitis A, Hepatitis B, Hepatitis C, Hepatitis D, Hepatitis E, Herpes simplex, Histoplasmosis, Hook-worm infection, Human bocavirus infection, Human *ewingii* ehrlichiosis, Human granulocytic anaplasmosis, Human metapneumovirus infection, Human monocytic ehrlichiosis, Human papillomavirus infection, Human parainfluenza virus infection, Hymenolepiasis, Epstein-Barr Virus Infectious Mononucleosis (Mono), Influenza, Isosporiasis, Kawasaki disease, Keratitis, Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever, Measles, Melioidosis (Whitmore's disease), Meningitis, Meningococcal disease, Metagonimiasis, Microsporidiosis, Molluscum contagiosum, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease, Pertussis (Whooping cough), Plague, Pneumococcal infection, *Pneumocystis* pneumonia, Pneumonia, Poliomyelitis, *Prevotella* infection, Primary amoebic meningoencephalitis, Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsialpox, Rift Valley fever, Rocky mountain spotted fever, Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (*Pityriasis versicolor*), Toxocariasis (Ocular Larva Migrans), Toxocariasis (Visceral Larva Migrans), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, Viral pneumonia, West Nile Fever, White piedra (Tinea blanca), *Yersinia pseudotuberculosis* infection, Yersiniosis, Yellow fever, Zygomycosis.

The cell binding molecule, which is more preferred to be an antibody described in this patent that are against pathogenic strains include, but are not limit, *Acinetobacter baumannii, Actinomyces israelii, Actinomyces gerencseriae* and *Propionibacterium propionicus, Trypanosoma brucei*, HIV (Human immunodeficiency virus), *Entamoeba histolytica, Anaplasma* genus, *Bacillus anthracis, Arcanobacterium haemolyticum*, Junin virus, *Ascaris lumbricoides, Aspergillus* genus, Astroviridae family, *Babesia* genus, *Bacillus cereus*, multiple bacteria, *Bacteroides* genus, *Balantidium coli, Baylisascaris* genus, BK virus, Piedraia hortae, *Blastocystis hominis, Blastomyces dermatitides*, Machupo virus, *Borrelia* genus, *Clostridium botulinum*, Sabia, *Brucella* genus, usually *Burkholderia cepacia* and other *Burkholderia* species, *Mycobacterium ulcerans*, Caliciviridae family, *Campylobacter* genus, usually *Candida albicans* and other *Candida* species, *Bartonella henselae*, Group A *Streptococcus* and *Staphylococcus, Trypanosoma cruzi, Haemophilus ducreyi*, Varicella zoster virus (VZV), *Chlamydia trachomatis, Chlamydophila pneumoniae, Vibrio cholerae, Fonsecaea pedrosoi, Clonorchis sinensis, Clostridium difficile, Coccidioides immitis* and *Coccidioides posadasii*, Colorado tick fever virus, rhinoviruses, coronaviruses, CJD prion, Crimean-Congo hemorrhagic fever virus, *Cryptococcus neoformans, Cryptosporidium* genus, *Ancylostoma braziliense*; multiple parasites, *Cyclospora cayetanensis, Taenia solium*, Cytomegalovirus, Dengue viruses (DEN-1, DEN-2, DEN-3 and DEN-4)—Flaviviruses, *Dientamoeba fragilis, Corynebacterium diphtheriae, Diphyllobothrium, Dracunculus medinensis*, Ebolavirus, *Echinococcus* genus, *Ehrlichia* genus, *Enterobius vermicularis, Enterococcus* genus, Enterovirus genus, *Rickettsia prowazekii*, Parvovirus B19, Human herpesvirus 6 and Human herpesvirus 7, *Fasciolopsis buski, Fasciola hepatica* and *Fasciola gigantica*, FFI prion, Filarioidea superfamily, *Clostridium perfringens, Fusobacterium* genus, *Clostridium perfringens*; other *Clostridium* species, *Geotrichum candidum*, GSS prion, *Giardia intestinalis, Burkholderia mallei, Gnathostoma spinigerum* and *Gnathostoma hispidum, Neisseria gonorrhoeae, Klebsiella granulomatis, Streptococcus pyogenes, Streptococcus agalactiae, Haemophilus influenzae*, Enteroviruses, mainly Coxsackie A virus and Enterovirus 71, Sin Nombre virus, *Helicobacter pylori, Escherichia coli* O157:H7, Bunyaviridae family, Hepatitis A Virus, Hepatitis B Virus, Hepatitis C Virus, Hepatitis D Virus, Hepatitis E Virus, Herpes simplex virus 1, Herpes simplex virus 2, *Histoplasma capsulatum, Ancylostoma duodenale* and *Necator americanus, Hemophilus i influenzae*, Human bocavirus, *Ehrlichia ewingii, Anaplasma phagocytophilum*, Human metapneumovirus, *Ehrlichia chaffeensis*, Human papillomavirus, Human parainfluenza viruses, *Hymenolepis nana* and *Hymenolepis diminuta*, Epstein-Barr Virus, Orthomyxoviridae family, *Isospora belli*, Kingella kingae, *Klebsiella pneumoniae, Klebsiella ozaenas, Klebsiella rhinoscleromotis*, Kuru prion, Lassa virus, *Legionella pneumophila, Legionella pneumophila, Leishmania* genus, *Mycobacterium leprae* and *Mycobacterium lepromatosis, Leptospira* genus, *Listeria monocytogenes, Borrelia burgdorferi* and other *Borrelia* species, *Wuchereria bancrofti* and *Brugia malayi*, Lymphocytic choriomeningitis virus (LCMV), *Plasmodium* genus, Marburg virus, Measles virus, *Burkholderia pseudomallei, Neisseria meningitides, Metagonimus yokagawai, Microsporidia* phylum, Molluscum contagiosum virus (MCV), Mumps virus, *Rickettsia typhi, Mycoplasma pneumoniae*, numerous species of bacteria (Actinomycetoma) and fungi (Eumycetoma), parasitic dipterous fly larvae, *Chlamydia trachomatis* and *Neisseria gonorrhoeae*, vCJD prion, *Nocardia asteroides* and other *Nocardia* species, *Onchocerca volvulus, Paracoccidioides brasiliensis, Paragonimus westermani* and other *Paragonimus* species, *Pasteurella* genus, *Pediculus humanus* capitis, *Pediculus humanus corporis, Phthirus pubis, Bordetella pertussis, Yersinia pestis, Streptococcus pneumoniae, Pneumocystis jirovecii*, Poliovirus, *Prevotella* genus, *Naegleria fowleri*, JC virus, *Chlamydophila psittaci, Coxiella burnetii*, Rabies virus, *Streptobacillus moniliformis* and Spirillum minus, Respiratory syncytial virus, *Rhinosporidium seeberi*, Rhinovirus, *Rickettsia* genus, *Rickettsia akari*, Rift Valley fever virus, *Rickettsia rickettsii*, Rotavirus, Rubella virus, *Salmonella* genus, SARS coronavirus, *Sarcoptes scabiei, Schistosoma* genus, *Shigella* genus, Varicella zoster virus, Variola major or Variola minor, *Sporothrix schenckii, Staphylococcus* genus, *Staphylococcus* genus, *Staphylococcus aureus, Streptococcus pyogenes, Strongyloides stercoralis, Treponema pallidum, Taenia* genus, *Clostridium tetani, Trichophyton* genus, *Trichophyton tonsurans, Trichophyton* genus, *Epidermophyton floccosum, Trichophyton rubrum*, and *Trichophyton mentagrophytes, Trichophyton rubrum, Hortaea werneckii, Trichophyton* genus, *Malassezia* genus, *Toxocara canis* or *Toxocara cati, Toxoplasma gondii, Trichinella spiralis, Trichomonas vaginalis, Trichuris trichiura, Mycobacterium tuberculosis, Francisella tularensis, Ureaplasma urealyticum*, Venezuelan equine encephalitis virus, *Vibrio colerae*, Guanarito virus, West Nile virus, *Trichosporon beigelii, Yersinia pseudotuberculosis, Yersinia enterocolitica*, Yellow fever virus, Mucorales order (Mucormycosis) and Entomophthorales order (Entomophthoramycosis), *Pseudomonas aeruginosa, Campylobacter* (*Vibrio*) fetus, *Aeromonas hydrophila, Edwardsiella tarda, Yersinia pestis, Shigella dysenteriae, Shigella flexneri, Shigella sonnei, Salmonella typhimurium, Treponema pertenue, Treponema carateneum, Borrelia vincentii, Borrelia burgdorferi, Leptospira icterohemorrhagiae, Pneumocystis carinii, Brucella abortus, Brucella suis, Brucella melitensis, Mycoplasma* spp., *Rickettsia prowazeki, Rickettsia tsutsugumushi, Clamydia* spp.; pathogenic fungi (*Aspergillus fumigatus, Candida albicans, Histoplasma capsulatum*); protozoa (Entomoeba *histolytica, Trichomonas* tenas, *Trichomonas hominis*, Tryoanosoma gambiense, *Trypanosoma* rhodesiense, *Leishmania donovani, Leishmania tropica, Leishmania braziliensis, Pneumocystis pneumonia, Plasmodium vivax, Plasmodium falciparum, Plasmodium malaria*); or Helminiths (*Schistosoma japonicum, Schistosoma mansoni, Schistosoma haematobium*, and hookworms).

Other antibodies as cell binding ligands used in this invention for treatment of viral disease include, but are not limited to, antibodies against antigens of pathogenic viruses, including as examples and not by limitation: Poxyiridae, Herpesviridae, Adenoviridae, Papovaviridae, Enteroviridae, Picomaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Non-A/Non-B Hepatitis virus, Rhinoviridae, Coronaviridae, Rotoviridae, Oncovirus [such as, HBV (Hepatocellular carcinoma), HPV (Cervical cancer, Anal cancer), Kaposi's sarcoma-associated herpesvirus (Kaposi's sarcoma), Epstein-Barr virus (Nasopharyngeal carcinoma, Burkitt's lymphoma, Primary central nervous system lymphoma), MCPyV (Merkel cell cancer), SV40 (Simian virus 40), HCV (Hepatocellular carcinoma), HTLV-I (Adult T-cell leukemia/lymphoma)], Immune disorders caused virus: [such as Human Immunodeficiency Virus (AIDS)]; Central nervous system virus: [such as, JCV (Progressive multifocal leukoencephalopathy), MeV (Subacute sclerosing panencephalitis), LCV (Lymphocytic choriomeningitis), Arbovirus encephalitis, Orthomyxoviridae (probable) (Encephalitis lethargica), RV (Rabies), Chandipura virus, Herpesviral meningitis, Ramsay Hunt syndrome type II; Poliovirus (Poliomyelitis, Post-polio syndrome), HTLV-I (Tropical spastic paraparesis)]; Cytomegalovirus (Cytomegalovirus retinitis, HSV (Herpetic keratitis)); Cardiovascular virus [such as CBV (Pericarditis, Myocarditis)]; Respiratory system/acute viral nasopharyngitis/viral pneumonia: [Epstein-Barr virus (EBV infection/Infectious mononucleosis), Cytomegalovirus; SARS coronavirus (Severe acute respiratory syndrome) Orthomyxoviridae: Influenzavirus A/B/C (Influenza/Avian influenza), Paramyxovirus: Human parainfluenza viruses (Parainfluenza), RSV (Human respiratory syncytial virus), hMPV]; Digestive system virus [MuV (Mumps), Cytomegalovirus (Cytomegalovirus esophagitis); Adenovirus (Adenovirus infection); Rotavirus, Norovirus, Astrovirus, Coronavirus; HBV (Hepatitis B virus), CBV, HAV (Hepatitis A virus), HCV (Hepatitis C virus), HDV (Hepatitis D virus), HEV (Hepatitis E virus), HGV (Hepatitis G virus)]; Urogenital virus [such as, BK virus, MuV (Mumps)].

According to a further object, the present invention also concerns pharmaceutical compositions comprising the conjugate via the hydrophilic linkers of the invention together with a pharmaceutically acceptable carrier, diluent, or excipient for treatment of cancers, infections or autoimmune disorders. The method for treatment of cancers, infections and autoimmune disorders can be practiced in vitro, in vivo, or ex vivo. Examples of in vitro uses include treatments of cell cultures in order to kill all cells except for desired variants that do not express the target antigen; or to kill variants that express undesired antigen. Examples of ex vivo uses include treatments of hematopoietic stem cells (HSC) prior to the performance of the transplantation (HSCT) into the same patient in order to kill diseased or malignant cells. For instance, clinical ex vivo treatment to remove tumour cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent graft-versus-host disease, can be carried out as follows. Bone marrow is harvested from the patient or other individual and then incubated in medium containing serum to which is added the conjugate of the invention, concentrations range from about 1 pM to 0.1 mM, for about 30 minutes to about 48 hours at about 37° C. The exact conditions of concentration and time of incubation (=dose) are readily determined by the skilled clinicians.

After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the conjugate via the linkers of the invention will be supplied as solutions or as a lyophilized solid that can be redissolved in sterile water for injection. Examples of suitable protocols of conjugate administration are as follows. Conjugates are given weekly for 8 weeks as an i.v. bolus. Bolus doses are given in 50 to 500 ml of normal saline to which human serum albumin (e.g. 0.5 to 1 mL of a concentrated solution of human serum albumin, 100 mg/mL) can be added. Dosages will be about 50 µg to 20 mg/kg of body weight per week, i.v. (range of 10 µg to 200 mg/kg per injection). 8 weeks after treatment, the patient may receive a second course of treatment. Specific clinical protocols with regard to route of administration, excipients, diluents, dosages, times, etc., can be determined by the skilled clinicians.

Examples of medical conditions that can be treated according to the in vivo or ex vivo methods of killing selected cell populations include malignancy of any types of cancer, autoimmune diseases, graft rejections, and infections (viral, bacterial or parasite).

The amount of a conjugate which is required to achieve the desired biological effect, will vary depending upon a number of factors, including the chemical characteristics, the potency, and the bioavailability of the conjugates, the type of disease, the species to which the patient belongs, the diseased state of the patient, the route of administration, all factors which dictate the required dose amounts, delivery and regimen to be administered.

In general terms, the conjugates via the linkers of this invention may be provided in an aqueous physiological buffer solution containing 0.1 to 10% w/v conjugates for parenteral administration. Typical dose ranges are from 1 µg/kg to 0.1 g/kg of body weight per day; a preferred dose range is from 0.01 mg/kg to 20 mg/kg of body weight per day or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the compound by the chosen delivery route, and the speed (bolus or continuous infusion) and schedule of administrations (number of repetitions in a given period of time).

The conjugates via the linkers of the present invention are also capable of being administered in unit dose forms, wherein the term "unit dose" means a single dose which is capable of being administered to a patient, and which can be readily handled and packaged, remaining as a physically and chemically stable unit dose comprising either the active conjugate itself, or as a pharmaceutically acceptable composition, as described hereinafter. As such, typical total daily/weekly/biweekly/monthly dose ranges are from 0.01 to 100 mg/kg of body weight. By way of general guidance, unit doses for humans range from 1 mg to 3000 mg per day, or per week, per two week or per month. Preferably the unit dose range is from 1 to 500 mg administered one to four times a day, and even more preferably from 10 mg to 500 mg, once a day. Conjugates provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasal, particularly in the form of powders, nasal drops, or aerosols; or dermally, for example, topically in ointments, creams, lotions, gels or sprays, or via trans-dermal patches.

Drugs/Cytotoxic Agents

Drugs that can be conjugated to a cell-binding molecule in the present invention are small molecule drugs including cytotoxic agents, which can be linked to or after they are modified for linkage to the cell-binding agent. A "small molecule drug" is broadly used herein to refer to an organic, inorganic, or organometallic compound that may have a molecular weight of for example 100 to 1800, more suitably from 120 to 1400. Small molecule drugs are well characterized in the art, such as in WO05058367A2, and in U.S. Pat. No. 4,956,303, among others and are incorporated in their entirety by reference. The drugs include known drugs and those that may become known drugs.

Drugs that are known include, but not limited to,

1). Chemotherapeutic agents: a). Alkylating agents: such as Nitrogen mustards: chlorambucil, chlornaphazine, cyclophosphamide, dacarbazine, estramustine, ifosfamide, mechlorethamine, mechlorethamine oxide hydrochloride, mannomustine, mitobronitol, melphalan, mitolactol, pipobroman, novembichin, phenesterine, prednimustine, thiotepa, trofosfamide, uracil mustard; CC-1065 (including its adozelesin, carzelesin and bizelesin synthetic analogues); Duocarmycin (including the synthetic analogues, KW-2189 and CBI-TMI); Benzodiazepine dimers (e.g., dimmers of pyrrolobenzodiazepine (PBD) or tomaymycin, indolinobenzodiazepines, imidazobenzothiadiazepines, or oxazolidinobenzodiazepines); Nitrosoureas: (carmustine, lomustine, chlorozotocin, fotemustine, nimustine, ranimustine); Alkylsulphonates: (busulfan, treosulfan, improsulfan and piposulfan); Triazenes: (dacarbazine); Platinum containing compounds: (carboplatin, cisplatin, oxaliplatin); aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine]; b). Plant Alkaloids: such as Vinca alkaloids: (vincristine, vinblastine, vindesine, vinorelbine, navelbin); Taxoids: (paclitaxel, docetaxol) and their analogs, Maytansinoids (DM1, DM2, DM3, DM4, maytansine and ansamitocins) and their analogs, cryptophycins (particularly cryptophycin 1 and cryptophycin 8); epothilones, eleutherobin, discodermolide, bryostatins, dolostatins, auristatins, tubulysins, cephalostatins; pancratistatin; a sarcodictyin; spongistatin; c). DNA Topoisomerase Inhibitors: such as [Epipodophyllins: (9-aminocamptothecin, camptothecin, crisnatol, daunomycin, etoposide, etoposide phosphate, irinotecan, mitoxantrone, novantrone, retinoic acids (retinols), teniposide, topotecan, 9-nitrocamptothecin (RFS 2000)); mitomycins: (mitomycin C)]; d). Anti-metabolites: such as {[Anti-folate: DHFR inhibitors: (methotrexate, trimetrexate, denopterin, pteropterin, aminopterin (4-aminopteroic acid) or the other folic acid analogues); IMP dehydrogenase Inhibitors: (mycophenolic acid, tiazofurin, ribavirin, EICAR); Ribonucleotide reductase Inhibitors: (hydroxyurea, deferoxamine)]; [Pyrimidine analogs: Uracil analogs: (ancitabine, azacitidine, 6-azauridine, capecitabine (Xeloda), carmofur, cytarabine, dideoxyuridine, doxifluridine, enocitabine, 5-Fluorouracil, floxuridine, ratitrexed (Tomudex)); Cytosine analogs:

(cytarabine, cytosine arabinoside, fludarabine); Purine analogs: (azathioprine, fludarabine, mercaptopurine, thiamiprine, thioguanine)]; folic acid replenisher, such as frolinic acid); e). Hormonal therapies: such as (Receptor antagonists: [Anti-estrogen: (megestrol, raloxifene, tamoxifen); LHRH agonists: (goscrclin, leuprolide acetate); Anti-androgens: (bicalutamide, flutamide, calusterone, dromostanolone propionate, epitiostanol, goserelin, leuprolide, mepitiostane, nilutamide, testolactone, trilostane and other androgens inhibitors)]; Retinoids/Deltoids: [Vitamin D3 analogs: (CB 1093, EB 1089 KH 1060, cholecalciferol, ergocalciferol); Photodynamic therapies: (verteporfin, phthalocyanine, photosensitizer Pc4, demethoxy-hypocrellin A); Cytokines: (Interferon-alpha, Interferon-gamma, tumor necrosis factor (TNFs), human proteins containing a TNF domain)]}; f). Kinase inhibitors, such as BIBW 2992 (anti-EGFR/Erb2), imatinib, gefitinib, pegaptanib, sorafenib, dasatinib, sunitinib, erlotinib, nilotinib, lapatinib, axitinib, pazopanib. vandetanib, E7080 (anti-VEGFR2), mubritinib, ponatinib (AP24534), bafetinib (INNO-406), bosutinib (SKI-606), cabozantinib, vismodegib, iniparib, ruxolitinib, CYT387, axitinib, tivozanib, sorafenib, bevacizumab, cetuximab, Trastuzumab, Ranibizumab, Panitumumab, ispinesib; g). antibiotics, such as the enediyne antibiotics (e.g. calicheamicins, especially calicheamicin γ1, δ1, α1 and β1, see, e.g., J. Med. Chem., 39 (11), 2103-2117 (1996), Angew Chem Intl. Ed. Engl. 33:183-186 (1994); dynemicin, including dynemicin A and deoxydynemicin; esperamicin, kedarcidin, C-1027, maduropeptin, as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin and deoxydoxorubicin, epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; f). Others: such as Polyketides (acetogenins), especially bullatacin and bullatacinone; gemcitabine, epoxomicins (e. g. carfilzomib), bortezomib, thalidomide, lenalidomide, pomalidomide, tosedostat, zybrestat, PLX4032, STA-9090, Stimuvax, allovectin-7, Xegeva, Provenge, Yervoy, Isoprenylation inhibitors (such as Lovastatin), Dopaminergic neurotoxins (such as 1-methyl-4-phenylpyridinium ion), Cell cycle inhibitors (such as staurosporine), Actinomycins (such as Actinomycin D, dactinomycin), Bleomycins (such as bleomycin A2, bleomycin B2, peplomycin), Anthracyclines (such as daunorubicin, doxorubicin (adriamycin), idarubicin, epirubicin, pirarubicin, zorubicin, mtoxantrone, MDR inhibitors (such as verapamil), $Ca^{2+}$ ATPase inhibitors (such as thapsigargin), Histone deacetylase inhibitors (Vorinostat, Romidepsin, Panobinostat, Valproic acid, Mocetinostat (MGCD0103), Belinostat, PCI-24781, Entinostat, SB939, Resminostat, Givinostat, AR-42, CUDC-101, sulforaphane, Trichostatin A); Thapsigargin, Celecoxib, glitazones, epigallocatechin gallate, Disulfiram, Salinosporamide A.; Anti-adrenals, such as aminoglutethimide, mitotane, trilostane; aceglatone; aldophosphamide glycoside; aminolevulinic acid; amsacrine; arabinoside, bestrabucil; bisantrene; edatraxate; defofamine; demecolcine; diaziquone; eflornithine (DFMO), elfomithine; elliptinium acetate, etoglucid; gallium nitrate; gacytosine, hydroxyurea; ibandronate, lentinan; lonidamine; mitoguazone; mitoxantrone, mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verrucarin A, roridin A and anguidine); urethane, siRNA, antisense drugs, and a nucleolytic enzyme.

2). An anti-autoimmune disease agent includes, but is not limited to, cyclosporine, cyclosporine A, aminocaproic acid, azathioprine, bromocriptine, chlorambucil, chloroquine, cyclophosphamide, corticosteroids (e.g. amcinonide, betamethasone, budesonide, hydrocortisone, flunisolide, fluticasone propionate, fluocortolone danazol, dexamethasone, Triamcinolone acetonide, beclometasone dipropionate), DHEA, enanercept, hydroxychloroquine, infliximab, meloxicam, methotrexate, mofetil, mycophenylate, prednisone, sirolimus, tacrolimus.

3). An anti-infectious disease agent includes, but is not limited to, a). Aminoglycosides: amikacin, astromicin, gentamicin (netilmicin, sisomicin, isepamicin), hygromycin B, kanamycin (amikacin, arbekacin, bekanamycin, dibekacin, tobramycin), neomycin (framycetin, paromomycin, ribostamycin), netilmicin, spectinomycin, streptomycin, tobramycin, verdamicin; b). Amphenicols: azidamfenicol, chloramphenicol, florfenicol, thiamphenicol; c). Ansamycins: geldanamycin, herbimycin; d). Carbapenems: biapenem, doripenem, ertapenem, imipenem/cilastatin, meropenem, panipenem; e). Cephems: carbacephem (loracarbef), cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin (cefoxitin, cefotetan, cefmetazole), oxacephem (flomoxef, latamoxef); f). Glycopeptides: bleomycin, vancomycin (oritavancin, telavancin), teicoplanin (dalbavancin), ramoplanin; g). Glycylcyclines: e. g. tigecycline; g). β-Lactamase inhibitors: penam (sulbactam, tazobactam), clavam (clavulanic acid); i). Lincosamides: clindamycin, lincomycin; j). Lipopeptides: daptomycin, A54145, calcium-dependent antibiotics (CDA); k). Macrolides: azithromycin, cethromycin, clarithromycin, dirithromycin, erythromycin, flurithromycin, josamycin, ketolide (telithromycin, cethromycin), midecamycin, miocamycin, oleandomycin, rifamycins (rifampicin, rifampin, rifabutin, rifapentine), rokitamycin, roxithromycin, spectinomycin, spiramycin, tacrolimus (FK506), troleandomycin, telithromycin; l). Monobactams: aztreonam, tigemonam; m). Oxazolidinones: linezolid; n). Penicillins: amoxicillin, ampicillin (pivampicillin, hetacillin, bacampicillin, metampicillin, talampicillin), azidocillin, azlocillin, benzylpenicillin, benzathine benzylpenicillin, benzathine phenoxymethyl-penicillin, clometocillin, procaine benzylpenicillin, carbenicillin (carindacillin), cloxacillin, dicloxacillin, epicillin, flucloxacillin, mecillinam (pivmecillinam), mezlocillin, meticillin, nafcillin, oxacillin, penamecillin, penicillin, pheneticillin, phenoxymethylpenicillin, piperacillin, propicillin, sulbenicillin, temocillin, ticarcillin; o). Polypeptides: bacitracin, colistin, polymyxin B; p). Quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin; q). Streptogramins: pristinamycin, quinupristin/dalfopristin); r). Sulfonamides: mafenide, prontosil, sulfacetamide, sulfamethizole, sulfanilimide, sulfasalazine, sulfisoxazole, trimethoprim, trimethoprim-sulfamethoxazole (co-trimoxazole); s). Steroid antibacterials: e.g. fusidic acid; t). Tetracyclines: doxycycline, chlortetracycline, clomocycline, demeclocycline, lymecycline, meclocycline, metacycline, minocycline, oxytetracycline, penimepicycline, rolitetracycline, tetracycline, glycylcyclines (e.g. tigecycline); u). Other types of antibiotics: annonacin, arsphenamine, bactoprenol inhibitors (Bacitracin), DADAUIAR inhibitors (cycloserine), dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors (e. g. fosfomycin), nitrofurantoin, paclitaxel, platensimycin, pyrazinamide, quinupristin/dalfopristin, rifampicin (rifampin), tazobactam tinidazole, uvaricin;

4). Anti-viral drugs: a). Entry/fusion inhibitors: aplaviroc, maraviroc, vicriviroc, gp41 (enfuvirtide), PRO 140, CD4 (ibalizumab); b). Integrase inhibitors: raltegravir, elvitegravir, globoidnan A; c). Maturation inhibitors: bevirimat, vivecon; d). Neuraminidase inhibitors: oseltamivir, zanamivir, peramivir; e). Nucleosides & nucleotides: abacavir, aciclovir, adefovir, amdoxovir, apricitabine, brivudine, cidofovir, clevudine, dexelvucitabine, didanosine (ddI), elvucitabine, emtricitabine (FTC), entecavir, famciclovir, fluorouracil (5-FU), 3'-fluoro-substituted 2',3'-dideoxynucleoside analogues (e.g. 3'-fluoro-2',3'-dideoxythymidine (FLT) and 3'-fluoro-2',3'-dideoxyguanosine (FLG), fomivirsen, ganciclovir, idoxuridine, lamivudine (3TC), 1-nucleosides (e.g. β-1-thymidine and β-1-2'-deoxycytidine), penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT); f). Non-nucleosides: amantadine, ateviridine, capravirine, diarylpyrimidines (etravirine, rilpivirine), delavirdine, docosanol, emivirine, efavirenz, foscarnet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine; g). Protease inhibitors: amprenavir, atazanavir, boceprevir, darunavir, fosamprenavir, indinavir, lopinavir, nelfinavir, pleconaril, ritonavir, saquinavir, telaprevir (VX-950), tipranavir; h). Other types of anti-virus drugs: abzyme, arbidol, calanolide a, ceragenin, cyanovirin-n, diarylpyrimidines, epigallocatechin gallate (EGCG), foscarnet, griffithsin, taribavirin (viramidine), hydroxyurea, KP-1461, miltefosine, pleconaril, portmanteau inhibitors, ribavirin, seliciclib.

5). The drugs used for conjugates via a hydrophilic linker of the present invention also include radioisotopes. Examples of radioisotopes (radionuclides) are $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. Radioisotope labeled antibodies are useful in receptor targeted imaging experiments or can be for targeted treatment such as with the antibody-drug conjugates of the invention (Wu et al (2005) Nature Biotechnology 23(9): 1137-1146). The cell binding molecules, e.g. an antibody can be labeled with ligand reagents through the hydrophilic linkers of the present patent that bind, chelate or otherwise complex a radioisotope metal, using the techniques described in Current Protocols in Immunology, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex.).

6). The pharmaceutically acceptable salts, acids or derivatives of any of the above drugs.

In another embodiment, the drug in the Formula (II) and (IV) can a chromophore molecule, for which the conjugate can be used for detection, monitoring, or study the interaction of the cell binding molecule with a target cell. Chromophore molecules are a compound that have the ability to absorb a kind of light, such as UV light, florescent light, IR light, near IR light, visual light; A chromatophore molecule includes a class or subclass of xanthophores, erythrophores, iridophores, leucophores, melanophores, and cyanophores; a class or subclass of fluorophore molecules which are fluorescent chemical compounds re-emitting light upon light; a class or subclass of visual phototransduction molecules; a class or subclass of photophore molecules; a class or subclass of luminescence molecules; and a class or subclass of luciferin compounds.

The chromophore molecule can be selected from, but not limited, Non-protein organic fluorophores, such as: Xanthene derivatives (fluorescein, rhodamine, Oregon green, eosin, and Texas red); Cyanine derivatives: (cyanine, indocarbocyanine, oxacarbocyanine, thiacarbocyanine, and merocyanine); Squaraine derivatives and ring-substituted squaraines, including Seta, SeTau, and Square dyes; Naphthalene derivatives (dansyl and prodan derivatives); Coumarin derivatives; Oxadiazole derivatives (pyridyloxazole, nitrobenzoxadiazole and benzoxadiazole); Anthracene derivatives (anthraquinones, including DRAQ5, DRAQ7 and CyTRAK Orange); Pyrene derivatives (cascade blue, etc); Oxazine derivatives (Nile red, Nile blue, cresyl violet, oxazine 170 etc). Acridine derivatives (proflavin, acridine orange, acridine yellow etc). Arylmethine derivatives (auramine, crystal violet, malachite green). Tetrapyrrole derivatives (porphin, phthalocyanine, bilirubin).

Or a chromophore molecule can be selected from any analogs and derivatives of the following fluorophore compounds: CF dye (Biotium), DRAQ and CyTRAK probes (BioStatus), BODIPY (Invitrogen), Alexa Fluor (Invitrogen), DyLight Fluor (Thermo Scientific, Pierce), Atto and Tracy (Sigma Aldrich), FluoProbes (Interchim), Abberior Dyes (Abberior), DY and MegaStokes Dyes (Dyomics), Sulfo Cy dyes (Cyandye), HiLyte Fluor (AnaSpec), Seta, SeTau and Square Dyes (SETA BioMedicals), Quasar and Cal Fluor dyes (Biosearch Technologies), SureLight Dyes (APC, RPEPerCP, Phycobilisomes)(Columbia Biosciences), APC, APCXL, RPE, BPE (Phyco-Biotech);

Examples of the widely used fluorophore compounds which are reactive or conjugatable with the linkers of the invention are: Allophycocyanin (APC), Aminocoumarin, APC-Cy7 conjugates, BODIPY-FL, Cascade Blue, Cy2, Cy3, Cy3.5, Cy3B, Cy5, Cy5.5, Cy7, Fluorescein, FluorX, Hydroxycoumarin, Lissamine Rhodamine B, Lucifer yellow, Methoxycoumarin, NBD, Pacific Blue, Pacific Orange, PE-Cy5 conjugates, PE-Cy7 conjugates, PerCP, R-Phycoerythrin(PE), Red 613, Seta-555-Azide, Seta-555-DBCO, Seta-555-NHS, Seta-580-NHS, Seta-680-NHS, Seta-780-NHS, Seta-APC-780, Seta-PerCP-680, Seta-R-PE-670, SeTau-380-NHS, SeTau-405-Maleimide, SeTau-405-NHS, SeTau-425-NHS, SeTau-647-NHS, Texas Red, TRITC, Tru-Red, X-Rhodamine.

The fluorophore compounds that can be linked to the linkers of the invention for study of nucleic acids or proteins are selected from the following compounds or their derivatives: 7-AAD (7-aminoactinomycin D, CG-selective), Acridine Orange, Chromomycin A3, CyTRAK Orange (Biostatus, red excitation dark), DAPI, DRAQ5, DRAQ7, Ethidium Bromide, Hoechst33258, Hoechst33342, LDS 751, Mithramycin, Propidiumlodide (PI), SYTOX Blue, SYTOX Green, SYTOX Orange, Thiazole Orange, TO-PRO: Cyanine Monomer, TOTO-1, TO-PRO-1, TOTO-3, TO-PRO-3, YOSeta-1, YOYO-1. The fluorophore compounds that can be linked to the linkers of the invention for study cells are selected from the following compounds or their derivatives: DCFH (2'7'Dichorodihydro-fluorescein, oxidized form), DHR (Dihydrorhodamine 123, oxidized form, light catalyzes oxidation), Fluo-3 (AM ester. pH>6), Fluo-4 (AM ester. pH 7.2), Indo-1 (AM ester, low/high calcium (Ca2+)), SNARF (pH 6/9). The preferred fluorophore compounds that can be linked to the linkers of the invention for study proteins/antibodies are selected from the following compounds or their derivatives: Allophycocyanin (APC), AmCyan1 (tetramer, Clontech), AsRed2 (tetramer, Clontech), Azami Green (monomer, MBL), Azurite, B-phycoerythrin (BPE), Cerulean, CyPet, DsRed monomer (Clontech), DsRed2 ("RFP", Clontech), EBFP, EBFP2, ECFP, EGFP (weak dimer, Clontech), Emerald (weak dimer, Invitrogen), EYFP (weak dimer, Clontech), GFP (S65A mutation), GFP (S65C mutation), GFP (S65L mutation), GFP (S65T mutation), GFP (Y66F mutation), GFP (Y66H mutation), GFP (Y66W mutation), GFPuv, HcRed1, J-Red, Katusha, Kusabira Orange (monomer, MBL), mCFP, mCherry, mCitrine, Midoriishi Cyan (dimer, MBL), mKate (TagFP635, monomer, Evrogen), mKeima-Red (monomer, MBL), mKO, mOrange, mPlum, mRaspberry, mRFP1 (monomer, Tsien lab), mStrawberry, mTFP1, mTurquoise2, P3 (phycobilisome complex), Peridinin Chlorophyll (PerCP), R-phycoerythrin (RPE), T-Sapphire, TagCFP (dimer, Evrogen), TagGFP (dimer, Evrogen), TagRFP (dimer, Evrogen), TagYFP (dimer, Evrogen), tdTomato (tandem dimer), Topaz, TurboFP602 (dimer, Evrogen), TurboFP635 (dimer, Evrogen), TurboGFP (dimer, Evrogen), TurboRFP (dimer, Evrogen), TurboYFP (dimer, Evrogen), Venus, Wild Type GFP, YPet, ZsGreen1 (tetramer, Clontech), ZsYellow1 (tetramer, Clontech).

In yet another embodiment, the preferred cytotoxic agents that conjugated to a cell-binding molecule via a hydrophilic linker of this patent are tubulysins, maytansinoids, taxanoids (taxanes), CC-1065 analogs, daunorubicin and doxorubicin compounds, benzodiazepine dimers (e.g., dimers of pyrrolobenzodiazepine (PBD), tomaymycin, anthramycin, indolinobenzodiazepines, imidazobenzothiadiazepines, or oxazolidinobenzodiazepines), calicheamicins and the enediyne antibiotics, actinomycin, azaserines, bleomycins, epirubicin, tamoxifen, idarubicin, dolastatins, auristatins (e.g. monomethyl auristatin E, MMAE, MMAF, auristatin PYE, auristatin TP, Auristatins 2-AQ, 6-AQ, EB (AEB), and EFP (AEFP)), duocarmycins, thiotepa, vincristines, hemiasterlins, nazumamides, microginins, radiosumins, alterobactins, microsclerodermins, theonellamides, esperamicins, PNU-159682, and their analogues and derivatives above thereof.

Tubulysins that are preferred for conjugation in the present invention are well known in the art and can be isolated from natural sources according to known methods or prepared synthetically according to known methods (e. g. Balasubramanian, R.; et al. J. Med. Chem., 2009, 52, 238-240. Wipf, P.; et al. Org. Lett., 2004, 6, 4057-4060. Pando, O.; et al. J. Am. Chem. Soc., 2011, 133, 7692-7695. Reddy, J. A.; et al. Mol. Pharmaceutics, 2009, 6, 1518-1525. Raghavan, B.; et al. J. Med. Chem., 2008, 51, 1530-1533. Patterson, A. W.; et al. J. Org. Chem., 2008, 73, 4362-4369. Pando, O.; et al. Org. Lett., 2009, 11 (24), pp 5567-5569. Wipf, P.; et al. Org. Lett., 2007, 9 (8), 1605-1607. Friestad, G. K.; Org. Lett., 2004, 6, pp 3249-3252. Hillary M. Peltier, H. M.; et al. J. Am. Chem. Soc., 2006, 128, 16018-16019. Chandrasekhar, S.; et al. J. Org. Chem., 2009, 74, 9531-9534. Liu, Y.; et al. Mol. Pharmaceutics, 2012, 9, 168-175. Friestad, G. K.; et al. Org. Lett., 2009, 11, 1095-1098. Kubicek, K.; et al., Angew Chem Int Ed Engl, 2010. 49: p. 4809-12. Chai, Y.; et al., Chem Biol, 2010, 17: 296-309. Ullrich, A.; et al., Angew Chem Int Ed Engl, 2009, 48, 4422-5. Sani, M.; et al. Angew Chem Int Ed Engl, 2007, 46, 3526-9. Domling, A.; et al., Angew Chem Int Ed Engl, 2006. 45, 7235-9. Patent applications: Zanda, M.; et al, Can. Pat. Appl. CA 2710693 (2011). Chai, Y.; et al. Eur. Pat. Appl. 2174947 (2010), PCT WO 2010034724. Leamon, C.; et al, PCT WO 2010033733, WO 2009002993. Ellman, J.; et al, PCT WO 2009134279; PCT WO 2009012958, US appl. 20110263650, 20110021568, Matschiner, G.; et al, PCT WO 2009095447.Vlahov, I.; et al, PCT WO 2009055562, WO 2008112873. Low, P.; et al, PCT WO 2009026177. Richter, W., PCT WO 2008138561. Kjems, J.; et al, PCT WO 2008125116. Davis, M.; et al, PCT WO 2008076333. Diener, J.; et al, U.S. Pat. Appl. 20070041901, WO 2006096754. Matschiner, G.; et al, PCT WO 2006056464. Vaghefi, F.; et al, 5 PCT WO 2006033913. Doemling, A., Ger. Offen. DE 102004030227; PCT WO 2004005327; WO 2004005326; WO2004005269. Stanton, M.; et al, U.S. Pat. Appl. Publ. 20040249130. Hoefle, G.; et al, Ger. Offen. DE 10254439; DE 10241152; DE 10008089. Leung, D.; et al, WO 2002077036. Reichenbach, H.; et al, Ger. Offen. DE 19638870; Wolfgang, R.; US 20120129779, Chen, H., US appl. 20110027274. The preferred structure of tubulysins for conjugation of cell binding molecules are described in the patent application of PCT/IB2012/053554

Calicheamicins and their related enediyne antibiotics that are preferred for cell-binding molecule-drug conjugates of this patent are described in: Nicolaou, K. C. et al, Science 1992, 256, 1172-1178; Proc. Natl. Acad. Sci USA. 1993, 90, 5881-5888), U.S. Pat. Nos. 4,970,198; 5,053,394; 5,108, 912; 5,264,586; 5,384,412; 5,606,040; 5,712,374; 5,714, 586; 5,739,116; 5,770,701; 5,770,710; 5,773,001; 5,877, 296; 6,015,562; 6,124,310; 8,153,768.

Maytansinoids that are preferred to be used in the present invention including maytansinol and maytansinol analogues are described in U.S. Pat. Nos. 4,256,746, 4,361,650, 4,307, 016, 4,294,757, 4,294,757, 4,371,533, 4,424,219, 4,331,598, 4,450,254, 4,364,866, 4,313,946, 4,315,929 4,362,663, 4,322,348, 4,371,533, 4,424,219, 5,208,020, 5,416,064, 5,208,020; 5,416,064; 6,333,410; 6,441,163; 6,716,821; 7,276,497, 7,301,019, 7,303,749, 7,368,565, 7,411,063, 7,851,432, and 8,163,888.

Taxanes, which includes Paclitaxel (Taxol), a cytotoxic natural product, and docetaxel (Taxotere), a semi-synthetic derivative, and their analogs which are preferred for conjugation via the hydrophilic linkers of the present patent are exampled in: K C. Nicolaou et al., J. Am. Chem. Soc. 117, 2409-2420, (1995); Ojima et al, J. Med. Chem. 39:3889-3896 (1996); 40:267-278 (1997); 45, 5620-5623 (2002); Ojima et al., Proc. Natl. Acad. Sci., 96:4256-4261 (1999; Kim et al., Bull. Korean Chem. Soc., 20, 1389-1390 (1999); Miller, et al. J. Med. Chem., 47, 4802-4805(2004); U.S. Pat. No. 5,475,011 5,728,849, 5,811,452; 6,340,701; 6,372,738; 6,391,913; 6,436,931; 6,589,979; 6,596,757; 6,706,708; 7,008,942; 7,186,851; 7,217,819; 7,276,499; 7,598,290; and 7,667,054.

CC-1065 analogues and doucarmycin analogs are also preferred to be used for a conjugate with the hydrophilic linkers of the present patent. The examples of the CC-1065 analogues and doucarmycin analogs as well as their synthesis are described in: e.g. Warpehoski et al, J. Med. Chem. 31:590-603 (1988), D. Boger et al., J. Org. Chem; 66; 6654-6661, 2001; U.S. Pat. Nos. 4,169,888, 4,391,904, 4,671,958, 4,816,567, 4,912,227, 4,923,990, 4,952,394, 4,975,278, 4,978,757, 4,994,578, 5,037,993, 5,070,092, 5,084,468, 5,101,038, 5,117,006, 5,137,877, 5,138,059, 5,147,786, 5,187,186, 5,223,409, 5,225,539, 5,288,514, 5,324,483, 5,332,740, 5,332,837, 5,334,528, 5,403,484, 5,427,908, 5,475,092, 5,495,009, 5,530,101, 5,545,806, 5,547,667, 5,569,825, 5,571,698, 5,573,922, 5,580,717, 5,585,089, 5,585,499, 5,587,161, 5,595,499, 5,606,017, 5,622,929, 5,625,126, 5,629,430, 5,633,425, 5,641,780, 5,660,829, 5,661,016, 5,686,237, 5,693,762, 5,703,080, 5,712,374, 5,714,586, 5,739,116, 5,739,350, 5,770,429, 5,773,001, 5,773,435, 5,786,377 5,786,486, 5,789,650, 5,814,318, 5,846,545, 5,874,299, 5,877,296, 5,877,397, 5,885,793, 5,939,598, 5,962,216, 5,969,108, 5,985,908, 6,060,608, 6,066,742, 6,075,181, 6,103,236, 6,114,598, 6,130,237, 6,132,722, 6,143,901, 6,150,584, 6,162,963, 6,172,197, 6,180,370, 6,194,612, 6,214,345, 6,262,271, 6,281,354, 6,310,209, 6,329,497, 6,342,480, 6,486,326, 6,512,101, 6,521,404, 6,534,660, 6,544,731, 6,548,530, 6,555,313, 6,555,693, 6,566,336, 6,586,618, 6,593,081, 6,630,579, 6,756,397, 6,759,509, 6,762,179, 6,884,869, 6,897,034, 6,946,455, 7,049,316, 7,087,600, 7,091,186, 7,115,573, 7,129,261, 7,214,663, 7,223,837, 7,304,032, 7,329,507, 7,329,760, 7,388,026, 7,655,660, 7,655,661, 7,906,545, and 8,012,978.

Daunorubicin/Doxorubicin Analogues are also preferred for conjugation via the hydrophilic linkers of the present patent. The preferred structures and their synthesis are exampled in: Hurwitz, E., et al., Cancer Res. 35, 1175-1181 (1975). Yang, H. M., and Reisfeld, R. A., Proc. Natl. Acad. Sci. 85, 1189-1193 (1988); Pietersz, C. A., E., et al., E., et al.," Cancer Res. 48, 926-9311 (1988); Trouet, et al., 79, 626-629 (1982); Z. Brich et al., J. Controlled Release, 19, 245-258 (1992); Chen et al., Syn. Comm., 33, 2377-2390, 2003; King et al., Bioconj. Chem., 10, 279-288, 1999; King et al., J. Med. Chem., 45, 4336-4343, 2002; Kratz et al., J Med Chem. 45, 5523-33. 2002; Kratz et al., Biol Pharm Bull. January 21, 56-61, 1998; Lau et al., Bioorg. Med. Chem. 3, 1305-1312, 1995; Scott et al., Bioorg. Med.l Chem. Lett. 6, 1491-1496; 1996; Watanabe et al., Tokai J. Experimental Clin. Med. 15, 327-334, 1990; Zhou et al., J. Am. Chem. Soc. 126, 15656-7, 2004; WO 01/38318; U.S. Pat. Nos. 5,106,951; 5,122,368; 5,146,064; 5,177,016; 5,208,323; 5,824,805; 6,146,658; 6,214,345; 7,569,358; 7,803,903; 8,084,586; 8,053,205.

Auristatins and dolastatins are preferred in conjugation via the hydrophilic linkers of this patent. The auristatins (e.g. auristain E (AE) auristatin EB (AEB), auristatin EFP (AEFP), monomethyl auristatin E (MMAE), Monomethylauristatin (MMAF), Auristatin F phenylene diamine (AFP) and a phenylalanine variant of MMAE) which are synthetic analogs of dolastatins, are described in Int. J. Oncol. 15:367-72 (1999); Molecular Cancer Therapeutics, vol. 3, No. 8, pp. 921-932 (2004); U.S. application Ser. Nos. 11/134,826, 20060074008, 2006022925. U.S. Pat. Nos. 4,414,205, 4,753,894, 4,764,368, 4,816,444, 4,879,278, 4,943,628, 4,978,744, 5,122,368, 5,165,923, 5,169,774, 5,286,637, 5,410,024, 5,521,284, 5,530,097, 5,554,725, 5,585,089, 5,599,902, 5,629,197, 5,635,483, 5,654,399, 5,663,149, 5,665,860, 5,708,146, 5,714,586, 5,741,892, 5,767,236, 5,767,237, 5,780,588, 5,821,337, 5,840,699, 5,965,537, 6,004,934, 6,033,876, 6,034,065, 6,048,720, 6,054,297, 6,054,561, 6,124,431, 6,143,721, 6,162,930, 6,214,345, 6,239,104, 6,323,315, 6,342,219, 6,342,221, 6,407,213, 6,569,834, 6,620,911, 6,639,055, 6,884,869, 6,913,748, 7,090,843, 7,091,186, 7,097,840, 7,098,305, 7,098,308, 7,498,298, 7,375,078, 7,462,352, 7,553,816, 7,659,241, 7,662,387, 7,745,394, 7,754,681, 7,829,531, 7,837,980, 7,837,995, 7,902,338, 7,964,566, 7,964,567, 7,851,437, 7,994,135.

The benzodiazepine dimers (e. g. dimmers of pyrrolobenzodiazepine (PBD) or (tomaymycin), indolinobenzodiazepines, imidazobenzothiadiazepines, or oxazolidinobenzodiazepines) which are preferred cytotoxic agents according to the present invention are exampled in the art: U.S. Pat. Nos. 8,163,736; 8,153,627; 8,034,808; 7,834,005; 7,741,319; 7,704,924; 7,691,848; 7,678,787; 7,612,062; 7,608,615; 7,557,099; 7,528,128; 7,528,126; 7,511,032; 7,429,658; 7,407,951; 7,326,700; 7,312,210; 7,265,105; 7,202,239; 7,189,710; 7,173,026; 7,109,193; 7,067,511; 7,064,120; 7,056,913; 7,049,311; 7,022,699; 7,015,215; 6,979,684; 6,951,853; 6,884,799; 6,800,622; 6,747,144; 6,660,856; 6,608,192; 6,562,806; 6,977,254; 6,951,853; 6,909,006; 6,344,451; 5,880,122; 4,935,362; 4,764,616; 4,761,412; 4,723,007; 4,723,003; 4,683,230; 4,663,453; 4,508,647; 4,464,467; 4,427,587; 4,000,304; US patent appl. 20100203007, 20100316656, 20030195196.

The drugs/cytotoxic agents used for conjugation via a hydrophilic linker of the present patent can be any analogues and/or derivatives of drugs/molecules described in the present patent. One skilled in the art of drugs/cytotoxic agents will readily understand that each of the drugs/cytotoxic agents described herein can be modified in such a manner that the resulting compound still retains the specificity and/or activity of the starting compound. The skilled artisan will also understand that many of these compounds can be used in place of the drugs/cytotoxic agents described herein. Thus, the drugs/cytotoxic agents of the present invention include analogues and derivatives of the compounds described herein.

All references cited herein and in the examples that follow are expressly incorporated by reference in their entireties.

EXAMPLES

The invention is further described in the following examples, which are not intended to limit the scope of the invention. Cell lines described in the following examples were maintained in culture according to the conditions specified by the American Type Culture Collection (ATCC) or Deutsche Sammlung von Mikroorganismen und Zellkulturen GmbH, Braunschweig, Germany (DMSZ), or The Shanghai Cell Culture Institute of Chinese Acadmy of Science, unless otherwise specified. Cell culture reagents were obtained from Invitrogen Corp., unless otherwise specified. All anhydrous solvents were commercially obtained and stored in Sure-seal bottles under nitrogen. All other reagents and solvents were purchased as the highest grade available and used without further purification. The preparative HPLC separations were performed with Varain PreStar HPLC. NMR spectra were recorded on Varian Mercury 400 MHz Instrument. Chemical shifts (.delta.) are reported in parts per million (ppm) referenced to tetramethylsilane at 0.00 and coupling constants (J) are reported in Hz. The mass spectral data were acquired on a Waters Xevo Qtof mass spec with Waters Acquity UPLC separations module and Acquity TUV detector.

Example 1

3-((((2-(2,5-Dioxo-2,5-dihydro-1H-pyrrol-1-yl)ethyl)amino)(hydroxy)-phosphoryl)amino)propanoic acid (4)

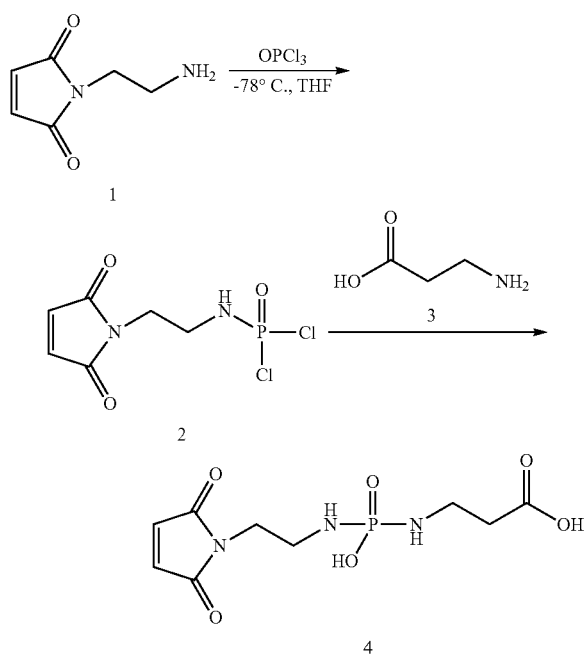

N-2-ethyl-malimide hydrochloride salt (1.0 g, 5.66 mmol) in THF (50 ml) cooled at −78° C. was added phosphoryl trichloride (0.86 g, 5.66 mmol). After stirred at −78° C. for 2 h to form (2-(2,5-dioxo-2,5-dihydro-1H-pyrrol-1-yl)ethyl) phosphoramidic dichloride (2), 3-aminopropanoic acid (0.51 g, 5.70 mmol) in the mixture of THF/H$_2$O (2:1, 30 ml) and triethylamine (1.0 g, 9.90 mmol) was added to the solution. The resulting mixture was stirred at RT for 3 h, concentrated under vacuum and purified on the SiO$_2$ column eluted with H$_2$O/CH$_3$CN (1:20~1:10) to afford the title compound 4 (1.28 g, 78% yield). ESI MS m/z—C$_9$H$_{13}$N$_3$O$_6$P (M−H), cacld. 290.06. found 290.10.

Example 2

N-Hydroxysuccinimidyl 3-((((2-(2,5-dioxo-2,5-dihydro-1H-pyrrol-1-yl)ethyl)amino)(hydroxy)phosphoryl)amino)propanoate (5)

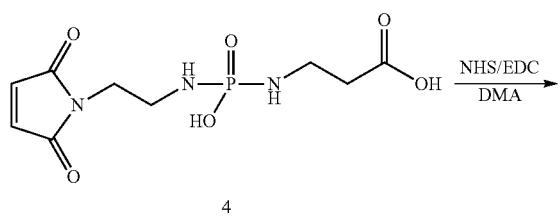

3-((((2-(2,5-Dioxo-2,5-dihydro-1H-pyrrol-1-yl)ethyl)amino)(hydroxy)-phosphoryl)amino)propanoic acid (4) (0.50 g, 1.72 mmol) in DMA (30 ml) was added NHS (0.20 g, 1.74 mmol) and EDC (0.81 g, 4.22 mmol). The mixture was stirred under Ar overnight, evaporated and purified on SiO$_2$ chromatography eluted with acetone/CH$_2$Cl$_2$ (1:10~1:3). The fractions containing the product were pooled, evaporated, solidified in C$_2$H$_5$OH/Dioxane/Hexane to afford the title compound (392 mg, 58% yield). ESI MS m/z—C$_{13}$H$_{16}$N$_4$O$_8$P (M−H), cacld. 387.08. found 387.20.

Example 3

3-((Bis((2-(2,5-dioxo-2,5-dihydro-1H-pyrrol-1-yl)ethyl)amino)-phosphoryl)-amino)propanoic acid (8)

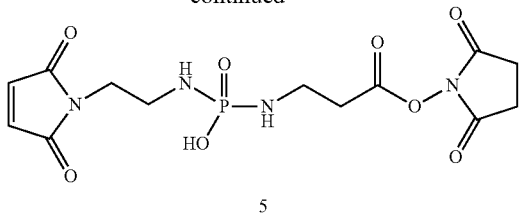

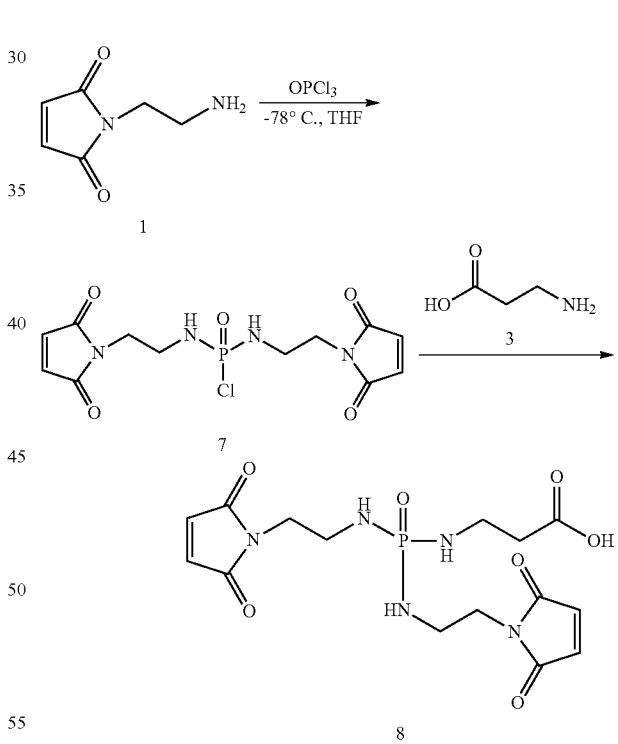

N-2-ethyl-malimide hydrochloride salt (2.0 g, 11.32 mmol) in THF (100 ml) cooled at −78° C. was added phosphoryl trichloride (0.86 g, 5.66 mmol). After stirred at −78° C. for 1 h, the mixture was added triethylamine (1.0 g, 9.90 mmol) and the resulting solution was stirred at RT for 3 h to generate bis(2-(2,5-dioxo-2,5-dihydro-1H-pyrrol-1-yl)ethyl)-phosphoramidic chloride (7). Then 3-aminopropanoic acid (0.51 g, 5.70 mmol) in the mixture of THF/H$_2$O (2:1, 30 ml) and triethylamine (1.51 g, 14.90 mmol) was added to the solution. The resulting mixture was stirred at 35° C. for 3 h, concentrated under vacuum and purified on the SiO₂ column eluted with H₂O/CH₃CN (1:20~1:10) to afford the title compound 8 (1.47 g, 63% yield). ESI MS m/z—C₁₅H₁₉N₅O₇P (M−H), cacld. 412.11. found 412.20.

Example 4

N-Hydroxysuccinimidyl 3-((Bis((2-(2,5-dioxo-2,5-dihydro-1H-pyrrol-1-yl)ethyl)amino)phosphoryl)-amino)propanoate (9)

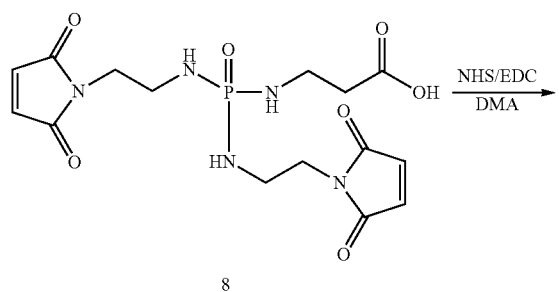

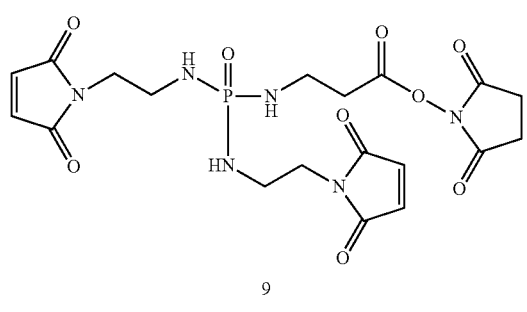

3-((Bis((2-(2,5-dioxo-2,5-dihydro-1H-pyrrol-1-yl)ethyl)amino)phosphoryl)amino)-propanoic acid (8) (0.55 g, 1.33 mmol) in DMA (30 ml) was added NHS (0.20 g, 1.74 mmol) and EDC (0.78 g, 4.06 mmol). The mixture was stirred under Ar overnight, evaporated and purified on short SiO₂ chromatography eluted with EtOAc/CH₂Cl₂ (1:3~1:1). The fractions containing the product were pooled, evaporated in vacuum to afford the title compound (536 mg, 79% yield). ESI MS m/z+C₁₉H₂₃N₆NaO₉P (M+Na), cacld. 533.13. found 533.20.

Example 5

3-((hydroxy((2-(pyridin-2-yldisulfanyl)ethyl)amino)phosphoryl)-amino)propanoic acid (15)

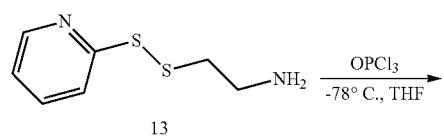

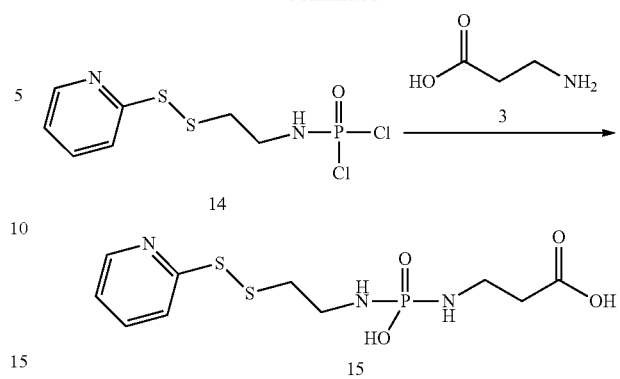

2-(pyridin-2-yldisulfanyl)ethanamine hydrochloride salt (1.40 g, 7.52 mmol) in THF (60 ml) cooled at −78° C. was added phosphoryl trichloride (1.15 g, 7.56 mmol). After stirred at −78° C. for 2 h to form (2-(pyridin-2-yldisulfanyl)ethyl)phosphoramidic dichloride (14), 3-aminopropanoic acid (0.67 g, 7.52 mmol) in the mixture of THF/H₂O (2:1, 30 ml) and triethylamine (20 g, 19.80 mmol) was added to the solution. The resulting mixture was stirred at RT for 3 h, concentrated under vacuum and purified on the SiO₂ column eluted with H₂O/CH₃CN (1:20~1:10) to afford the title compound 15 (1.69 g, 66% yield). ESI MS m/z—C₁₀H₁₅N₃O₄PS (M−H), cacld. 336.03. found 336.20.

Example 6

N-Hydroxysuccinimidyl 3-((((2-(pyridin-2-yldisulfanyl)ethyl)amino)-(hydroxy)phosphoryl)amino)propanoate (16)

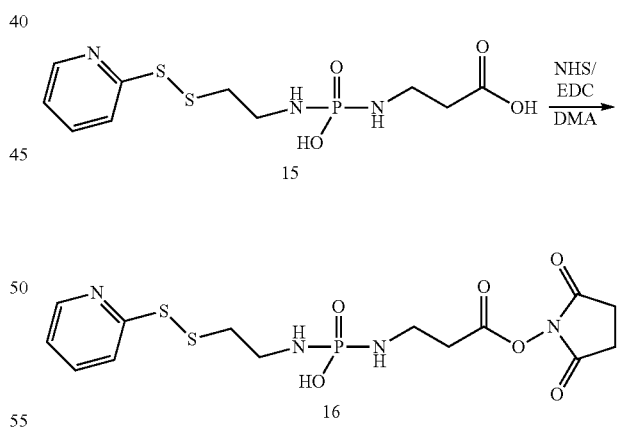

3-((((2-(pyridin-2-yldisulfanyl)ethyl)amino)(hydroxy)phosphoryl)amino)propanoic acid (15) (0.60 g, 1.78 mmol) in DMA (30 ml) was added NHS (0.22 g, 1.91 mmol) and EDC (0.81 g, 4.22 mmol). The mixture was stirred under Ar overnight, evaporated and purified on short C-18 chromatography eluted with water/dioxane at 4° C. The fractions containing the product were pooled, freezed at −78° C., lyophilized to afford the title compound 16 (477 mg, 61% yield). ESI MS m/z—C₁₄H₁₉N₄O₆PS₂ (M−H), cacld. 433.05. found 433.20.

Example 7

3-((Bis((2-(pyridin-2-yldisulfanyl)ethyl)amino)phosphoryl)amino)-propanoic acid (18)

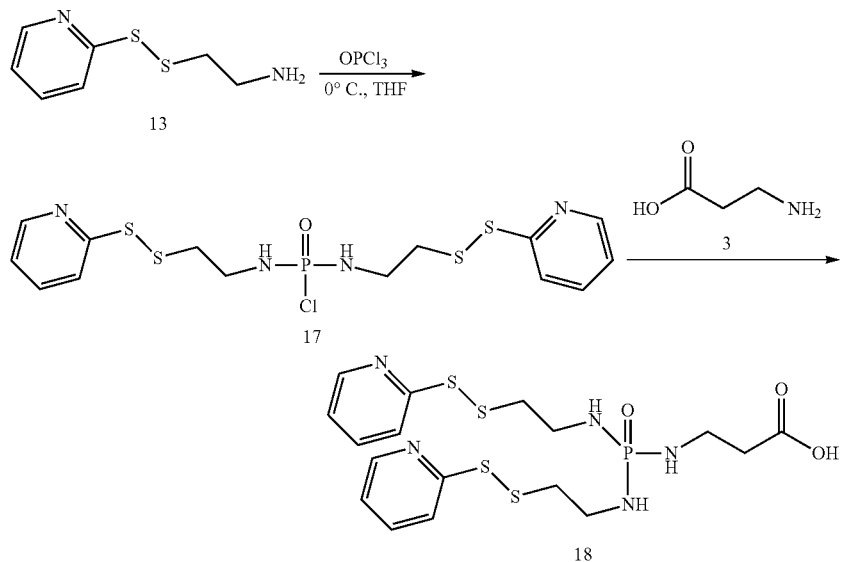

2-(pyridin-2-yldisulfanyl)ethanamine hydrochloride salt (2.10 g, 11.29 mmol) in THF (100 ml) cooled at −78° C. was added phosphoryl trichloride (0.85 g, 5.59 mmol). After stirred at −78° C. for 1 h, the mixture was added triethylamine (1.0 g, 9.90 mmol) and the resulting solution was stirred at RT for 3 h to generate bis(2-(pyridin-2-yldisulfanyl)ethyl)-phosphoramidic chloride (17). Then 3-aminopropanoic acid (0.61 g, 6.85 mmol) in the mixture of THF/H$_2$O (2:1, 30 ml) and triethylamine (1.80 g, 17.82 mmol) was added to the solution. The resulting mixture was stirred at 35° C. for 3 h, concentrated under vacuum and purified on the SiO$_2$ column eluted with H$_2$O/CH$_3$CN (1:20~1:10) to afford the title compound 18 (1.47 g, 63% yield). ESI MS m/z—C$_{17}$H$_{23}$N$_5$O$_3$PS (M−H), cacld. 504.05. found 504.20.

Example 8

2,5-dioxopyrrolidin-1-yl 3-((bis((2-(pyridin-2-yldisulfanyl)ethyl)-amino)phosphoryl)amino)propanoate (19)

3-((Bis((2-(pyridin-2-yldisulfanyl)ethyl)amino)phosphoryl)amino)propanoic acid (18) (0.52 g, 1.03 mmol) in DMA (30 ml) was added NHS (0.20 g, 1.74 mmol) and EDC (0.80 g, 4.16 mmol). The mixture was stirred under Ar overnight, evaporated and purified on short SiO$_2$ chromatography eluted with EtOAc/CH$_2$Cl$_2$ (1:4~1:1). The fractions containing the product were pooled, evaporated in vacuum to afford the title compound 19 (536 mg, 79% yield). ESI MS m/z+C$_{21}$H$_{27}$N$_6$NaO$_5$PS$_4$ (M+Na), cacld. 625.06. found 625.20.

Example 9

1-(2-(Methylamino)ethyl)-1H-pyrrole-2,5-dione (43)

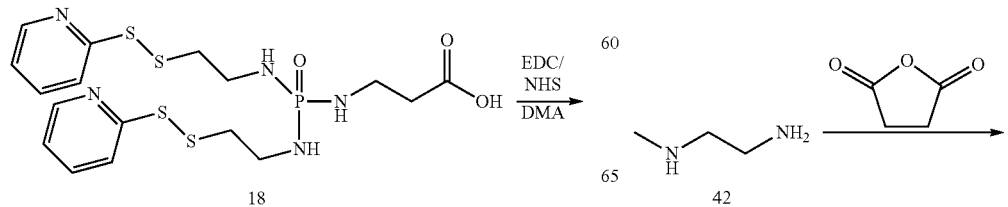

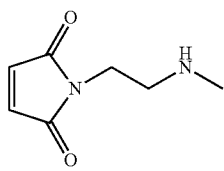

N¹-methylethane-1,2-diamine (10.23 g, 138.08 mmol) in DMA (150 ml) was added succinic anhydride (13.82 g, 138.08 mmol) at 0° C. After stirring under Ar at 0° C. for 1 hr then RT for 4 h, the mixture was evaporated, redissolved in acetic acid (100 ml, 98%) and Ac₂O (0.5 mL), then heated at 80° C. for 8 h. The mixture was concentrated, purified on C-18 flush chromatography eluted with water/CH₃OH (100% water to 60% water containing 0.3% HCl) to afford the title compound as a hydrochloric acid salt. (13.68 g, 52% yield). ESI MS m/z+155.10 (M+H).

Example 10

3-((bis((2-(2,5-dioxo-2,5-dihydro-1H-pyrrol-1-yl)ethyl)(methyl)-amino)phosphoryl)(methyl)amino)propanoic acid (50)

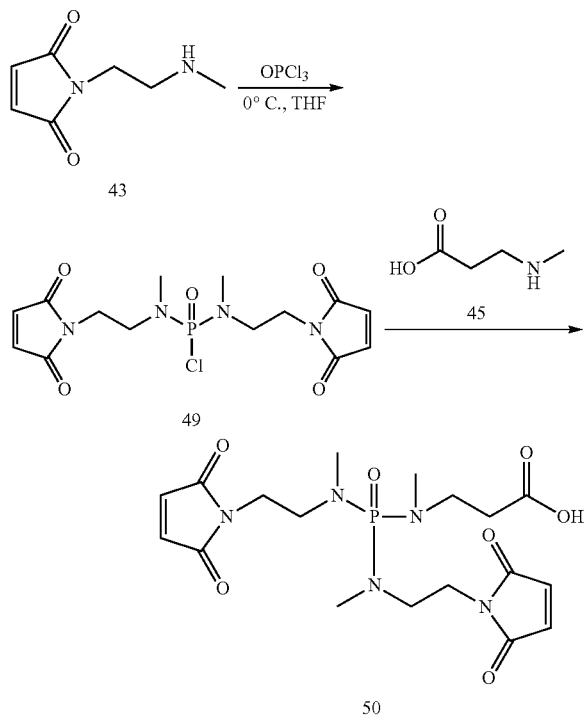

1-(2-(Methylamino)ethyl)-1H-pyrrole-2,5-dione, HCl salt (43) (4.05 g, 21.00 mmol) in THF (100 ml) cooled at −78° C. was added phosphoryl trichloride (1.59 g, 10.50 mmol). After stirred at −78° C. for 1 h, the mixture was added triethylamine (1.2 g, 11.88 mmol) and the resulting solution was stirred at RT for 3 h to generate bis(2-(2,5-dioxo-2,5-dihydro-1H-pyrrol-1-yl)ethyl(methyl))-phosphoramidic chloride (49). Then 3-(methylamino)propanoic acid (1.21 g, 11.73 mmol) in the mixture of THF (30 ml) and triethylamine (1.20 g, 11.88 mmol) was added to the solution. The resulting mixture was stirred at 45° C. for 3 h, concentrated under vacuum and purified on the SiO₂ column eluted with H₂O/CH₃CN (1:20~1:10) to afford the title compound 50 (2.44 g, 51% yield). ESI MS m/z—C₁₈H₂₅N₅O₇P (M−H), cacld. 454.16. found 454.20.

Example 11

2,5-dioxopyrrolidin-1-yl 3-((bis((2-(2,5-dioxo-2,5-dihydro-1H-pyrrol-1-yl)ethyl)(methyl)amino)phosphoryl)(methyl)amino)propanoate (51)

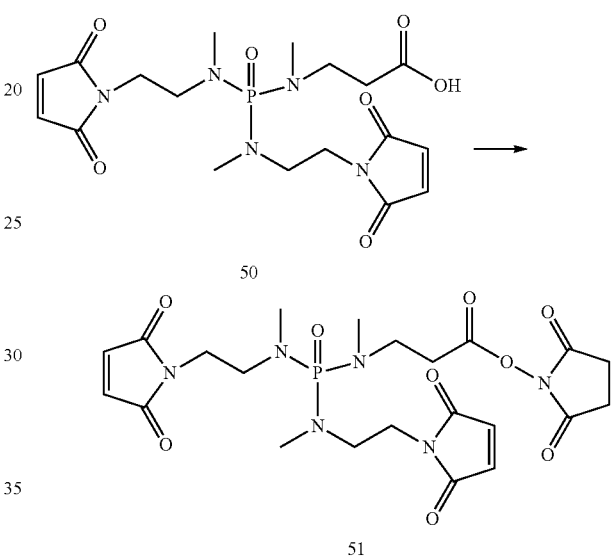

Compound 50 (1.10 g, 2.41 mmol) in DMA (40 ml) was added NHS (0.40 g, 3.48 mmol) and EDC (1.80 g, 9.37 mmol). The mixture was stirred under Ar overnight, evaporated and purified on short SiO₂ chromatography eluted with acetone/CH₂Cl₂ (1:6~1:2). The fractions containing the product were pooled, evaporated in vacuum to afford the title compound 51 (971 mg, 73% yield). ESI MS m/z+ C₂₂H₂₉N₆NaO₉P (M+Na), cacld. 575.17. found 575.20.

Example 12

Conjugation of Two DM1 Per Linker with an Antibody for (52a)

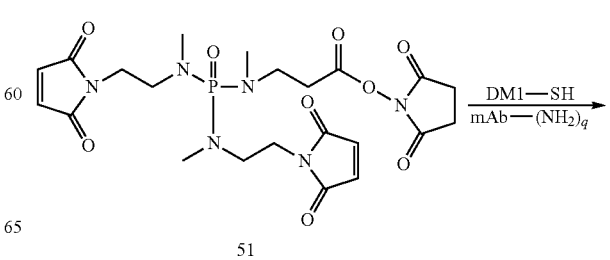

-continued

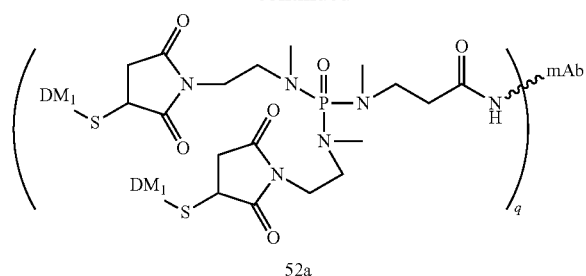

52a

The compound 51 (35 μL, 20 mM in DMA), buffers (60 μL, 100 mM NaH$_2$PO$_4$, pH 5.0-7.0) and DM1 (85 μL, 20 mM in DMA) were incubated at 15~30° C. for 20 min ~2.5 h. Then the mixture was added to a mixture of 2.0 mL of 10 mg/ml antiHer2 antibody in pH 6.5~8.0 PBS buffer, 1.0~2.0 mL of 100 mM NaH$_2$PO$_4$, pH 7.5 buffer. The subject mixture solution was incubated at RT for 2~24 h, purified on G-25 column eluted with 100 mM NaH$_2$PO$_4$, 50 mM NaCl pH 5.5~7.5 buffers to afford 16.5~18.3 mg of the compound 52a (~86% yield) in 11.6~14.2 ml buffers. The DM1/antibody ratio was 6.8~7.8, which was calculated according to the reference (Zhao, R. Y. et al, J. Med. Chem. 2011, 54, 3606). It was 95~99% monomer analyzed by SEC HPLC (Tosoh Bioscience, Tskgel G3000SW, 7.8 mm ID×30 cm, 0.5 ml/min, 100 min)

Alternatively, the compound 51 (35 μL, 20 mM in DMA), was added to a mixture of 2.0 mL of 10 mg/ml antiHer2 antibody in pH 6.5~8.0 PBS buffers, 0.5~1.7 mL of 100 mM NaH$_2$PO$_4$, pH 6.5~8.0 buffer. After incubated at RT for 2 h, the mixture was purified on G-25 column eluted with 100 mM NaH$_2$PO$_4$, 50 mM NaCl pH 5.5~7.5 buffers. Then to the collected subject solution (4.5~6.5 ml) were added DM1 (70 μL, 20 mM in DMA) and DMA (0.1~0.5 ml). The mixture was then incubated at RT for 2-16 h, purified on G-25 column eluted with 100 mM NaH$_2$PO$_4$, 50 mM NaCl pH 5.5~7.5 buffers to afford 15.8~17.3 mg of the compound 52a (~81% yield) in 15.5~17.4 ml buffers. The DM1/antibody ratio was 7.1~7.7, which was calculated according to the reference (Zhao, R. Y. et al, J. Med. Chem. 2011, 54, 3606). It was 95-99% monomer analyzed by SEC HPLC (Tosoh Bioscience, Tskgel G3000SW, 7.8 mm ID×30 cm, 0.5 ml/min, 100 min).

Example 13

Compound 147a Bearing a Hydrophilic Linker of the Present Patent Conjugated with a Tubulysin Analog

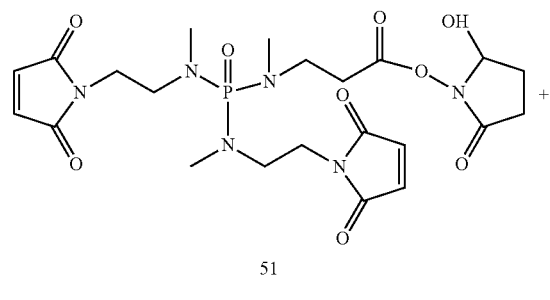

51

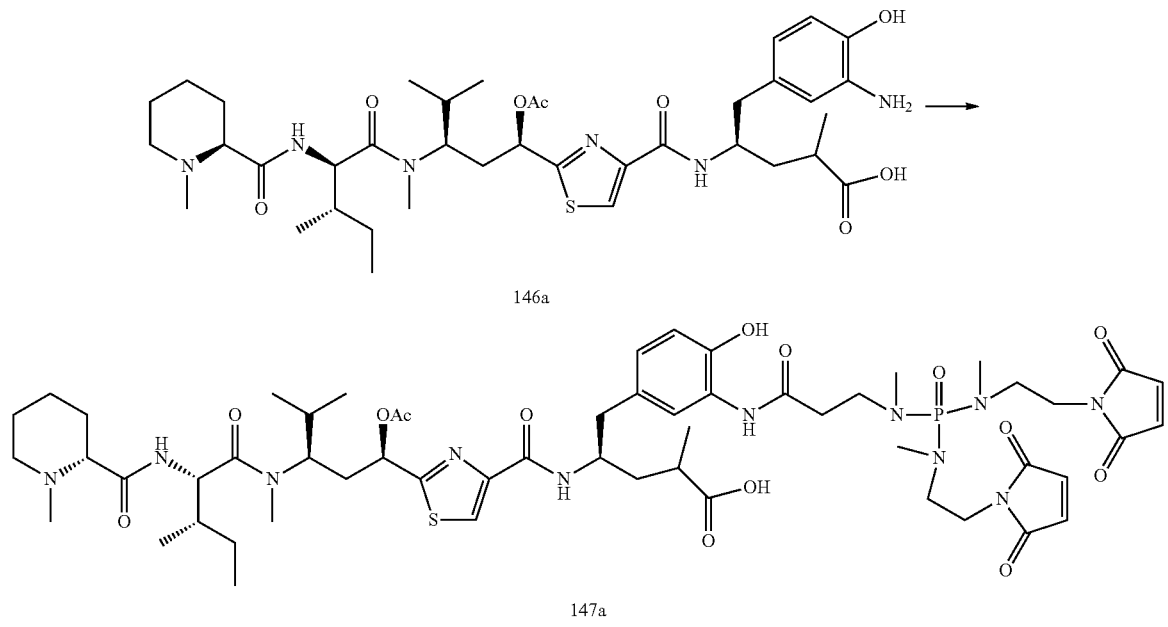

146a

147a

The compound 51 (120 mg, 0.217 mmol) in THF (3.0 ml) was added compound 146a (Huang Y. et al, Med Chem. #44, 249$^{th}$ ACS National Meeting, Dever, Colo., Mar. 22~26, 2015; WO2014009774) (151 mg, 0.199 mmol) in THF (3.0 ml) and buffer (5 ml, 100 mM Na2HPO4, pH 7.2). After stirred at RT for 4 h, the mixture was concentrated and purified with C-18 preparative HPLC (250 mm×ID 30 mm), eluted with water/ethanol (90% water to 50% water in 35 min, v=65 ml/min). The fractions containing the product were pooled, concentrated and crystallized with EtOH/Hexane to afford the title compound (159 mg, 67% yield). ESI MS m/z+$C_{56}H_{82}N_{11}NaO_4PS$ (M+Na), cacld. 1218.35. found 1218.40.

Example 14

Conjugated Compound 147a to an Antibody 148a

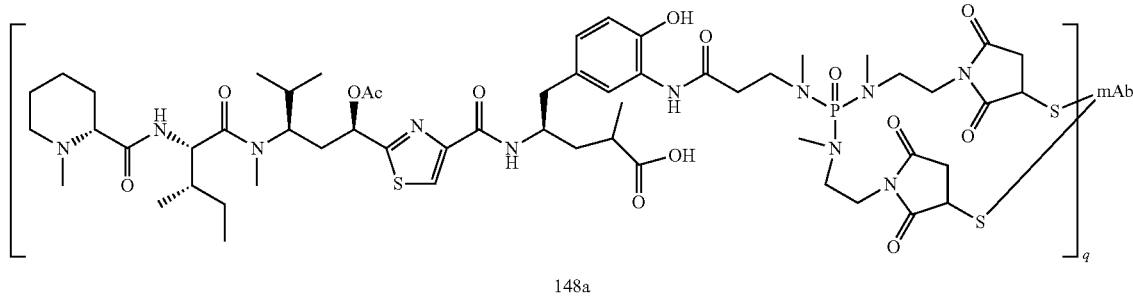

To a mixture of 2.0 mL of 10 mg/ml antiHer2 antibody in pH 6.0~8.0, were added of 0.70~2.0 mL PBS buffer of 100 mM $NaH_2PO_4$, pH 6.5~7.5 buffers, TCEP (28 µL, 20 mM in water) and the compound 147a (35 µL, 20 mM in DMA). The mixture was incubated at RT for 2~16 h, then DHAA (135 µL, 50 mM) was added in. After continuous incubation at RT overnight, the mixture was purified on G-25 column eluted with 100 mM $NaH_2PO_4$, 50 mM NaCl pH 6.0~7.5 buffer to afford 16.8~17.9 mg of the conjugate compound 148a (~87% yield) in 13.1~14.9 ml buffer. The drug/antibody ratio (DAR) was 2.8~3.7, which was determined UPLC-Qtof mass spectrum. It was 96~99% monomer analyzed by SEC HPLC (Tosoh Bioscience, Tskgel G3000SW, 7.8 mm ID×30 cm, 0.5 ml/min, 100 min) and a single band measured by SDS-PAGE gel.

Alternatively, a mixture of 2.0 mL of 10 mg/ml antiHer2 antibody in pH 6.0~8.0 PBS buffer, 0.50~1.5 mL of 100 mM $NaH_2PO_4$, pH 6.0~8.0 buffers, and DTT (30 µL, 20 mM in water) was incubated at 15~37° C. for 1~5 h and then purified on G-25 column eluted with 100 mM $NaH_2PO_4$, 50 mM NaCl pH 6.0~8.0 buffer. The pooled fractions (3.8~5.8 ml) was added 0.2~0.6 mL DMA and compound 147a (35 µL, 20 mM in DMA), and incubated at RT for 4~12 h. After addition of DHAA (135 µL, 50 mM) and continuous incubation at RT overnight, the mixture was purified on G-25 column eluted with 100 mM $NaH_2PO_4$, 50 mM NaCl pH 7.5 buffer to afford 15.5~16.8 mg of the conjugate compound 148a (~80% yield) in 13.8~15.9 ml buffers. The drug/antibody ratio (DAR) was 2.6~3.8, which was determined UPLC-QTOF mass spectrum. It was 96~98% monomer analyzed by SEC HPLC (Tosoh Bioscience, Tskgel G3000SW, 7.8 mm ID×30 cm, 0.5 ml/min, 100 min) and a single band measured by SDS-PAGE gel.

Example 15

In Vitro Cytotoxicity Evaluation of Conjugates 52a and 148a

The targeted cells (e.g. N-87, SKOV3 and HL60 cells, 6,000 cells) were cultured in the presence of various concentrations the antiHer2 antibody conjugate 52a and 148a for 96 hours after which cell viability was measured by propidium iodide exclusion and analyzed by flow cytometry using a Becton Dickinson FACSort (Becton Dickinson, Franklin Lakes, N.J.). Red fluorescent intensity (emission at 617 nm in the FL2 channel) of the cells excited at 488 nm was measured. The regions for viable cells were also set using both the forward light scatter and right-angle light scatter properties of the cells. The loss of viability was determined by the loss of cells from within the gated region defining viable cells. The average number of viable cells per 6 replicate cultures was calculated. The survival fraction was plotted versus conjugate concentration to determine the $IC_{50}$ value (50% cell killing concentration) of the conjugates 52a and 148a.

The cytotoxicity results:

| $IC_{50}$ nM | N87 cell (Ag+) | SK-OV-3 cell (Ag+) | HL60 cell (Ag−) |
|---|---|---|---|
| Conjugate 52a | 0.027 nM | 0.021 nM | >50 nM |
| Conjugate 148a | 0.038 nM | 0.032 nM | >50 nM |

Specificity of conjugate 52a for N87 cell was over 1850 ($IC_{50}$>50/$IC_{50}$=0.027), and for SK-OV-3 cell was over 2380.

Specificity of conjugate 148a for N87 cell was over 1315 ($IC_{50}$>50/$IC_{50}$=0.038), and for SK-OV-3 cell was over 1560.

Both conjugate 52a and conjugate 148a were extremely potent and much specifically targeting the antigen positive tumor cells.

What is claimed is:

1. A hydrophilic linker compound of Formula (I)

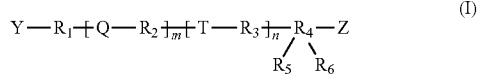

wherein:
Y represents a functional group that is capable of reacting with a cell-binding agent;
Q and T are either —$X_1$—P(=O)(OM)-, or —$X_1$—S($O_2$)—, or —$X_1$—S(O)—, or —$X_1$—P(=O)(OM)-$X_2$—, or —$X_1$—P(=O)[$X_2$—$R_4$—Z]—$X_3$—, or —$X_1$—P(=O)[$X_2$—$R_1$—Y]—$X_3$—, or —$X_1$—S($O_2$)—$X_2$—, or —$X_1$—S(O)—$X_2$—, wherein $X_1$, $X_2$ and $X_3$ are independently N($R_7$), O, $CH_2$ or S provided that at least one $X_1$ is either N($R_7$) or S;
m and n are integer from 0 to 5, but not 0 at the same time;
Z represents a functional group that enables linkage of the hydrophilic linker compound to a cytotoxic drug via an alkyl, alkenyl, alkynyl, aromatic, heteroalkyl, disulfide, thioether, thioester, hydrazone, ether, ester, carbamate, carbonate, secondary, tertiary, or quartary amine, imine, cycloheteroalkyane, heteroaromatic, alkoxime or amide bond;
$R_5$, $R_6$, and $R_7$ are the same or different and are H, a linear alkyl having from 1 to 6 carbon atoms, branched or cyclic alkyl having from 3 to 6 carbon atoms, linear, branched or cyclic alkenyl or alkynyl, or ester, ether, or amide having 2 to 6 carbon atoms, or polyethyleneoxy unit of formula (OCH$_2$CH$_2$)$_p$, wherein p is an integer from 0 to about 1000, or combination thereof;
each of $R_1$, $R_2$, $R_3$ and $R_4$ is a linear alkyl having from 1 to 6 carbon atoms, branched or cyclic alkyl having from 3 to 6 carbon atoms, linear, branched or cyclic alkenyl or alkynyl, or ester, ether, or amide having 2 to 6 carbon atoms, or polyethyleneoxy unit of formula (OCH$_2$CH$_2$)$_p$, wherein p is an integer from 0 to about 1000, or combination thereof, or a chain of atoms selected from the group consisting of C, N, O, S, Si, and P that covalently connects to a cell-surface binding ligand, a phosphinate or sulfonyl group, a conjugated drug or each other; and
M is H, or Na, or K, or $N^+R_1R_2R_3$ or a pharmaceutical salt.

2. A cell-binding agent-drug conjugate compound of Formula (II)

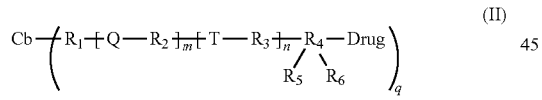

wherein:
Cb represents a cell-binding agent;
Drug represents a drug;
Q and T are either —$X_1$—P(=O)(OM)-, or —$X_1$—S($O_2$)—, or —$X_1$—S(O)—, or —$X_1$—P(=O)(OM)-$X_2$—, or —$X_1$—P(=O)[$X_2$—$R_4$-Drug]-$X_3$—, or —$X_1$—P(=O)[$X_2$—$R_1$—Cb]—$X_3$—, or —$X_1$—S($O_2$)—$X_2$—, or —$X_1$—S(O)—$X_2$—;
$X_1$, $X_2$ and $X_3$ are independently N($R_7$), O, $CH_2$ or S provided that at least one $X_1$ is either N($R_7$) or S;
m and n are integer from 0 to 5, but not 0 at the same time;
q is 1 to 30;
$R_5$, $R_6$, and $R_7$ are the same or different and are H, a linear alkyl having from 1 to 6 carbon atoms, branched or cyclic alkyl having from 3 to 6 carbon atoms, linear, branched or cyclic alkenyl or alkynyl, or ester, ether, or amide having 2 to 6 carbon atoms, or polyethyleneoxy unit of formula (OCH$_2$CH$_2$)$_p$, wherein p is an integer from 0 to about 1000, or combination thereof;
each of $R_1$, $R_2$, $R_3$ and $R_4$ is a linear alkyl having from 1 to 6 carbon atoms, branched or cyclic alkyl having from 3 to 6 carbon atoms, linear, branched or cyclic alkenyl or alkynyl, or ester, ether, or amide having 2 to 6 carbon atoms, or polyethyleneoxy unit of formula (OCH$_2$CH$_2$)$_p$, wherein p is an integer from 0 to about 1000, or combination thereof, or a chain of atoms selected from the group consisting of C, N, O, S, Si, and P that covalently connects to a cell-surface binding ligand, a phosphinate or sulfonyl group, a conjugated drug or each other; and
M is H, or Na, or K, or $N^+R_1R_2R_3$ or a pharmaceutical salt,
wherein the cell binding agent is an antibody, a single chain antibody, an antibody fragment that binds to the target cell, a monoclonal antibody, a single chain monoclonal antibody, or a monoclonal antibody fragment that binds the target cell, a chimeric antibody, a chimeric antibody fragment that binds to the target cell, a domain antibody, a domain antibody fragment that binds to the target cell, a resurfaced antibody, a resurfaced single chain antibody, or a resurfaced antibody fragment that binds to the target cell, a humanized antibody or a resurfaced antibody, a humanized single chain antibody, or a humanized antibody fragment that binds to the target cell.

3. A compound of Formula (III):

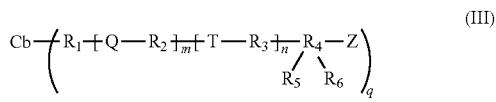

wherein:
Cb represents a cell-binding agent;
m and n are integer from 0 to 5, but not 0 at the same time;
q is 1 to 30;
Z represents a functional group that is capable of reacting with a cytotoxic drug via an alkyl, alkenyl, alkynyl, aromatic, heteroalkyl, disulfide, thioether, thioester, hydrazone, ether, ester, carbamate, carbonate, secondary, tertiary, or quartary amine, imine, cycloheteroalkyane, heteroaromatic, alkoxime or amide bond;
each of $R_1$, $R_2$, $R_3$ and $R_4$ is a linear alkyl having from 1 to 6 carbon atoms, branched or cyclic alkyl having from 3 to 6 carbon atoms, linear, branched or cyclic alkenyl or alkynyl, or ester, ether, or amide having 2 to 6 carbon atoms, or polyethyleneoxy unit of formula (OCH$_2$CH$_2$)$_p$, wherein p is an integer from 0 to about 1000, or combination thereof, or a chain of atoms selected from the group consisting of C, N, O, S, Si, and P that covalently connects to a cell-surface binding ligand, a phosphinate or sulfonyl group, a conjugated drug or each other;
$R_5$, and $R_6$ are the same or different and are H, a linear alkyl having from 1 to 6 carbon atoms, branched or cyclic alkyl having from 3 to 6 carbon atoms, linear, branched or cyclic alkenyl or alkynyl, or ester, ether, or amide having 2 to 6 carbon atoms, or polyethyleneoxy unit of formula (OCH$_2$CH$_2$)$_p$, wherein p is an integer from 0 to about 1000, or combination thereof;
Q and T are either —$X_1$—P(=O)(OM)-, or —$X_1$—S($O_2$)—, or —$X_1$—S(O)—, or —$X_1$—P(=O)(OM)-$X_2$—, or —$X_1$—P(=O)[$X_2$—$R_4$—Z]—$X_3$—, or —X$_1$—P(=O)[X$_2$—R$_1$—Cb]—X$_3$—, or —X$_1$—S(O$_2$)—X$_2$—, or —X$_1$—S(O)—X$_2$—;

X$_1$, X$_2$ and X$_3$ are independently N(R$_7$), O, CH$_2$ or S provided that at least one X$_1$ is either N(R$_7$) or S, wherein the cell binding agent is an antibody, a single chain antibody, an antibody fragment that binds to the target cell, a monoclonal antibody, a single chain monoclonal antibody, or a monoclonal antibody fragment that binds the target cell, a chimeric antibody, a chimeric antibody fragment that binds to the target cell, a domain antibody, a domain antibody fragment that binds to the target cell, a resurfaced antibody, a resurfaced single chain antibody, or a resurfaced antibody fragment that binds to the target cell, a humanized antibody or a resurfaced antibody, a humanized single chain antibody, or a humanized antibody fragment that binds to the target cell.

4. A compound of Formula (IV):

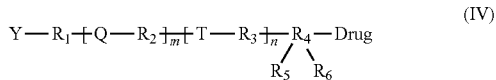

(IV)

wherein:

Y represents a functional group that is capable of reacting with a cell-binding agent;

Drug represents a drug;

m and n are integer from 0 to 5, but not 0 at the same time;

q is 1 to 30;

each of R$_1$, R$_2$, R$_3$ and R$_4$ is a linear alkyl having from 1 to 6 carbon atoms, branched or cyclic alkyl having from 3 to 6 carbon atoms, linear, branched or cyclic alkenyl or alkynyl, or ester, ether, or amide having 2 to 6 carbon atoms, or polyethyleneoxy unit of formula (OCH$_2$CH$_2$)$_p$, wherein p is an integer from 0 to about 1000, or combination thereof, or a chain of atoms selected from the group consisting of C, N, O, S, Si, and P that covalently connects to a cell-surface binding ligand, a phosphinate or sulfonyl group, a conjugated drug or each other;

R$_5$, and R$_6$ are the same or different and are H, a linear alkyl having from 1 to 6 carbon atoms, branched or cyclic alkyl having from 3 to 6 carbon atoms, linear, branched or cyclic alkenyl or alkynyl, or ester, ether, or amide having 2 to 6 carbon atoms, or polyethyleneoxy unit of formula (OCH$_2$CH$_2$)$_p$, wherein p is an integer from 0 to about 1000, or combination thereof;

Q and T are either —X$_1$—P(=O)(OM)-, or —X$_1$—S(O$_2$)—, or —X$_1$—S(O)—, or —X$_1$—P(=O)(OM)-X$_2$—, or —X$_1$—P(=O)[X$_2$—R$_4$-Drug]-X$_3$—, or —X$_1$—P(=O)[X$_2$—R$_1$—Y]—X$_3$—, or —X$_1$—S(O$_2$)—X$_2$—, or —X$_1$—S(O)—X$_2$—;

X$_1$, X$_2$ and X$_3$ are independently N(R$_7$), O, CH$_2$ or S provided that at least one X$_1$ is either N(R$_7$) or S.

5. The hydrophilic linker compound of Formula (I) of claim 1, wherein Q or T is —X$_1$—P(=O)[X$_1$—R$_1$—Y]—X$_3$—.

6. The hydrophilic linker compound of Formula (I) of claim 1, wherein Q or T is —X$_1$—P(=O)[X$_2$—R$_4$—Z]—X$_3$—.

7. The cell-binding agent-drug conjugate compound of Formula (II) of claim 2, wherein Q or T is —X$_1$—P(=O)[X$_1$—R$_1$—Cb]—X$_3$—.

8. The cell-binding agent-drug conjugate compound of Formula (II) of claim 2, wherein Q, or T is —X$_1$—P(=O)[X$_2$—R$_4$-Drug]-X$_3$—.

9. The compound of Formula (III) of claim 3, wherein Q, or T is —X$_1$—P(=O)[X$_2$—R$_1$—Cb]—X$_3$—.

10. The compound of Formula (III) of claim 3, wherein Q, or T is —X$_1$—P(=O)[X$_2$—R$_4$—Z]—X$_3$—.

11. The compound of Formula (IV) of claim 4, wherein Q, or T is —X$_1$—P(=O)[X$_2$—R$_1$—Y]—X$_3$—.

12. The compound of Formula (IV) of claim 4, wherein Q, or T is —X$_1$—P(=O)[X$_2$—R$_4$-Drug]-X$_3$—.

13. The compound of any one of claims 2, 4, 8 and 12, wherein "Drug" is a chromophore molecule.

14. The conjugate compound of any one of claims 2, 4, 8 and 12, wherein "Drug" is selected from the group consisting of tubulysins, calicheamicins, auristatins, maytansinoids, CC-1065 analogs, morpholino doxorubicins, taxanes, cryptophycins, epothilones, dimers of pyrrolobenzodiazepine (PBD) and tomaymycin, indolinobenzodiazepines, imidazobenzothiadiazepines, and oxazolidinobenzodiazepines, pharmaceutically acceptable salts of any of the above molecules, pharmaceutically acceptable acids of any of the above molecules, siRNA and a combination thereof.

15. The compound according to any one of claims 2, 3, 7, and 9, wherein the cell binding agent is capable of targeting against a tumor cell, an autoimmune disease cell, a myeloid cell, a T-cell, a B cell, or a melanocyte.

16. The compound according to any one of claims 2, 3, 7, and 9, wherein the cell binding agent is capable of targeting against any one of the following antigens or receptors: CD3, CD4, CD5, CD6, CD7, CD8, CD9, CD10, CD11a, CD11b, CD11c, CD12w, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49b, CD49c, CD51, CD52, CD53, CD54, CD55, CD56, CD58, CD59, CD61, CD62E, CD62L, CD62P, CD63, CD66, CD68, CD69, CD70, CD72, CD74, CD79, CD79a, CD79b, CD80, CD81, CD82, CD83, CD86, CD87, CD88, CD89, CD90, CD91, CD95, CD96, CD98, CD100, CD103, CD105, CD106, CD109, CD117, CD120, CD125, CD126, CD127, CD133, CD134, CD135, CD138, CD141, CD142, CD143, CD144, CD147, CD151, CD147, CD152, CD154, CD156, CD158, CD163, CD166, CD168, CD174, CD180, CD184, CDw186, CD194, CD195, CD200, CD200a, CD200b, CD209, CD221, CD227, CD235a, CD240, CD262, CD271, CD274, CD276 (B7-H3), CD303, CD304, CD309, CD326, 4-1BB, SAC, 5T4 (Trophoblast glycoprotein, TPBG), Wnt-Activated Inhibitory Factor 1, Adenocarcinoma antigen, AGS-5, AGS-22M6, Activin receptor-like kinase 1, AKAP-4, Alpha intergrin, Amino-peptidase N, Amyloid beta, Angiopoietin 2, Angiopoietin 3, Annexin A1, AOC3 (VAP-1), B7-H3, BAFF (B-cell activating factor), Bombesin, C5, C242 antigen, CA125 (carbohydrate antigen 125, MUC16), CA-IX (or CAIX, carbonic anhydrase 9), CALLA, CanAg, Canis lupus familiaris IL31, Cardiac myosin, CCL11 (C-C motif chemokine 11), CCR4 (C-C chemokine receptor type 4, CD194), CCR5, CEA (Carcinoembryonic antigen), CFD (Factor D), Cholecystokinin 2, CLDN18 (Claudin-18), Clumping factor A, CRIPTO, FCSF1R (Colony stimulating factor 1 receptor, CD115), C—X—C chemokine receptor type 4, cyclic ADP ribose hydrolase, Cytomegalovirus glycoprotein B, DLL4 (delta-like-ligand 4), DPP4 (Dipeptidyl-peptidase 4), DR5 (Death receptor 5), ED-B, EGFL7 (EGF-like domain-containing protein 7), Endothelin B receptor, Endotoxin, EpCAM (epithelial cell adhesion molecule), EphA2, ERBB2 (Epidermal Growth Factor Receptor 2), FAP (Fibroblast activation protein alpha), FCGR1, alpha-Fetoprotein, Fibrin II beta chain, FOLR (folate receptor), Folate hydrolase, Fos-related antigen 1.F protein of respiratory syncytial virus, Frizzled receptor, Fucosyl GM1, GD2 ganglioside, G-28 (a cell surface antigen glycolipid), GD3, GloboH, Glypican 3, N-glycolylneuraminic acid, GM3, GMCSF receptor a-chain, Growth differentiation factor 8, GPNMB (Transmembrane glycoprotein NMB), GUCY2C (Guanylate cyclase 2C, guanylyl cyclase C, intestinal Guanylate cyclase, Guanylate cyclase-C receptor,), Heat shock proteins, Hemagglutinin, Hepatitis B surface antigen, HER1 (human epidermal growth factor receptor 1), HER3 (ERBB-3), HGF/SF (Hepatocyte growth factor/scatter factor), HHGFR, human leukocyte antigen, HMWMAA, Human chorionic gonadotropin, HNGF, ICAM-1 (Intercellular Adhesion Molecule 1), IGF1R, Influenza hemagglutinin, IL-2 receptor (interleukin 2 receptor), IL-6R (interleukin 6 receptor), Integrins, Interferon gamma-induced protein, KIR2D, Le, Legumain, LHRH, LINGO-1, Lipoteichoic acid, LIV1A, LTA, MAD-CT-2, MAGE-2, MAGE 4, MART1, MCP-1, MIF, MS4A1, MSLN (mesothelin), MUC1 (Mucin 1), MCP1 (monocyte chemotactic protein 1), 1VIPG, MS4A1 (membrane-spanning 4-domains subfamily A), Myelin-associated glycoprotein, Myostatin, NARP-1, NCA-90, Nectin-4, NGF, Neural apoptosis-regulated proteinase 1, NOGO-A, Notch receptor, Nucleolin, NY-BR-1, OX-40, OxLDL (Oxidized low-density lipoprotein), P21, P97, prostatic acid phosphatase, PCSK9, PDCD1 (PD-1, Programmed cell death protein 1, CD279), PDGF-Ra (Alpha-type platelet-derived growth factor receptor), PDGFR-β, PDL-1, PLAC1, PLAP-like testicular alkaline phosphatase, Phosphate-sodium co-transporter, PMEL 17, Polysialic acid, PS (Phosphatidylserine), Rabies virus glycoprotein, Rhesus factor, RANKL, ROBO4, RON, Sclerostin, SLAMF7 (SLAM family member 7), Selectin P, SDC1 (Syndecan 1), SIP (Sphingosine-1-phosphate), Sperm protein 17, STEAP1 (six-transmembrane epithelial antigen of the prostate 1), STEAP2, TAG-72 (tumor associated glycoprotein 72), T-cell receptor, TEM1 (Tumor endothelial marker 1), TENB2, Tenascin C (TN-C), Tie, TIM-1, Tn, TNF, TNFRSF8, TNFRSF1OB (tumor necrosis factor receptor superfamily member 10B), TNFRSF13B (tumor necrosis factor receptor superfamily member 13B), TRAIL-R1, TRAILR2 (Death receptor 5 (DR5)), tumor-associated calcium signal transducer 2, tumor specific glycosylation of MUC1, TWEAK receptor, TYRP1 (glycoprotein 75), VEGFR-1, VEGFR-2, or vimentin.

17. The compound according to claim 15, wherein the tumor cell is selected from the group consisting of lymphoma cells, myeloma cells, renal cells, breast cancer cells, prostate cancer cells, ovarian cancer cells, colorectal cancer cells, gastric cancer cells, squamous cancer cells, small-cell lung cancer cells, non small-cell lung cancer cells, and testicular cancer cells.

18. A pharmaceutical composition comprising a therapeutically effective amount of the conjugate compound of claim 2 or 8 or a pharmaceutically acceptable salt thereof, and, optionally, a carrier, diluent, or excipient.

19. The conjugate compound of any one of claims 2, 4, 8 and 12, wherein the drug is selected from the group consisting of a toxin, a chemotherapeutic agent, a drug moiety, an antibiotic, a radioactive isotope, a nucleolytic enzyme and a chromophore molecule.

20. The compound of Formula (I) of any one of claims 1, 5 and 6, wherein the compound of Formula (I) comprises one or more linker components of: 6-maleimidocaproyl (MC), maleimido propanoyl (MP), valine-citrulline (val-cit), alanine-phenyl alanine (ala-phe), lysine-phenylalanine (lys-phe), p-aminobenzyloxycarbonyl (PAB), 4-thio-pentanoate (SPP), 4-(N-maleimidomethyl)cyclohexane-1-carboxylate (MCC), 4-thio-butyrate (SPDB), maleimidoethyl (ME), 4-thio-2-hydroxysulfonyl-butyrate (2-Sulfo-SPDB), pyridinyl-dithiol (PySS), alkoxy amino (AOA), ethyleneoxy (EO), 4-methyl-4-dithio-pentanoic (MPDP), azido ($N_3$), alkynyl, dithio, and/or (4-acetyl)aminobenzoate (SIAB).

21. The conjugate compound of any one of claims 2 and 8, wherein "Drug" is selected from the group consisting of tubulysins, maytansinoids, taxanoids (taxanes), CC-1065 analogs, daunorubicin and doxorubicin compounds, benzodiazepine dimers, calicheamicins and the enediyne antibiotics, actinomycin, azaserines, bleomycins, epirubicin, tamoxifen, idarubicin, dolastatins/auristatins comprising monomethyl auristatin E, MMAF, auristatin PYE, auristatin TP, Auristatins 2-AQ, 6-AQ, EB (AEB), and EFP (AEFP), duocarmycins, thiotepa, vincristine, hemiasterlins, nazumamides, microginins, radiosumins, alterobactins, microsclerodermins, theonellamides, and esperamicins.

22. The compound according to any one of claims 1 and 4 having formula compound 5, 9, 16, 19, 27, 29, 30, 35, 40, 47, 50, 51, 53, 62, 63, 65, 68, 69, 74, 75, 77, 84, 85, 88, 89, 94, 95, 99, 100, 108, 109, 114, 115, 121, 123, 124, 135, 136, 141, 142, 144, 147a, 147b, 147c, 147d, 153, 158, 172, 173, 174, 182, 183, 193, 194, 195, 202, 203, 204, 207, 208, or 209, illustrated below:

5

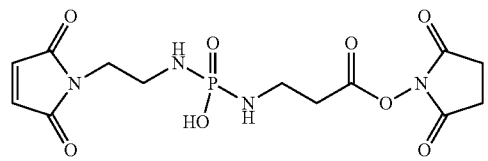

16

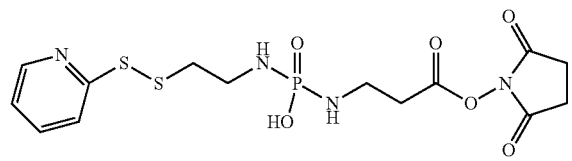

-continued
9
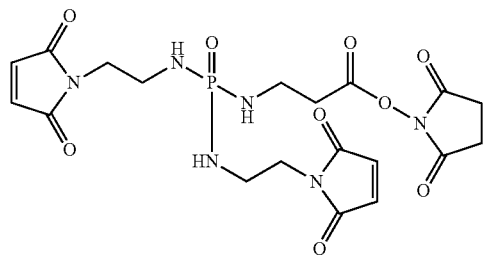
19
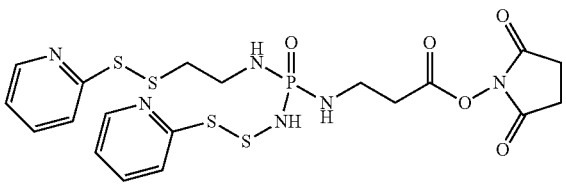
27
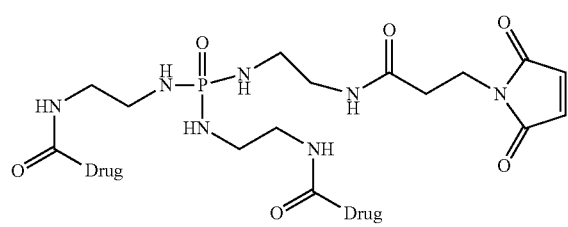
29
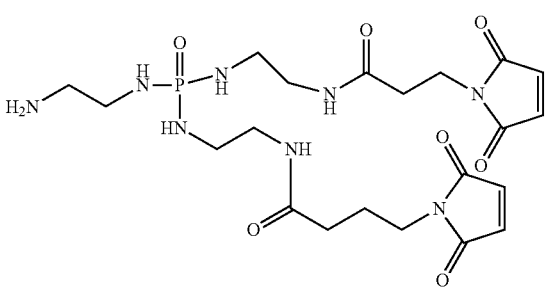
33
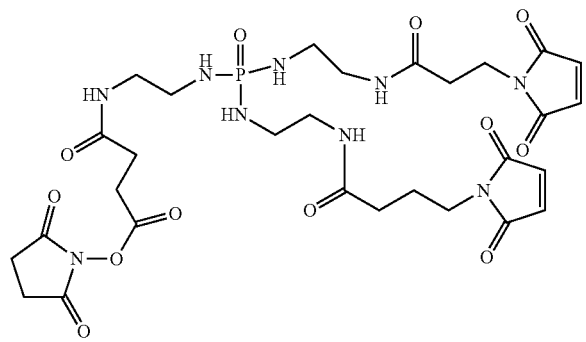
30
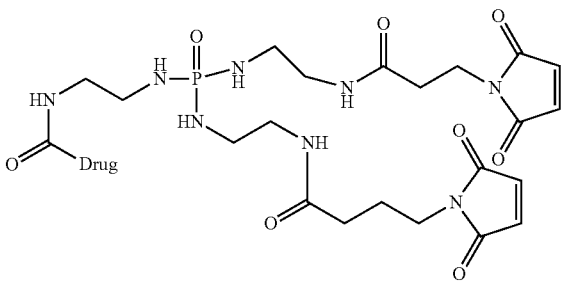
35
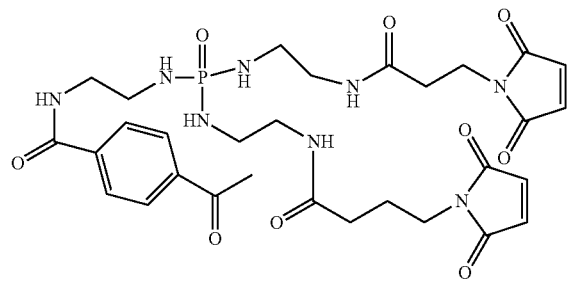
40
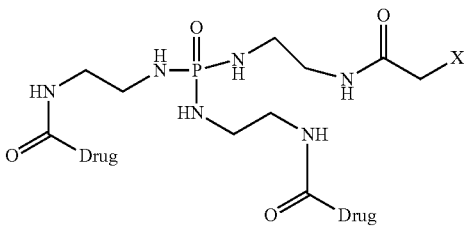
47
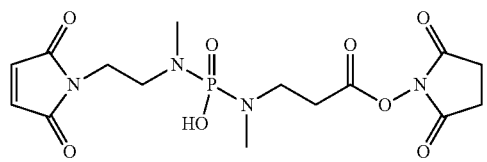
50
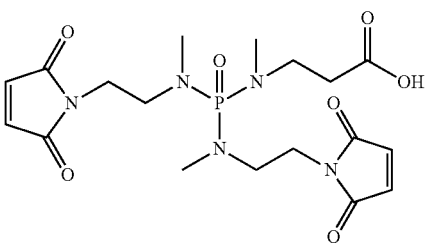

-continued
51
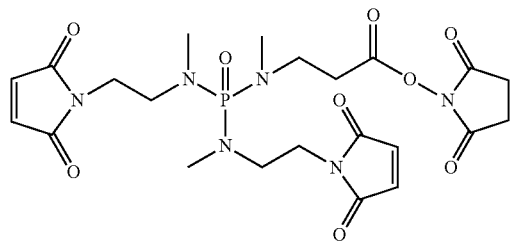
53
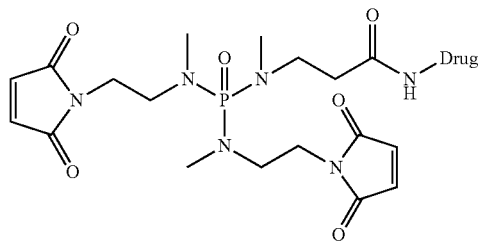
62
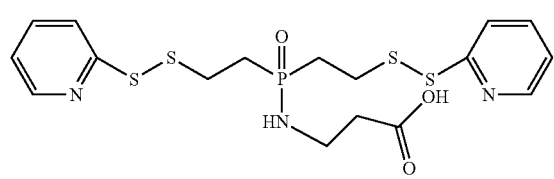
63
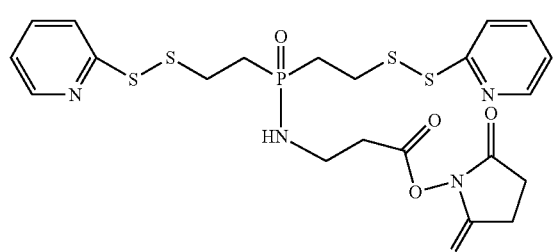
65
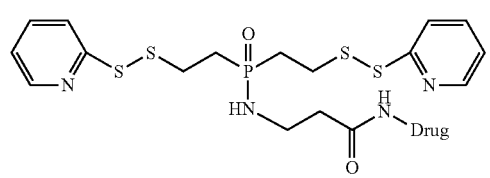
68
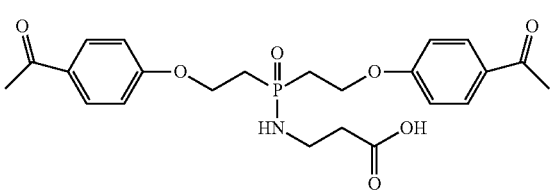
69
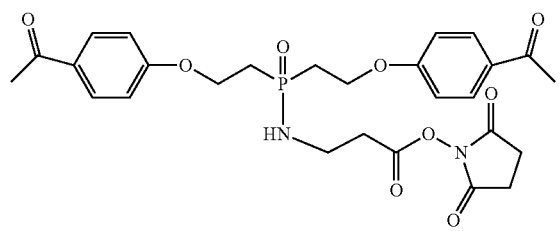
74
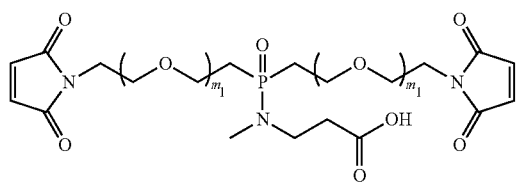
75
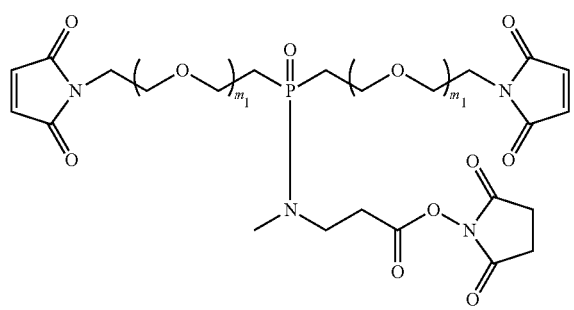
77
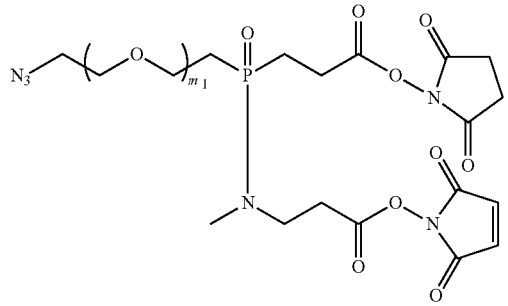
84
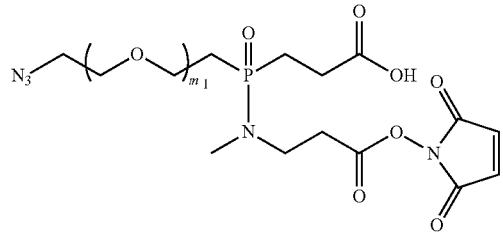
85

88
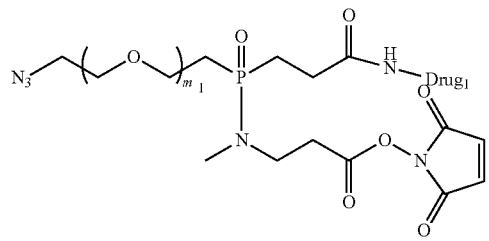
89
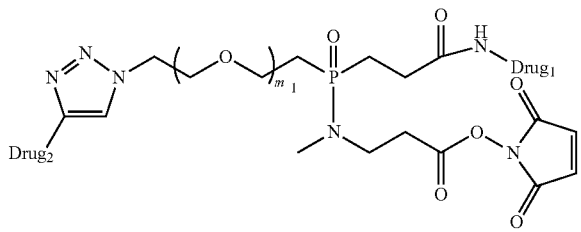
94
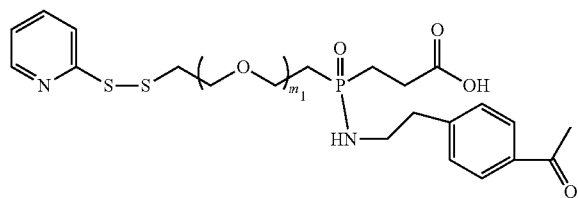
95
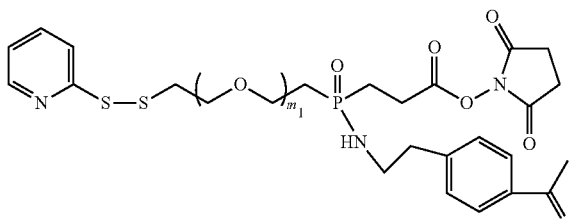
99
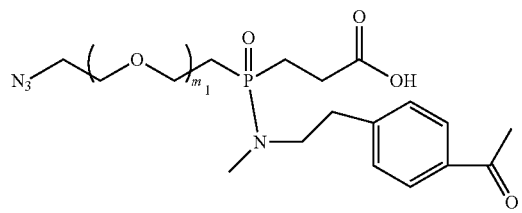
100
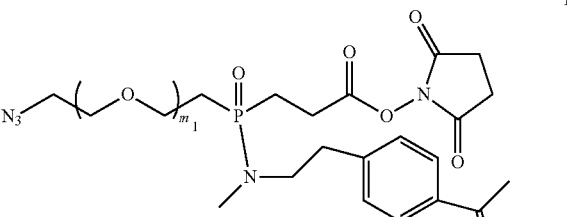
108
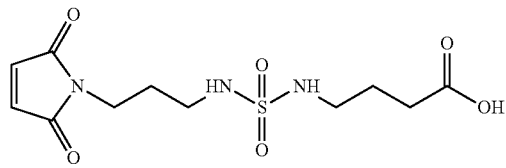
109
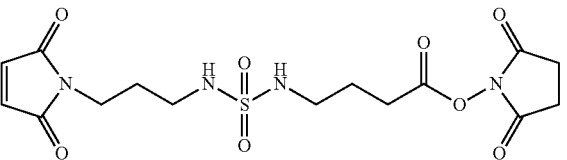
114
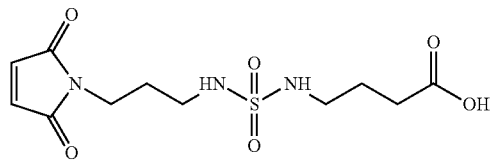
115
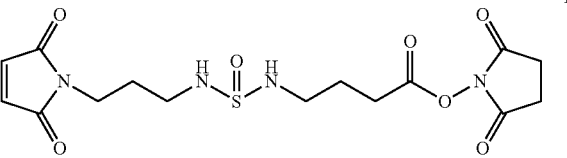
121
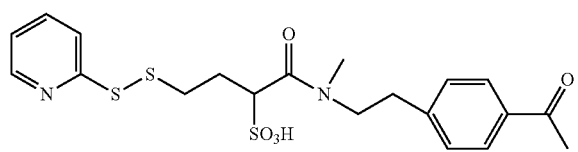
123
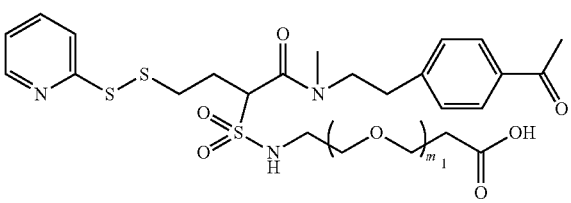
124
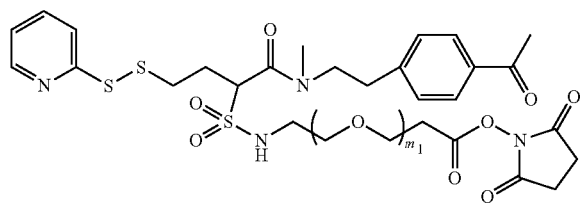
135
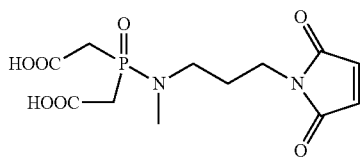

-continued
136
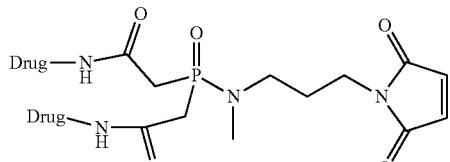
141
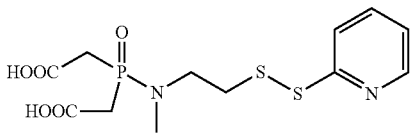
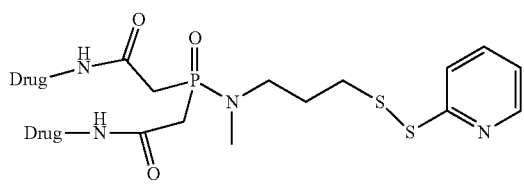
142
153
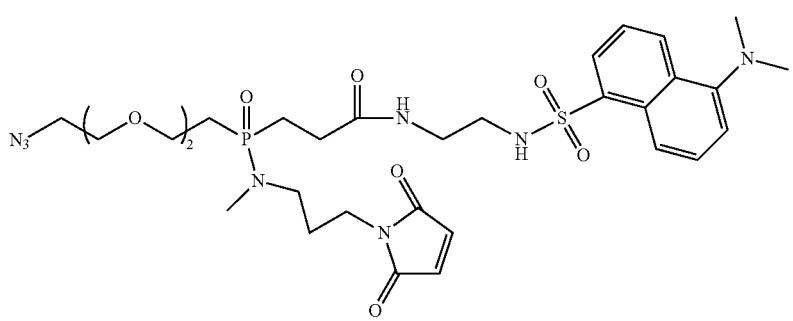
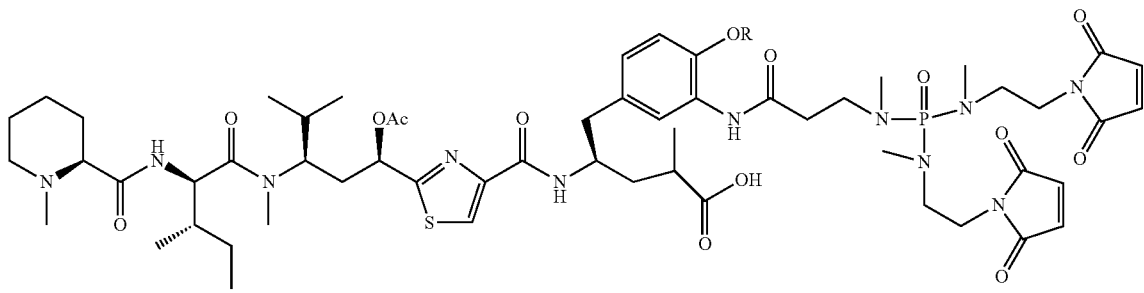
147a, R = H
147b, R = PO₃H₂
147c, R = SO₃H
147d, R = CH₂OPO₃H₂
158
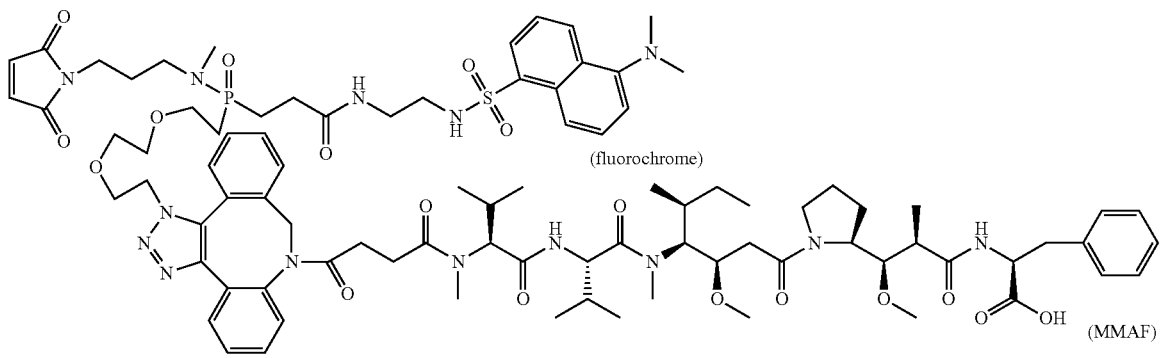
(fluorochrome)
(MMAF)
144
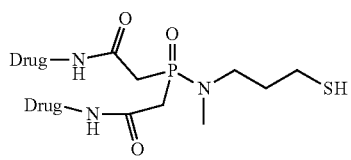
172
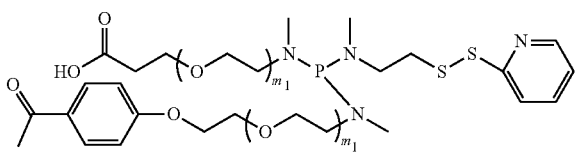

-continued
173
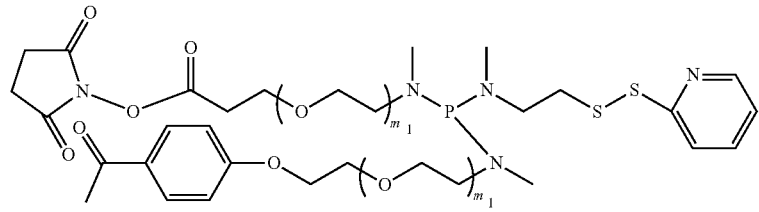
174a
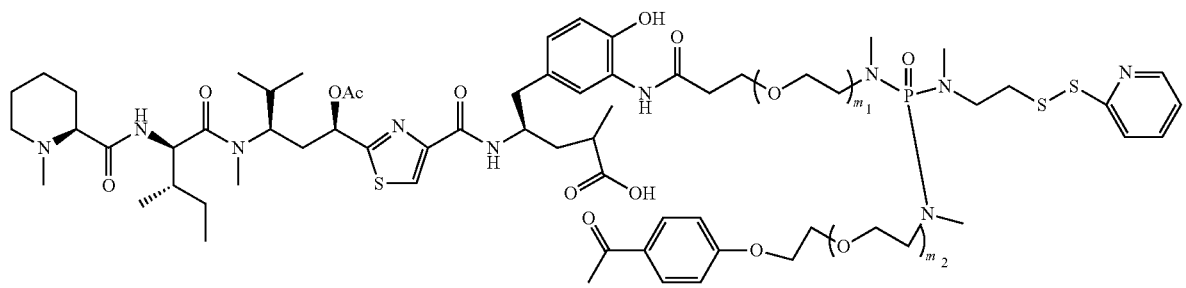
182a
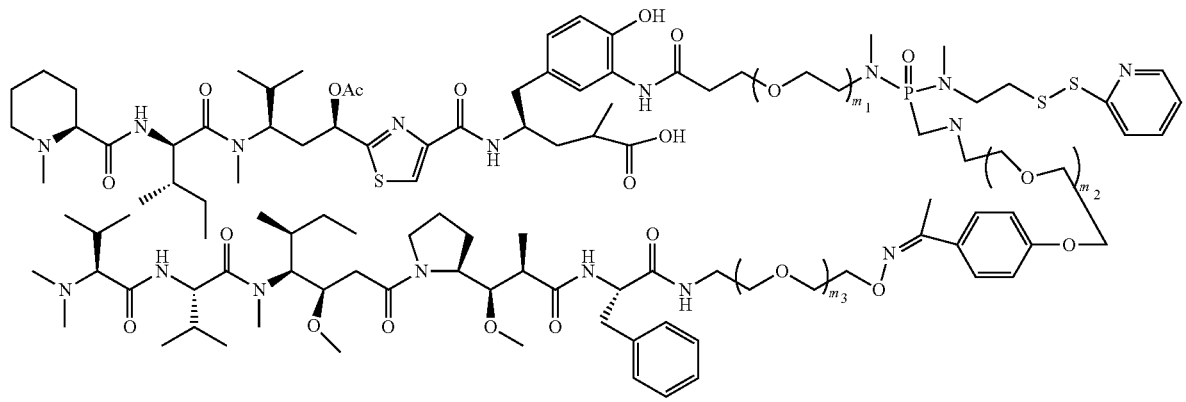
183a
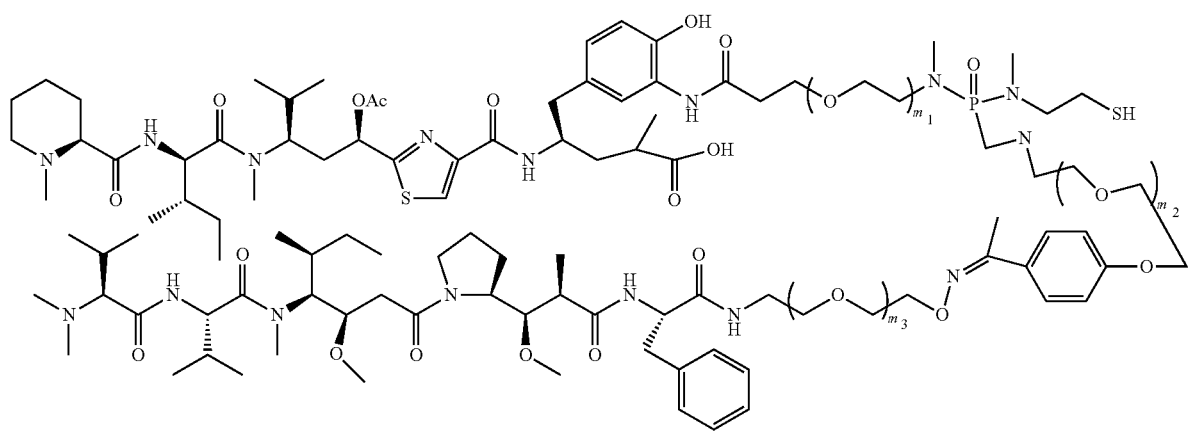
$m_1, m_2, m_3 = 0\text{-}24$
independently

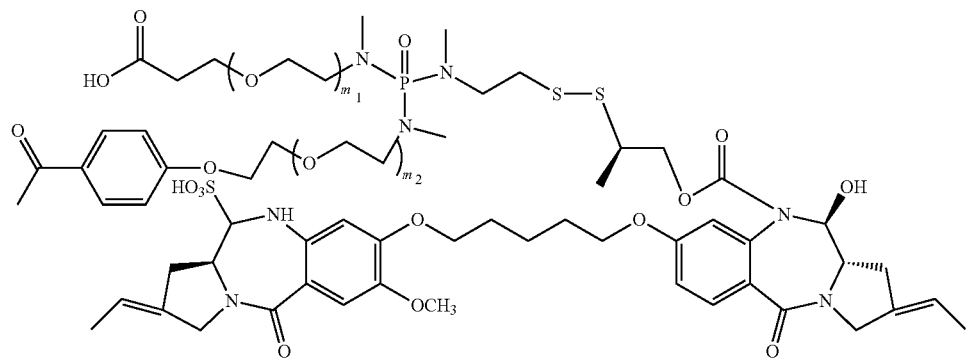
193
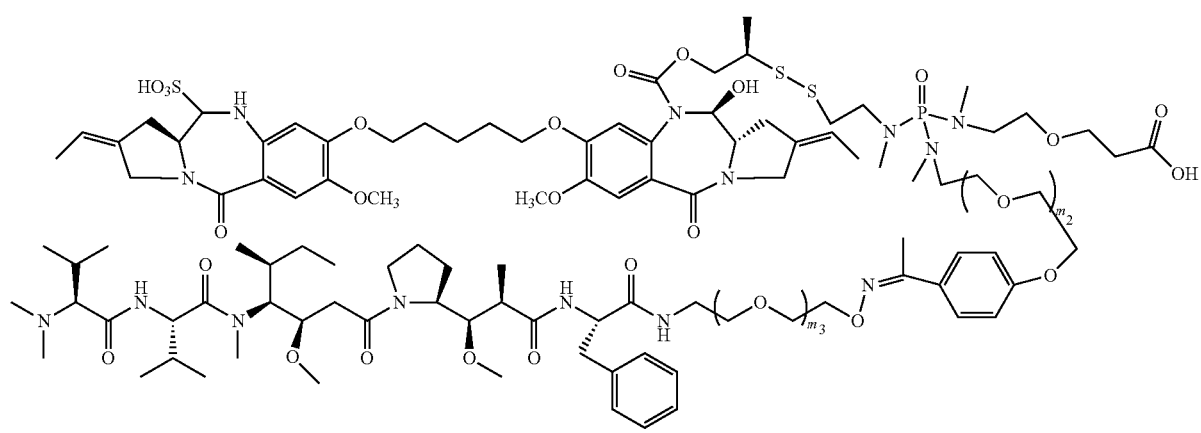
184
$m_1, m_2, m_3 = 0\sim24$
independently
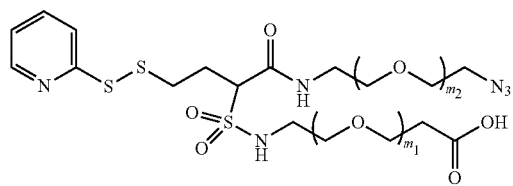
202
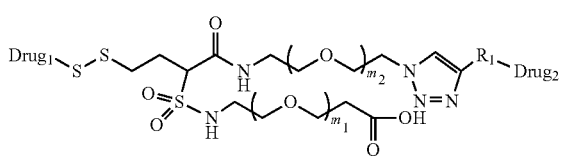
203
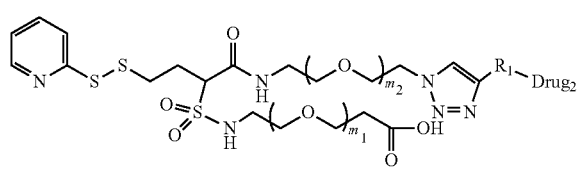
207
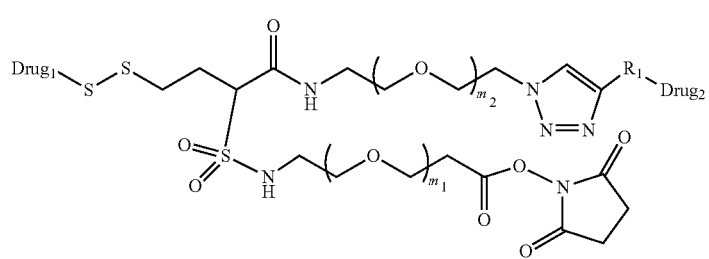
208
209 wherein $m_1$, $m_2$ and $m_3$ are 0 to 24 independently, $R_1$ and Drug are defined in claim 1.
23. The compound according to any one of claims 2 and 3 having formula 6, 17, 10, 12, 20, 22, 28, 31, 34, 36, 37, 41, 48, 52, 54, 64, 66, 70, 71, 76, 78, 86, 87, 90, 96, 97, 101, 102, 110, 116, 125, 126, 127, 137, 143, 145, 148a, 148b, 148c, 148d, 159, 184, 185, 194, 197, 205, or 210, illustrated below:
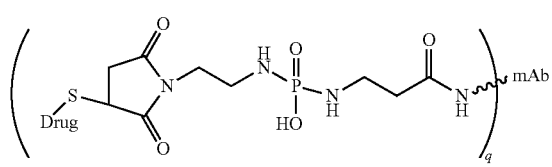
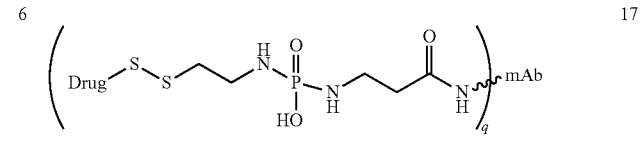
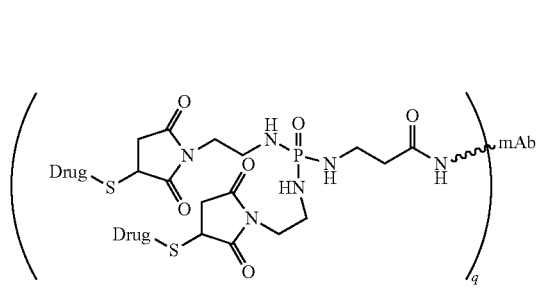
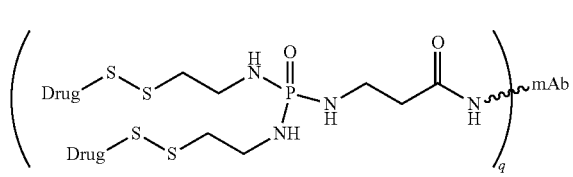
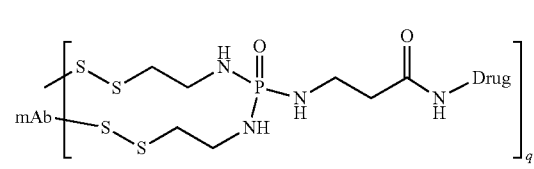
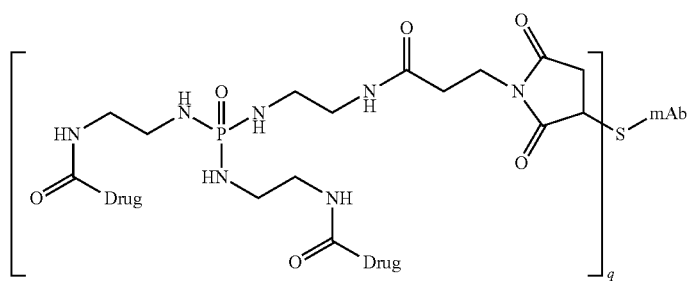
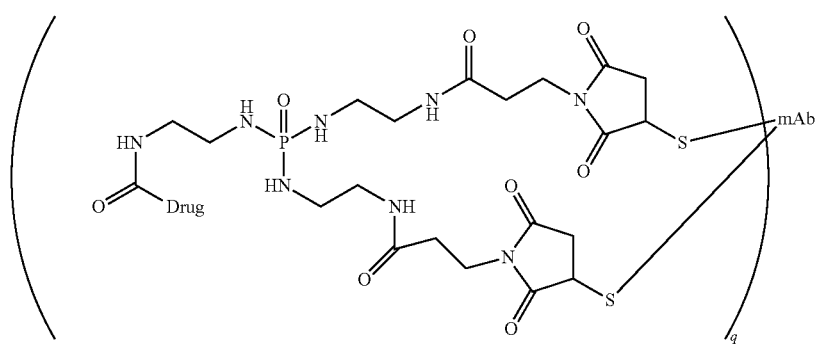

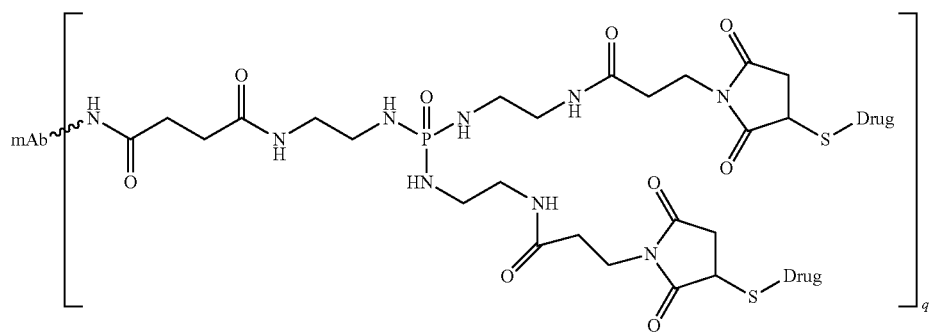
34
q = 1~30
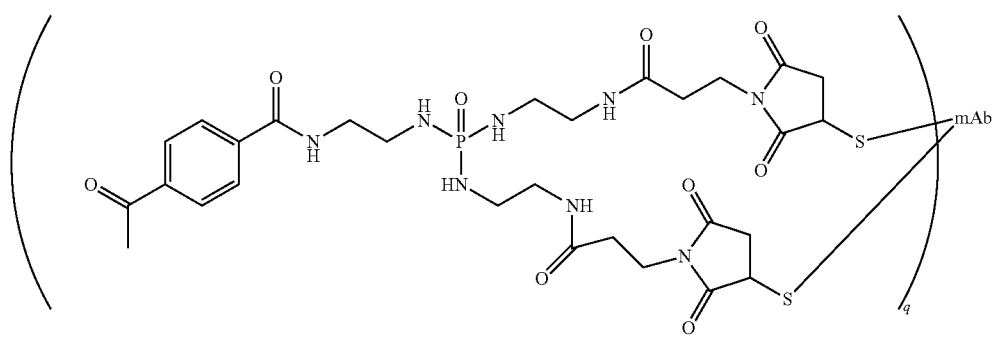
36
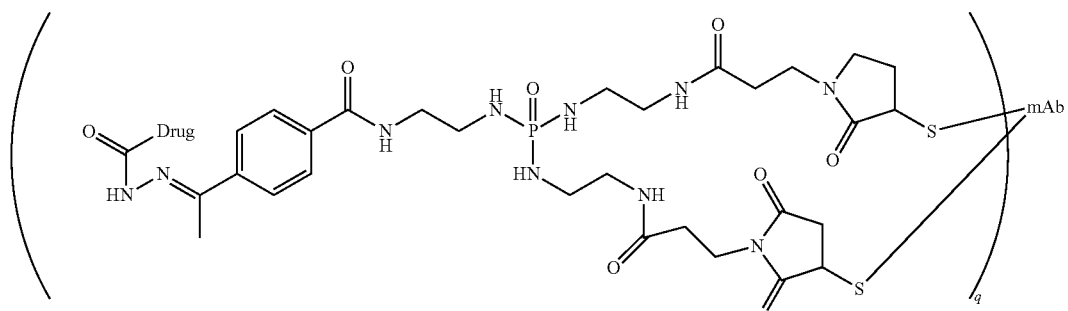
37
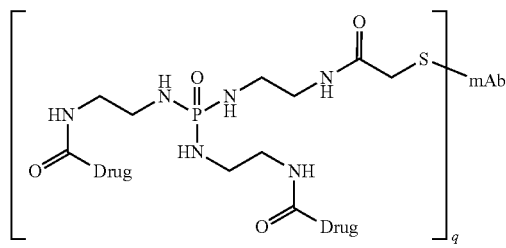
41
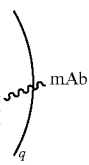
48
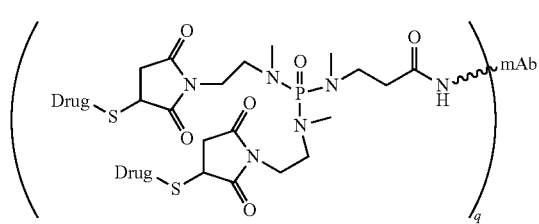
52
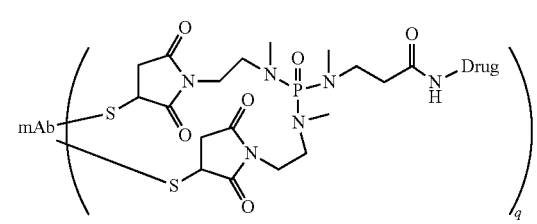
54

-continued
64
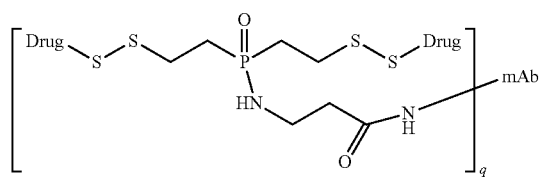
66
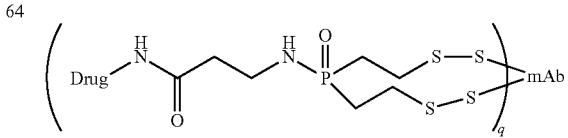
70
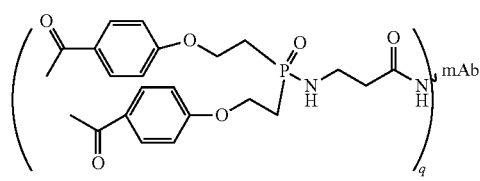
71
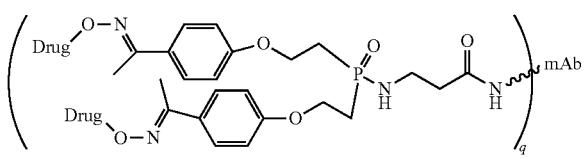
76
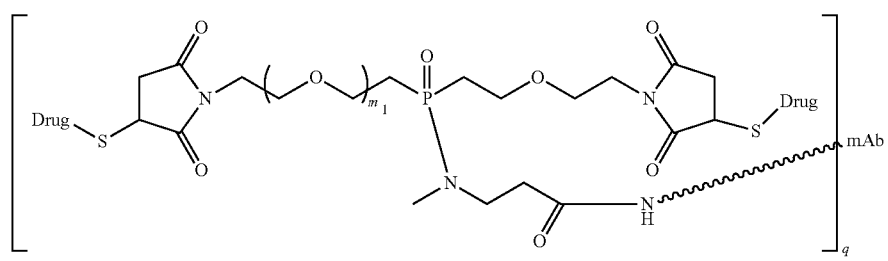
$m_1 = 0\sim24, q = 1\sim20$
78
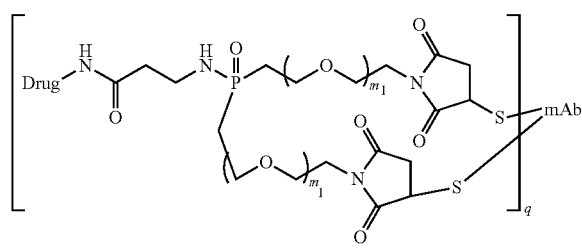
86
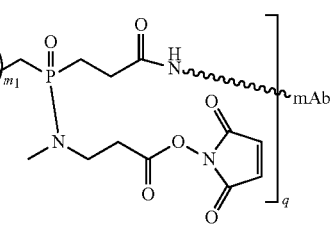
87
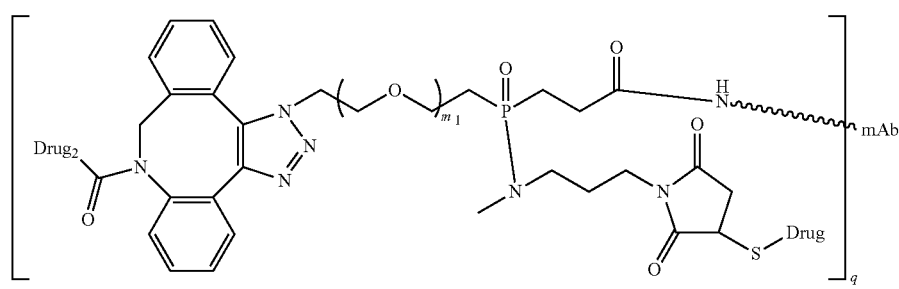
$m_1 = 0\sim24, q = 1\sim30$
90
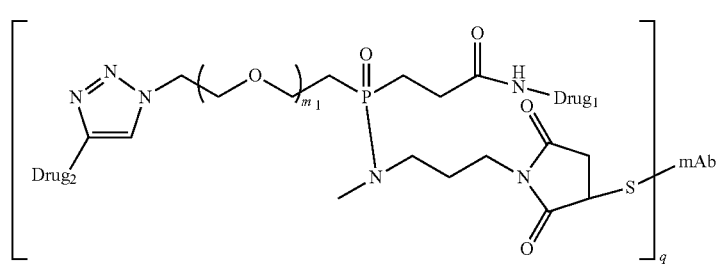

-continued
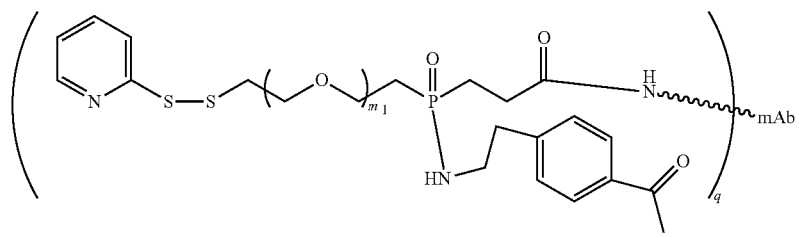
96
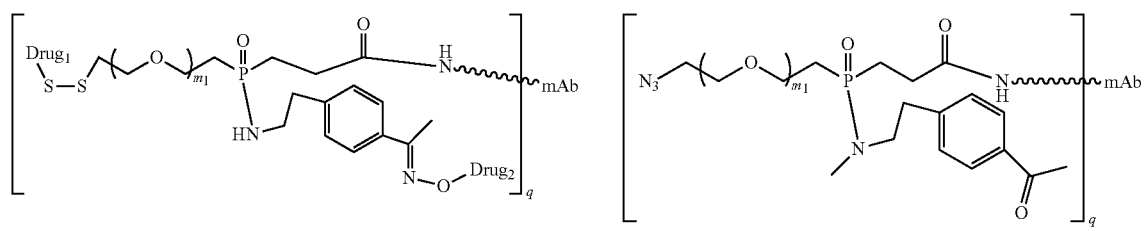
97
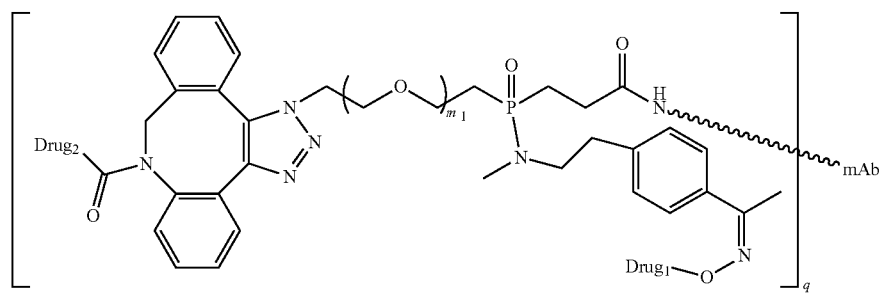
102
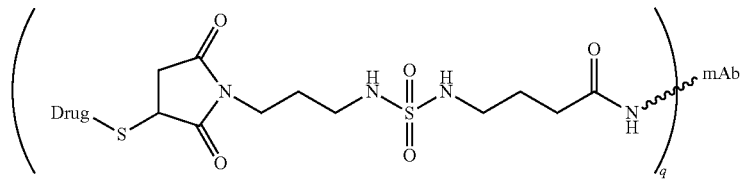
110
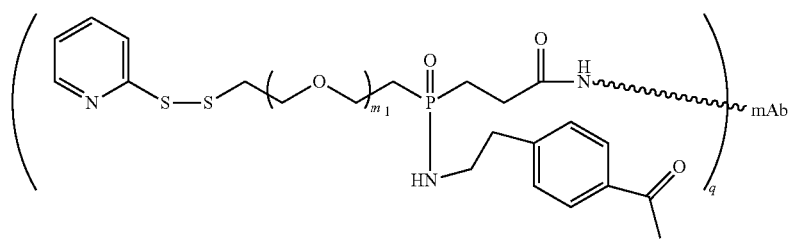
96
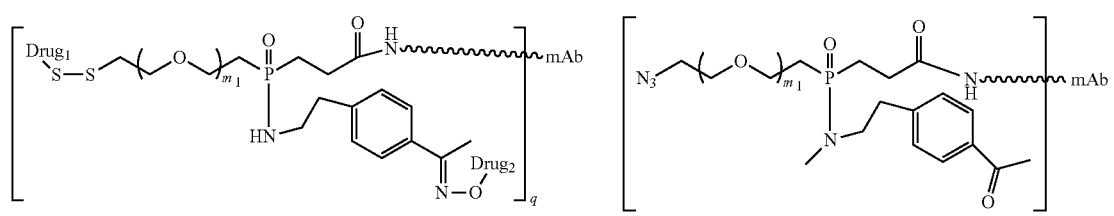
97                                                                101

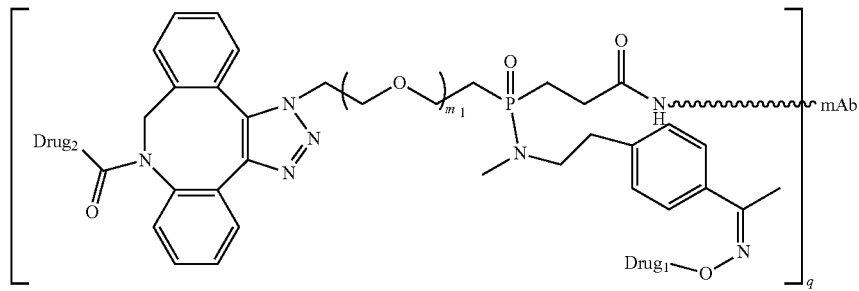
102
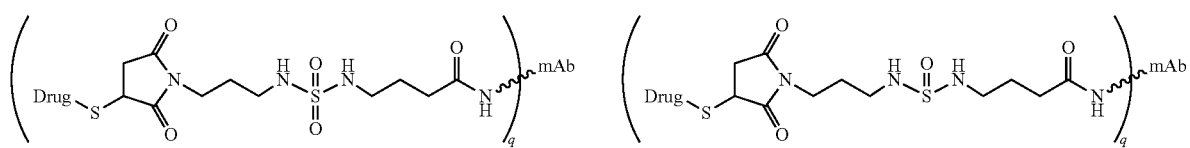
110
116
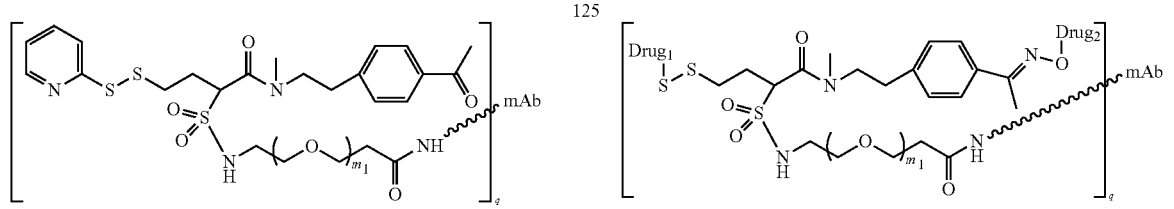
125
126
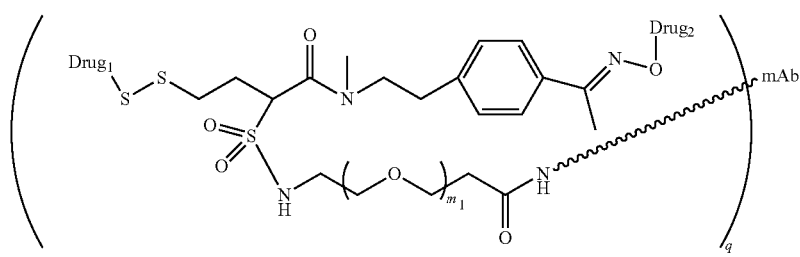
127
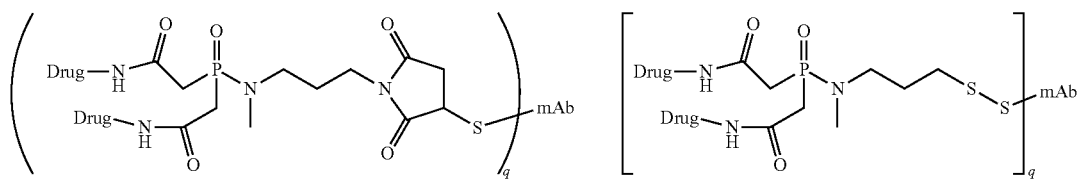
137
143
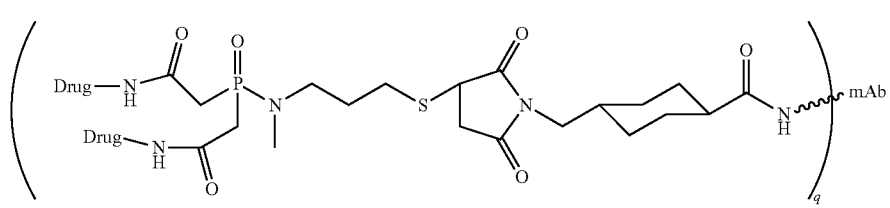
145

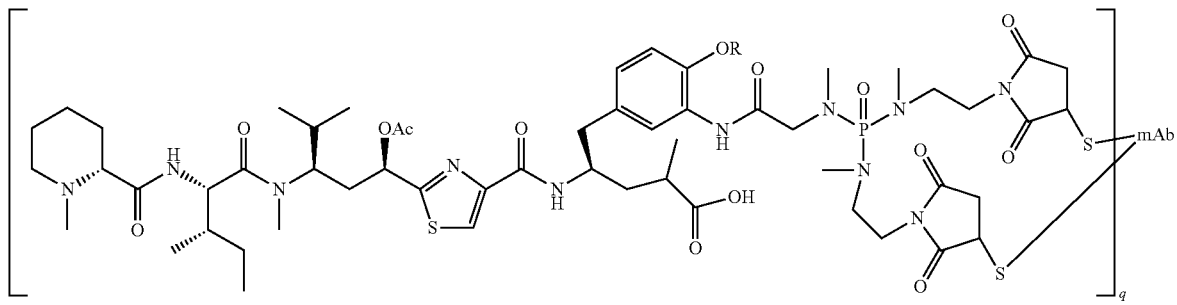
148a, R = H; 148a, R = PO₃H₂; 148c, R = SO₃H; 148d, R = CH₂OPO₃H₂
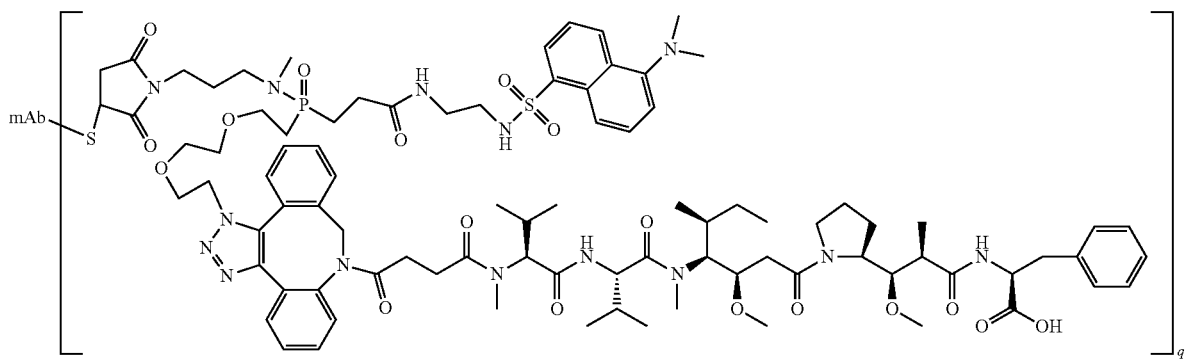
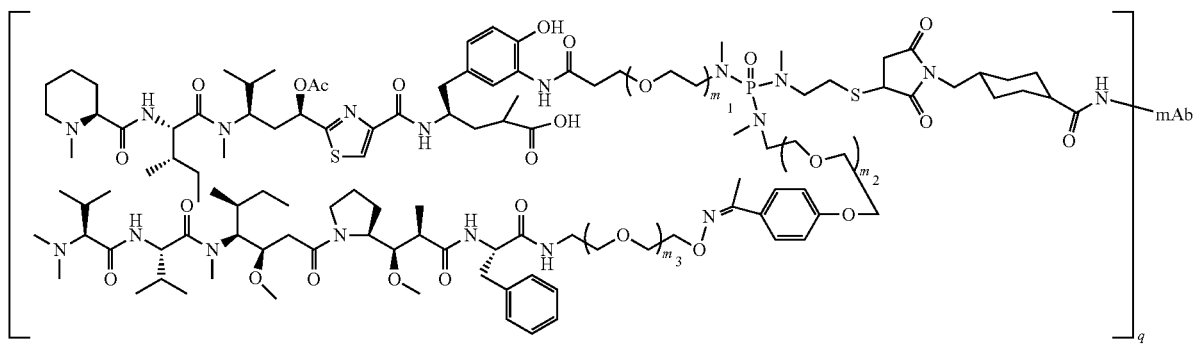
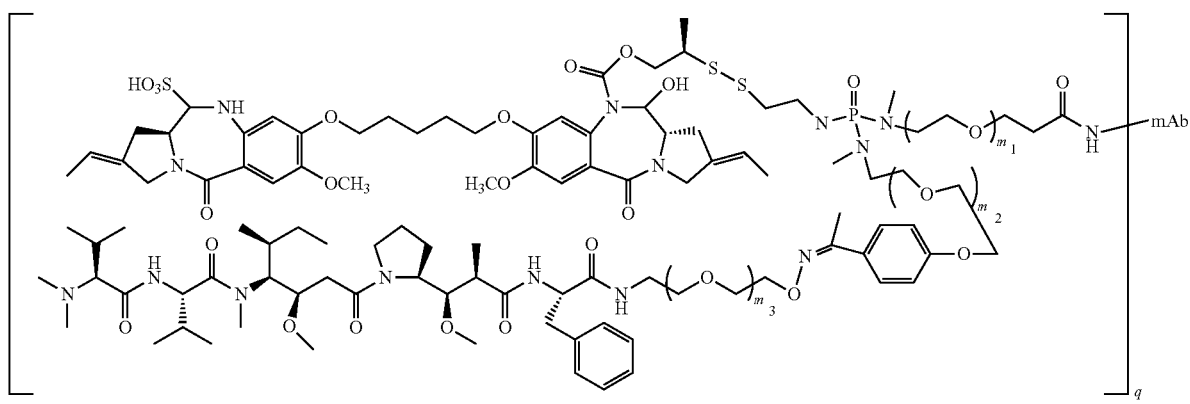

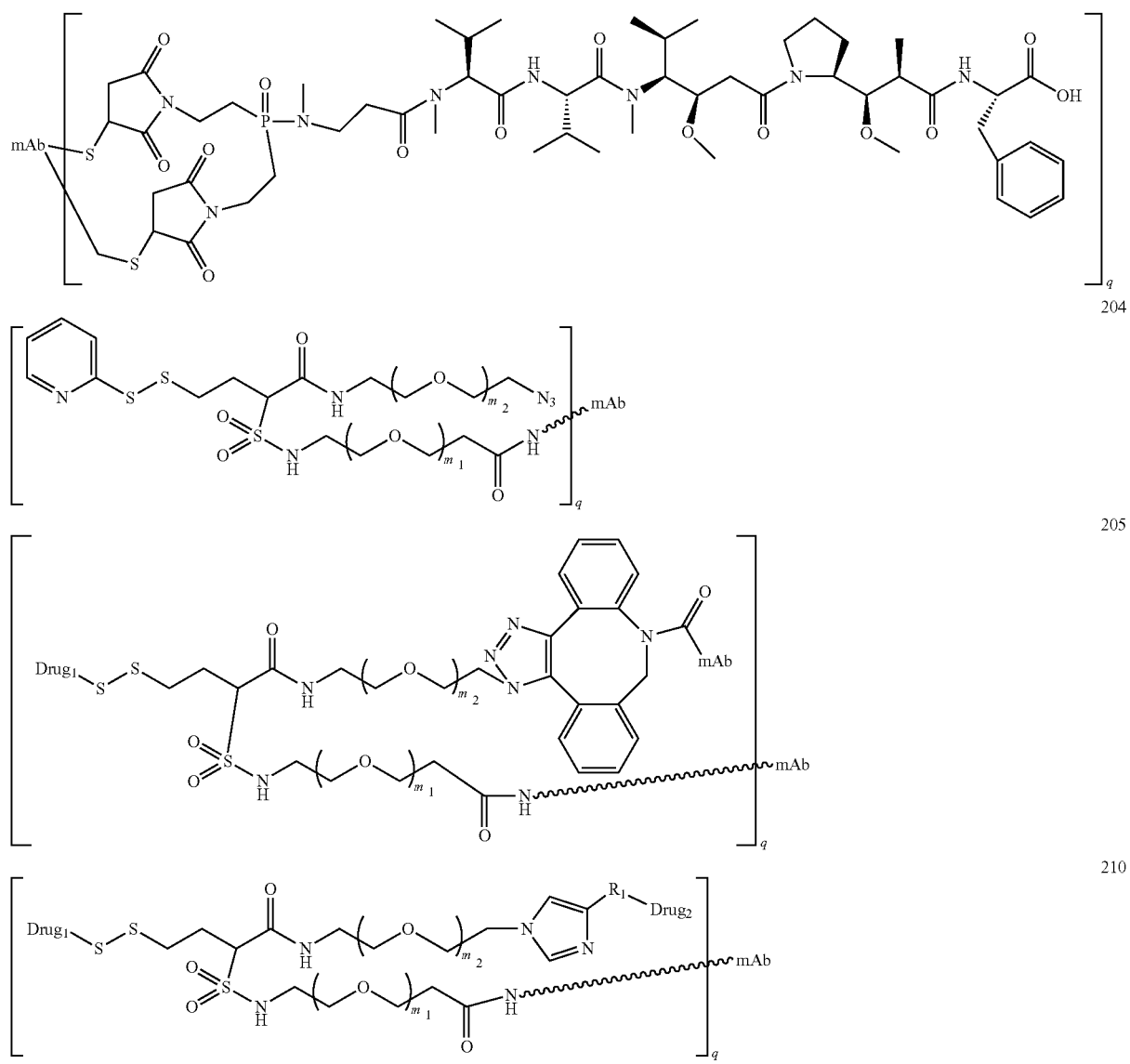

wherein $m_1$, $m_2$ and $m_3$ are 0 to 24 independently, $R_1$, q and Drug are defined in claim 2.

24. The conjugate compound of claim 2, 7, or 8, having in vitro, in vivo or ex vivo cell killing activity.

25. The conjugate compound of claim 2, 7, or 8, comprising either a peptide of 1 to 20 units of natural or unnatural amino acids, or a p-aminobenzyl unit, or a 6-maleimidocaproyl unit, or a disulfide unit, or a thioether unit, or a hydrozone unit, or a triazole unit, or an alkoxime unit.

26. The conjugate compound of claim 2, 7 or 8, which is cleavable by a protease.

27. The pharmaceutical composition of claim 18, further comprising an agent which is a chemotherapeutic agent, radiation therapy agent, immunotherapy agent, autoimmune disorder agent, or anti-infectious agent.

28. The pharmaceutical composition according to claim 27, wherein the agent is selected from the group consisting of Abatacept, Abiraterone acetate, Acetaminophen /hydrocodone, Adalimumab, afatinib dimaleate, alemtuzumab, Alitretinoin, ado-trastuzumab emtansine, Amphetamine mixed salts, anastrozole, Aripiprazole, Atazanavir, Atezolizumab, Atorvastatin, axitinib, belinostat, Bevacizumab, Cabazitaxel, Cabozantinib, bexarotene, blinatumomab, Bortezomib, bosutinib, brentuximab vedotin, Budesonide, Buprenorphine, Capecitabine, carfilzomib, Celecoxib, ceritinib, Cetuximab, Ciclosporin, Cinacalcet, crizotinib, Dabigatran, dabrafenib, Darbepoetin alfa, Darunavir, dasatinib, denileukin diftitox, Denosumab, Depakote, Dexlansoprazole, Dexmethylphenidate, Dinutuximab, Doxycycline, Duloxetine, Emtricitabine/Rilpivirine/Tenofovir disoproxil fumarate, Emtricitabine/tenofovir/efavirenz, Enoxaparin, Enzalutamide, Epoetin alfa, erlotinib, Esomeprazole, Eszopiclone, Etanercept, Everolimus, exemestane, Ezetimibe, Fenofibrate, Filgrastim, fingolimod, Fluticasone propionate, fulvestrant, gefitinib, Glatiramer, Goserelin acetate, Imatinib, Ibritumomab tiuxetan, ibrutinib, idelalisib, Infliximab, Insulin aspart, Insulin detemir, Insulin glargine, Insulin lispro, Interferon beta 1a, Interferon beta 1b, lapatinib, Ipilimumab, Ipratropium bromide/salbutamol, Lanreotide acetate, lenalidomide, letrozole, Levothyroxine, Lidocaine, Linezolid, Liraglutide, Li sdexamfetamine, MEDI4736, Memantine, Methylphenidate, Metoprolol, Modafinil, Mometasone, Nilotinib, Nivolumab, ofatumumab, obinutuzumab, olapari, Olmesartan, Omalizumab, Omega-3 fatty acid ethyl esters, Oseltamivir, Oxycodone, palbociclib, Palivizumab, panitumumab, panobinostat, pazopanib, pembrolizumab, Pemetrexed, pertuzumab, Pneumococcal conjugate vaccine, pomalidomide, Pregabalin, Quetiapine, Rabeprazole, radium 223 chloride, Raloxifene, Raltegravir, ramucirumab, Ranibizumab, regorafenib, Rituximab, Rivaroxaban, romidepsin, Rosuvastatin, ruxolitinib phosphate, Salbutamol, Sevelamer, Sildenafil, siltuximab, Sitagliptin, Solifenacin, Sorafenib, Sunitinib, Tadalafil, tamoxifen, Telaprevir, temsirolimus, Tenofovir/emtricitabine, Testosterone gel, Thalidomide, Tiotropium bromide, toremifene, trametinib, Trastuzumab, Tretinoin, Ustekinumab, Valsartan, vandetanib, vemurafenib, vorinostat, ziv-aflibercept, Zostavax, pharmaceutically acceptable salts thereof, and a combination thereof.

29. A method for treatment of a cancer or an autoimmune disease, comprising administering to a patient in need thereof, the pharmaceutical composition of claim 18.

30. The compound of any one of claims 2 and 4, wherein Drug is a fluorophore molecule selected from the group consisting of 2',7'-Dichorodihydro-fluorescein, Dihydrorhodamine 123, Fluo-3, Fluo-4, Indo-1, seminaphtharhodafluors, Allophycocyanin, AmCyanl, AsRed2, Azami Green, Azurite, B-phycoerythrin, Cerulean, CyPet, DsRed monomer, DsRed2, EBFP, EBFP2, ECFP, EGFP, Emerald, EYFP, GFP, GFPuv, HcRedl, J-Red, Katusha, Kusabira Orange, mCFP, mCherry, mCitrine, Midoriishi Cyan, mKate, mKeima-Red, mKO, mOrange, mPlum, mRaspberry, mRFP1, mStrawberry, mTFP1, mTurquoise2, P3, Peridinin Chlorophyll, R-phycoerythrin, T-Sapphire, TagCFP, TagGFP, TagRFP, TagYFP, tdTomato, Topaz, TurboFP602, TurboFP635, TurboGFP, TurboRFP, TurboYFP, Venus, Wild Type GFP, YPet, ZsGreenl, and ZsYellowl.

31. A method for forming a conjugate compound, comprising administering the compound of claim 2 or 4 to a targeted cell, wherein "Drug" is a chromophore molecule.

32. The compound of any one of claims 2, 4, 8 and 12, wherein Drug comprises a chemotherapeutic agent, an anti-autoimmune disease agent, a radioisotope, or a chromophore molecule.

33. The compound of claim 2, wherein the cell binding agent is selected from the group consisting of 3F8, Abagovomab, Abciximab, Adalimumab, Adecatumumab, Afelimomab; Afutuzumab, Alacizumab pegol, ALD518, Alemtuzumab, Altumomab, Anatumomab, Anrukinzumab, Apolizumab, Arcitumomab, Aselizumab, Atlizumab, Atorolimumab, Bapineuzumab, Basiliximab, Bavituximab, Bectumomab, Belimumab, Benralizumab, Bertilimumab, Besilesomab, Biciromab, Bivatuzumab, Blinatumomab, Brentuximab, Briakinumab, Canakinumab, Cantuzumab, Capromab, Catumaxomab, CC49, Cedelizumab, Certolizumab pegol, Cetuximab, Citatuzumab bogatox, Cixutumumab, Clenoliximab, Clivatuzumab, Conatumumab, CR6261, Dacetuzumab, Daclizumab, Daratumumab, Denosumab, Detumomab, Dorlimomab, Dorlixizumab, Ecromeximab, Eculizumab, Edobacomab, Edrecolomab, Efalizumab, Efungumab, Elotuzumab, Elsilimomab, Enlimomab pegol, Epitumomab, Epratuzumab, Erlizumab, Ertumaxomab, Etaracizumab, Exbivirumab, Fanolesomab, Faralimomab, Farletuzumab, Felvizumab, Fezakinumab, Figitumumab, Fontolizumab, Foravirumab, Fresolimumab, Galiximab, Gantenerumab, Gavilimomab, Gemtuzumab, Girentuximab, Glembatumumab, Golimumab, Gomiliximab, Ibalizumab, Ibritumomab, Igovomab, Imciromab, Infliximab, Intetumumab, Inolimomab, Inotuzumab, Ipilimumab, Iratumumab, Keliximab, Labetuzumab, Lebrikizumab, Lemalesomab, Lerdelimumab, Lexatumumab, Libivirumab, Lintuzumab, Lucatumumab, Lumiliximab, Mapatumumab, Maslimomab, Matuzumab, Mepolizumab, Metelimumab, Milatuzumab, Minretumomab, Mitumomab, Morolimumab, Motavizumab, Muromonab-CD3, Nacolomab, Naptumomab, Natalizumab, Nebacumab, Necitumumab, Nerelimomab, Nimotuzumab, Nofetumomab, Ocrelizumab, Odulimomab, Ofatumumab, Olaratumab, Omalizumab, Oportuzumab, Oregovomab, Otelixizumab, Pagibaximab, Palivizumab, Panitumumab, Panobacumab, Pascolizumab, Pemtumomab, Pertuzumab, Pexelizumab, Pintumomab, Priliximab, Pritumumab, PRO 140, Racotumomab, Rafivirumab, Ramucirumab, Ranibizumab, Raxibacumab, Regavirumab, Reslizumab, Rilotumumab, Rituximab, Robatumumab, Rontalizumab, Rovelizumab, Ruplizumab, Satumomab, Sevirumab, Sibrotuzumab, Sifalimumab, Siltuximab, Siplizumab, Lintuzumab, Solanezumab, Sonepcizumab, Sontuzumab, Stamulumab, Sulesomab, Tacatuzumab, Tadocizumab, Talizumab, Tanezumab, Taplitumomab, Tefibazumab, Telimomab, Tenatumomab, Teneliximab, Teplizumab, TGN1412, Ticilimumab, Tigatuzumab, TNX-650, Tocilizumab, Tositumomab, Trastuzumab, Tremelimumab, Tucotuzumab celmoleukin, Tuvirumab, Urtoxazumab, Ustekinumab, Vapaliximab, Vedolizumab, Veltuzumab, Vepalimomab, Visilizumab, humanized LM609 monoclonal antibody, Volociximab, Votumumab, Zalutumumab, Zanolimumab, Ziralimumab, Zolimomab, Etanercept, Alefacept, Abatacept, Rilonacept, 14F7, 14G2a, J591, 225.28S, COL-1, CYT-356, HNK20, ImmuRAIT, Lym-1, MAK-195F, MEDI-500, RING SCAN, Avicidin, Epratuzumab, Apolizumab, $^{131}$I-Lym-1, monoclonal antibody MEDI-507, anti-VEGF; Labetuzumab, IMC-1C11 and Cetuximab.

34. The compound according to claim 2 or 3, wherein the cell binding agent is capable of targeting against any one of the following: B lymphoma cells, Cytomegalovirus, Hepatitis B virus, HIV-1, *Escherichia coli, Pseudomonas aeruginosa*, respiratory syncytial virus, prostate carcinoma, cells expressing an insulin growth factor receptor or cells expressing an epidermal growth factor receptor.

35. The compound according to claim 2 or 3, wherein the cell binding agent is capable of targeting against anti-transferrin receptor.

* * * * *